(12) United States Patent
Ando et al.

(10) Patent No.: US 8,158,650 B2
(45) Date of Patent: Apr. 17, 2012

(54) SUBSTITUTED PHENYLMETHYL BICYCLOCARBOXYAMIDE COMPOUNDS

(75) Inventors: Koji Ando, Chita-gun (JP); Hirotaka Tanaka, Chita-gun (JP)

(73) Assignee: Pfizer Inc., New York, NY (US)

( * ) Notice: Subject to any disclaimer, the term of this patent is extended or adjusted under 35 U.S.C. 154(b) by 399 days.

(21) Appl. No.: 12/445,500

(22) PCT Filed: Oct. 11, 2007

(86) PCT No.: PCT/IB2007/003106
§ 371 (c)(1),
(2), (4) Date: Apr. 14, 2009

(87) PCT Pub. No.: WO2008/050199
PCT Pub. Date: May 2, 2008

(65) Prior Publication Data
US 2010/0087480 A1   Apr. 8, 2010

Related U.S. Application Data

(60) Provisional application No. 60/862,485, filed on Oct. 23, 2006.

(51) Int. Cl.
C07D 215/38 (2006.01)
A61K 31/04 (2006.01)
(52) U.S. Cl. ........................ 514/312; 546/159
(58) Field of Classification Search ............... 546/159; 514/312
See application file for complete search history.

(56) References Cited

U.S. PATENT DOCUMENTS

| | | | |
|---|---|---|---|
| 7,084,176 B2 | 8/2006 | Morie et al. | 514/563 |
| 7,393,958 B2* | 7/2008 | Bertinato et al. | 546/156 |
| 2007/0105943 A1 | 5/2007 | Nakamoto et al. | 514/430 |

FOREIGN PATENT DOCUMENTS

| | | |
|---|---|---|
| WO | WO02100819 | 12/2002 |
| WO | WO03014064 | 2/2003 |
| WO | WO03035621 | 5/2003 |
| WO | WO03068749 | 8/2003 |
| WO | WO03080578 | 10/2003 |
| WO | WO2004069792 | 8/2004 |
| WO | WO2005003084 | 1/2005 |
| WO | WO2005033079 | 4/2005 |
| WO | WO2005070885 | 8/2005 |
| WO | WO2005070929 | 8/2005 |
| WO | WO2005095329 | 10/2005 |
| WO | WO2006051378 | 5/2006 |

OTHER PUBLICATIONS

Salman, CA 152:304125, abstract only of WO 2004106299, 2004.*
Honore, J PHarm and Exp Therapeutics, vol. 314, No. 1, pp. 410-421, 2005.*
European Journal of Physiology, vol. 451, pp. 1510159 (2005).
Clinical Therapeutics, vol. 13(3), pp. 338-395 (1991).
Journal of Pharmacology and Experimental Therapeutics, vol. 314, pp. 410-421 (2005).
Neuroscience Letters, vol. 388, pp. 75-80 (2005).

* cited by examiner

Primary Examiner — D M Seaman
(74) Attorney, Agent, or Firm — A. Dean Olson

(57) ABSTRACT

This invention provides a compound of the formula (I). These compounds are useful for the treatment of disease conditions caused by overactivation of the VR1 receptor such as pain, or the like in mammal. This invention also provides a pharmaceutical composition comprising the above compound.

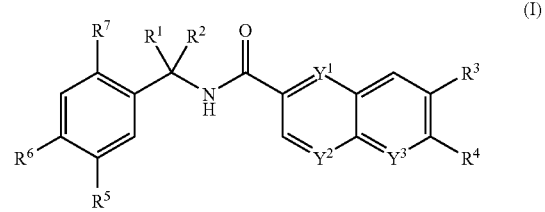

18 Claims, No Drawings

SUBSTITUTED PHENYLMETHYL BICYCLOCARBOXYAMIDE COMPOUNDS

This application claims priority from International Application Number PCT/IB2007/003106 filed Oct. 11, 2007 which claims priority from U.S. Provisional Application 60/862,485 filed Oct. 23, 2006.

TECHNICAL FIELD

This invention relates to novel substituted phenylmethyl bicyclocarboxamide compounds and to their use in therapy. These compounds are particularly useful as modulators of the VR1 (Type I Vanilloid) receptor, and are thus useful for the treatment of diseases such as pain, neuralgia, neuropathies, nerve injury, burns, migraine, carpal tunnel syndrome, fibromyalgia, neuritis, sciatica, pelvic hypersensitivity, bladder disease, inflammation, or the like in mammals, especially humans. The present invention also relates to a pharmaceutical composition comprising the above compounds.

BACKGROUND ART

The Vanilloid receptor 1 (VR1) is a ligand gated nonselective cation channel. It is believed to be a member of the transient receptor potential super family. VR1 is recognized as a polymodal nociceptor that integrates multiple pain stimuli, e.g., noxious heat, protons, and vanilloids (European Journal of Physiology 451:151-159, 2005). A major distribution of VR1 is in the sensory (Aδ- and C-) fibres, which are bipolar neurons having somata in sensory ganglia. The peripheral fibres of these neurons innervate the skin, the mucosal membranes, and almost all internal organs. It is also recognized that VR1 exists in bladder, kidney, brain, pancreas, and various kinds of organs. A body of studies using VR1 agonists, e.g., capsaicin or resiniferatoxin, have suggested that VR1 positive nerves are thought to participate in a variety of physiological responses, including nociception (Clinical Therapeutics. 13(3): 338-395, 1991, Journal of Pharmacology and Experimental Therapeutics 314:410-421, 2005, and Neuroscience Letter 388: 75-80, 2005). Based on both the tissue distribution and the roles of VR1, VR1 antagonists would have good therapeutic potential.

WO2005070929 discloses heterocyclic amine derivatives as vanilloid receptor ligands. WO2005070885 discloses amide derivatives useful as vanilloid receptor ligands. WO2005003084 discusses 4-(methylsulfonylamino)phenyl analogues which are stated to have activity as VR1 antagonists. WO 2004069792 discloses quinoline-derived amide derivatives useful for prevention or treatment of e.g. inflammatory pain, burning pain, chronic obstructive pulmonary disease and osteoarthritis, are vanilloid receptor 1 modulators. WO 2003080578 discloses heteroaromatic urea derivatives are vanilloid-1 receptor modulators used for treating diseases and conditions in which pain and/or inflammation predominates. WO 2003068749 discloses quinoline or isoquinoline carboxamide derivatives useful as antagonist of the vanilloid receptor (VR1). WO 2003014064 discloses amide derivatives useful as vanilloid receptor 1 antagonists. WO 2002100819 discloses N-arylphenylacetamide derivatives as vanilloid receptor VR1 antagonists for e.g. treating pain, mania and allergic rhinitis. WO2006051378 discloses a variety of N-sulfonylaminobenzyl-2-phenoxy amide derivatives as modulator of the vanilloid receptor. JP11080107 discloses amide compounds as bone formation promoters for use as antiosteoporotic agents. WO2005033079 discloses heterocyclic derivatives, useful for treating fungal infections. WO03035621 discloses naphthyl amide compounds as protein kinase and phosphatase inhibitors for treating e.g. diabetes, obesity and hearing loss.

It is desirable to provide new VR1 selective antagonist with potent binding activity and good metabolic stability. Other potential advantages include low toxicity, good absorption, good solubility, low protein binding affinity, low drug-drug interaction, a reduced inhibitory activity at HERG channel and reduced QT prolongation.

BRIEF DISCLOSURE OF THE INVENTION

It has now been found that certain substituted carboxamide derivatives are potent VR1 antagonists with analgesic activity by systemic administration.

The present invention provides a compound of the following formula (I):

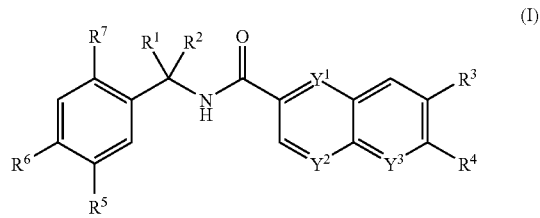

wherein
$Y^1$ and $Y^2$ are each independently CH or N, $Y^3$ is $CR^8$ or N, with the proviso that only one of $Y^1$, $Y^2$ and $Y^3$ is N;
$R^1$ and $R^2$ are each independently hydrogen, $(C_1-C_6)$alkyl, halo$(C_1-C_6)$alkyl or hydroxy$(C_1-C_6)$alkyl;
$R^3$ is hydrogen, halogen, hydroxy, $(C_1-C_6)$alkyl, hydroxy$(C_1-C_6)$alkyl, hydroxy$(C_1-C_6)$alkoxy, $(C_1-C_6)$alkoxy-$(C_1-C_6)$alkyl, $(C_1-C_6)$alkoxy-$(C_1-C_6)$alkoxy or halo$(C_1-C_6)$alkyl;
$R^4$ is halogen, $(C_1-C_6)$alkyl, $(C_3-C_6)$cycloalkyl, halo$(C_1-C_6)$alkyl, hydroxy$(C_1-C_6)$alkyl, halo$(C_1-C_6)$alkoxy, hydroxy$(C_1-C_6)$alkoxy, $(C_1-C_6)$alkoxy-$(C_1-C_6)$alkyl, $(C_1-C_6)$alkoxy-$(C_1-C_6)$alkoxy, halo$(C_1-C_6)$alkylsulfonyl, halo$(C_1-C_6)$alkylsulfinyl, halo$(C_1-C_6)$alkylthio, $[(C_1-C_6)$alkyl]NH—, $[(C_1-C_6)$alkyl$]_2$N—, azetidinyl, pyrrolidinyl or piperidinyl;
$R^6$ is hydroxy, hydroxy$(C_1-C_6)$alkyl, or $(C_1-C_6)$alkoxy;
$R^5$ is hydrogen, halogen, hydroxy, $(C_1-C_6)$alkyl, hydroxy$(C_1-C_6)$alkyl, or $(C_1-C_6)$alkoxy;
$R^7$ is hydrogen, halogen, hydroxy, $(C_1-C_6)$alkyl, hydroxy$(C_1-C_6)$alkyl, or $(C_1-C_6)$alkoxy;
$R^8$ is hydrogen, halogen, $(C_1-C_6)$alkyl, or halo$(C_1-C_6)$alkyl;
or a pharmaceutically acceptable salt or solvate thereof.

DETAILED DESCRIPTION OF THE INVENTION

As used herein, the term "halogen" means fluoro, chloro, bromo or iodo, preferably fluoro or chloro.

As used herein, the terms "$(C_1-C_6)$alkyl" and "$(C_1-C_4)$alkyl" mean straight or branched chain saturated radicals having the required number of carbon atoms, including, but not limited to methyl, ethyl, n-propyl, iso-propyl, n-butyl, iso-butyl, secondary-butyl, tert-butyl and 2-methylbutyl groups. Preferred groups are methyl, ethyl, n-propyl, n-butyl, tert-butyl and 2-methylbutyl groups.

As used herein, the terms "$(C_3-C_6)$cycloalkyl" means nonaromatic saturated or unsaturated hydrocarbon ring, having the required number of carbon atoms, including, but not limited to cyclopropyl, cyclobutyl, cyclopentyl and cyclohexyl groups.

As used herein, the term "$(C_1-C_6)$alkoxy" means $(C_1-C_6)$alkyl-O— wherein $(C_1-C_6)$alkyl radical is as defined above, including, but not limited to methoxy, ethoxy, n-propoxy, iso-propoxy, n-butoxy, iso-butoxy, sec-butoxy and tert-butoxy. Preferred groups are methoxy, ethoxy, n-propoxy, n-butoxy and tert-butoxy.

As used herein, the term "hydroxy$(C_1-C_6)$alkyl" means $(C_1-C_6)$alkyl radical as defined above which is substituted by at least one hydroxy group including, but not limited to, hydroxymethyl, hydroxyethyl, hydroxy n-propyl, hydroxy iso-propyl (e. g. 1-hydroxy-1,1-dimethylmethyl), hydroxy n-butyl, hydroxy iso-butyl, hydroxy secondary-butyl and hydroxy tert-butyl. Preferred groups are hydroxymethyl, hydroxyethyl, hydroxy n-propyl, hydroxy iso-propyl (e. g. 1-hydroxy-1,1-dimethylmethyl), hydroxy n-butyl and hydroxy tert-butyl.

As used herein, the term "hydroxy$(C_1-C_6)$alkoxy" means $(C_1-C_6)$alkoxy radical as defined above which is substituted by hydroxy group including, but not limited to, hydroxymethoxy, hydroxyethoxy, hydroxy n-propoxy, hydroxy iso-propoxy, hydroxy n-butoxy, hydroxy iso-butoxy, hydroxy sec-butoxy and hydroxy tert-butoxy. Preferred hydroxyalkoxy groups are hydroxymethoxy, hydroxyethoxy, hydroxy n-propoxy and hydroxy n-butoxy.

As used herein, the term "$(C_1-C_6)$alkoxy-$(C_1-C_6)$alkyl" means $(C_1-C_6)$alkyl radical as defined above which is substituted by $(C_1-C_6)$alkoxy group as defined above.

As used herein, the term "$(C_1-C_6)$alkoxy-$(C_1-C_6)$alkoxy" means $(C_1-C_6)$alkoxy radical as defined above which is substituted by $(C_1-C_6)$alkoxy as defined above. Preferred groups are methoxy methoxy, methoxy ethoxy or ethoxy ethoxy groups.

As used herein, the term "hydroxy$(C_1-C_6)$alkoxy-$(C_1-C_6)$alkyl" means $(C_1-C_6)$alkyl radical as defined above which is substituted by hydroxy$(C_1-C_6)$alkoxy group or radical as defined above which is substituted by hydroxy$(C_1-C_4)$alkoxy group as defined above.

As used herein the term "halo$(C_1-C_6)$alkyl" and "halo$(C_1-C_4)$alkyl" mean $(C_1-C_6)$alkyl or $(C_1-C_4)$alkyl radical which is substituted by one or more halogen atoms as defined above including, but not limited to, fluoromethyl, difluoromethyl, trifluoromethyl, 2-fluoroethyl, 2,2-difluoroethyl, 2,2,2-trifluoroethyl, 2,2,2-trifluoro-1,1-dimethylethyl, 2,2,2-trichloroethyl, 3-fluoropropyl, 4-fluorobutyl, chloromethyl, trichloromethyl, iodomethyl, bromomethyl and 4,4,4-trifluoro-3-methylbutyl groups. Preferred groups are fluoromethyl, difluoromethyl, trifluoromethyl, 2-fluoroethyl, 2,2-difluoroethyl, 2,2,2-trifluoroethyl and 2,2,2-trifluoro-1,1-dimethylethyl groups.

As used herein the terms "halo$(C_1-C_6)$alkoxy" mean $(C_1-C_6)$alkyl-O—, which is substituted by one or more halogen atoms as defined above including, but not limited to, fluoromethoxy, difluoromethoxy, trifluoromethoxy, 2-fluoroethoxy, 2,2-difluoroethoxy, 2,2,2-trifluoroethoxy, 2,2,2-trifluoro-1,1-dimethylethoxy, 2,2,2-trichloroethoxy, 3-fluoropropoxy, 4-fluorobutoxy, chloromethoxy, trichloromethoxy, iodomethoxy, bromomethoxy and 4,4,4-trifluoro-3-methylbutoxy groups. Preferred halo$(C_1-C_6)$alkyl-O— or halo$(C_1-C_3)$alkyl-O— groups are fluoromethoxy, difluoromethoxy, trifluoromethoxy, 2-fluoroethoxy, 2,2-difluoroethoxy, 2,2,2-trifluoroethoxy and 2,2,2-trifluoro-1,1-dimethylethoxy groups.

As used herein, the terms "$(C_1-C_6)$alkylthio" means $(C_1-C_6)$alkyl-S— wherein $(C_1-C_6)$alkyl radical is as defined above, including, but not limited to methylthio, ethylthio, propylthio and butylthio. Preferred groups are methylthio and ethylthio groups.

As used herein, the terms "$(C_1-C_6)$alkylsulfinyl" means $(C_1-C_6)$alkyl-SO— wherein $(C_1-C_6)$alkyl radical is as defined above, including, but not limited to methylsulfinyl, ethylsulfinyl, propylsulfinyl and butylsulfinyl. Preferred groups are methylsulfinyl and ethylsulfinyl groups.

As used herein, the terms "$(C_1-C_6)$alkylsulfonyl" means $(C_1-C_6)$alkyl-SO$_2$— wherein $(C_1-C_6)$alkyl radical is as defined above, including, but not limited to methylsulfonyl, ethylsulfonyl, propylsulfonyl and butylsulfonyl. Preferred groups are methylsulfonyl and ethylsulfonyl groups.

As used herein, the terms "halo$(C_1-C_6)$alkylthio" means $(C_1-C_6)$alkyl-S—, which is substituted by one or more halogen atoms as defined above, including, but not limited to fluoromethylthio, difluoromethylthio, trifluoromethylthio, 2-fluoroethylthio, 2,2-difluoroethylthio, 2,2,2-trifluoroethylthio, 2,2,2-trifluoro-1,1-dimethylethylthio, 2,2,2-trichloroethylthio, 3-fluoropropylthio, 4-fluorobutylthio, chloromethylthio, trichloromethylthio, iodomethylthio, bromomethylthio and 4,4,4-trifluoro-3-methylbutylthio groups. Preferred groups are fluoromethylthio, difluoromethylthio, trifluoromethylthio, 2-fluoroethylthio, 2,2-difluoroethylthio, 2,2,2-trifluoroethylthio and 2,2,2-trifluoro-1,1-dimethylethylthio groups.

As used herein, the terms "halo$(C_1-C_6)$alkylsulfinyl" means $(C_1-C_6)$alkyl-SO—, which is substituted by one or more halogen atoms as defined above, including, but not limited to fluoromethylsulfinyl, difluoromethylsulfinyl, trifluoromethylsulfinyl, 2-fluoroethylsulfinyl, 2,2-difluoroethylsulfinyl, 2,2,2-trifluoroethylsulfinyl, 2,2,2-trifluoro-1,1-dimethylethylsulfinyl, 2,2,2-trichloroethylsulfinyl, 3-fluoropropylsulfinyl, 4-fluorobutylsulfinyl, chloromethylsulfinyl, trichloromethylsulfinyl, iodomethylsulfinyl, bromomethylsulfinyl and 4,4,4-trifluoro-3-methylbutylsulfinyl groups. Preferred groups are fluoromethylsulfinyl, difluoromethylsulfinyl, trifluoromethylsulfinyl, 2-fluoroethylsulfinyl, 2,2-difluoroethylsulfinyl, 2,2,2-trifluoroethylsulfinyl and 2,2,2-trifluoro-1,1-dimethylethylsulfinyl groups.

As used herein, the terms "halo$(C_1-C_6)$alkylsulfonyl" means $(C_1-C_6)$alkyl-SO$_2$—, which is substituted by one or more halogen atoms as defined above, including, but not limited to fluoromethylsulfonyl, difluoromethylsulfonyl, trifluoromethylsulfonyl, 2-fluoroethylsulfonyl, 2,2-difluoroethylsulfonyl, 2,2,2-trifluoroethylsulfonyl, 2,2,2-trifluoro-1,1-dimethylethylsulfonyl, 2,2,2-trichloroethylsulfonyl, 3-fluoropropylsulfonyl, 4-fluorobutylsulfonyl, chloromethylsulfonyl, trichloromethylsulfonyl, iodomethylsulfonyl, bromomethylsulfonyl and 4,4,4-trifluoro-3-methylbutylsulfonyl groups. Preferred groups are fluoromethylsulfonyl, difluoromethylsulfonyl, trifluoromethylsulfonyl, 2-fluoroethylsulfonyl, 2,2-difluoroethylsulfonyl, 2,2,2-trifluoroethylsulfonyl and 2,2,2-trifluoro-1,1-dimethylethylsulfonyl groups.

As used herein, the term "[$(C_1-C_6)$alkyl]NH—" means alkyl-NH— wherein alkyl is defined above, including, but not limited to methylamino, ethylamino, n-propylamino, iso-propylamino, n-butylamino, iso-butylamino, secondary-butylamino, tert-butylamino. Preferred alkylamino groups are methylamino, ethylamino, n-propylamino, and n-butylamino.

As used herein, the term "[$(C_1-C_6)$alkyl]$_2$N—" means dialkyl-N— wherein alkyl is defined above, including, but not limited to dimethylamino, diethylamino, methylethylamino, di n-propylamino, methyl n-propylamino, ethyl n-propylamino diiso-propylamino, di n-butylamino, methyl n-butylamino di iso-butylamino, di secondary-butylamino, di tert-butylamino. Preferred dialkylamino groups are dimethylamino, diethylamino, di n-propylamino, di n-butylamino.

Preferred structures of the formula (I) include as follows:
Preferably, $R^8$ is H.
Preferably, $Y^1$ is CH, $Y^2$ is CH and $Y^3$ is CH.
Preferably, $Y^1$ is N, $Y^2$ is CH and $Y^3$ is CH.
Preferably, $Y^1$ is CH, $Y^2$ is N and $Y^3$ is CH.
Preferably, $Y^1$ is CH, $Y^2$ is CH and $Y^3$ is N.
Preferably, $R^1$ and $R^2$ are each independently hydrogen or $(C_1-C_6)$alkyl, preferably methyl. More preferably, $R^1$ is hydrogen or methyl and $R^2$ is hydrogen. More preferably, $R^1$ is methyl and $R^2$ is hydrogen.
Preferably, when $R^1$ is not hydrogen and $R^2$ is hydrogen, then the carbon atom bearing $R^1$ and $R^2$ is in the (R) configuration.
Preferably, $R^3$ is hydrogen, halogen, or $C_1-C_4$ alkyl. More preferably $R^3$ is hydrogen.
Preferably, $R^4$ is $(C_1-C_6)$alkyl or halo$(C_1-C_6)$alkyl. More preferably, $R^4$ is tert-butyl, trifluoromethyl or 2,2,2-trifluoro-1,1-dimethyl-ethyl.
Preferably, $R^6$ is hydroxy, hydroxymethyl or methoxy.
Preferably, $R^5$ is hydrogen, halogen, hydroxy, $(C_1-C_6)$alkyl or $(C_1-C_6)$alkoxy. More preferably, $R^5$ is hydrogen, $(C_1-C_6)$alkyl or $(C_1-C_6)$alkoxy. More preferably, $R^5$ is hydrogen, methyl or methoxy.
Preferably, $R^7$ is hydrogen, halogen, hydroxy, $(C_1-C_6)$alkyl or $(C_1-C_6)$alkoxy. More preferably, $R^7$ is hydrogen or halogen. More preferably, $R^7$ is hydrogen, fluoro, chloro or bromo.
Preferably, $R^5$ is methyl, $R^6$ is $CH_2OH$, hydroxy or methoxy and $R^7$ is chloro, fluoro or bromo.
Preferably, $R^5$ is methyl, $R^6$ is hydroxy or methoxy and $R^7$ is chloro.
Preferably, $R^5$ is methoxy, $R^6$ is hydroxy and $R^7$ is chloro, fluoro or bromo.
Preferably, $R^5$ is methoxy, $R^6$ is hydroxy and $R^7$ is chloro.
Preferably, $R^5$ is hydrogen, $R^6$ is —$CH_2OH$ and $R^7$ is hydrogen.
Preferably, $R^5$ is methoxy, $R^6$ is hydroxy and $R^7$ is hydrogen.

Preferred compounds of the invention include those in which each variable in formula (I) is selected from the preferred groups for each variable.

Specific preferred compounds of the invention are those listed in the Examples section below and the pharmaceutically acceptable salts and solvates thereof.

The compounds of formula (I), being VR1 antagonists, are potentially useful in the treatment of a range of disorders, particularly the treatment of pain, including chronic pain, acute pain, nociceptive pain, neuropathic pain, inflammatory pain, post herpetic neuralgia, neuropathies, neuralgia, diabetic neuropathy, HIV-related neuropathy, nerve injury, rheumatoid arthritic pain, osteoarthritic pain, burns, back pain, visceral pain, cancer pain, dental pain, headache, migraine, carpal tunnel syndrome, fibromyalgia, neuritis, sciatica, pelvic hypersensitivity, pelvic pain and menstrual pain; bladder disease, such as urinary incontinence, lower urinary tract symptoms, micturition disorder, renal colic and cystitis; inflammation, such as burns, rheumatoid arthritis and osteoarthritis; neurodegenerative disease, such as stroke, post stroke pain and multiple sclerosis; diseases of the respiratory tree that have a contribution to symptoms or pathology arising from the sensory afferent nervous system, such as cough, bronchoconstriction, irritation, inflammation and other pathways in diseases of the lower airway such as asthma and chronic obstructive pulmonary disease (COPD) as well as those of the upper airway, such as allergic rhinitis and chronic sinusitis; gastrointestinal disorders, such as gastroesophageal reflux disease (GERD), dysphagia, ulcer, irritable bowel syndrome (IBS), inflammatory bowel disease (IBD), colitis and Crohn's disease; ischemia, such as cerebrovascular ischemia and acute cerebral ischemia; emesis, such as cancer chemotherapy-induced emesis; diabetes and obesity, or the like in mammals, especially humans. The treatment of pain is a preferred use, particularly inflammatory pain Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a heightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertabral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain includes functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:

pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;

heart and vascular pain, including pain caused by angina, myocardical infarction, mitral stenosis, pericarditis, Raynaud's phenomenon, scleredoma and skeletal muscle ischemia;

head pain, such as migraine (including migraine with aura and migraine without aura), cluster headache, tension-type headache mixed headache and headache associated with vascular disorders; and orofacial pain, including dental pain, otic pain, burning mouth syndrome and temporomandibular myofascial pain.

Urinary incontinence (any condition in which there is an involuntary leakage of urine), includes stress urinary incontinence, urge urinary incontinence and mixed urinary incontinence, overactive bladder with associated urinary incontinence, enuresis, nocturnal enuresis, continuous urinary incontinence, and situational urinary incontinence such as incontinence during sexual intercourse.

Lower urinary tract symptoms comprise three groups of urinary symptoms, which may be defined as storage (irritative), voiding (obstructive) and post-micturition symptoms. Storage symptoms comprise urgency, frequency, nocturia, urgency incontinence and stress incontinence, which can be associated with overactive bladder (OAB) and benign prostatic hyperplasia (BPH). Voiding symptoms comprise hesitancy, poor flow, intermittency, straining and dysuria. Post-micturition symptoms comprise terminal dribbling, post-void dribbling and a sense of incomplete emptying.

Over Active Bladder (OAB) is defined as urgency, with or without urge incontinence, usually with frequency and nocturia [Abrams et al., Neurourology and Urodynamics 21:167-178 (2002)]. Prevalence of OAB in men and women is similar, with approximately 16% of the population of the USA suffering from the condition [Stewart et al, Prevalence of Overactive Bladder in the United States: Results from the NOBLE Program; Abstract Presented at the $2^{nd}$ International Consultation on Incontinence, July 2001, Paris, France]. OAB includes OAB Wet and OAB Dry. The terms OAB Wet and OAB Dry describe OAB patients with or without urinary incontinence, respectively. Until recently, the cardinal symptom of OAB was believed to be urinary incontinence. However, with the advent of the new terms this is clearly not meaningful for the large number of sufferers who are not incontinent (i.e. OAB Dry patients). Thus, a recent study from Liberman et al ['Health Related Quality of Life Among Adults with Symptoms of Overactive Bladder: Results From A US Community-Based Survey'; Urology 57(6), 1044-1050, 2001] examined the impact of all OAB symptoms on the quality of life of a community-based sample of the US population. This study demonstrated that individuals suffering from OAB without any demonstrable loss of urine have an impaired quality of life when compared with controls.

BPH is a chronically progressive disease that can lead to complications such as acute urinary retention, recurrent urinary tract infections, bladder stones and renal dysfunction. The prevalence and average severity of LUTS associated with BPH in men increases with age. BPH leads to an increase in prostate volume, creating urethral and bladder outflow obstruction as well as secondary changes in bladder function. The effects of this are manifested by both storage (irritative) and voiding (obstructive) symptoms.

The present invention provides a pharmaceutical composition including a compound of formula (I), or a pharmaceutically acceptable salt or solvate thereof, together with a pharmaceutically acceptable excipient. The composition is preferably useful for the treatment of the disease conditions defined above.

The present invention further provides a compound of formula (I), or a pharmaceutically acceptable salt or solvate thereof, for use as a medicament. The present invention further provides a compound of formula (I), or a pharmaceutically acceptable salt or solvate thereof, for use in the treatment of a disease condition defined above.

Further, the present invention provides a method for the treatment of the disease conditions defined above in a mammal, preferably a human, which includes administering to said mammal a therapeutically effective amount of a compound of formula (I), or a pharmaceutically acceptable salt or solvate thereof.

Yet further, the present invention provides the use of a compound of formula (I), or a pharmaceutically acceptable salt or solvate thereof, in the manufacture of a medicament for the treatment of the disease conditions defined above.

Yet further, the present invention provides a combination of a compound of the formula (I), or a pharmaceutically acceptable salt or solvate thereof, and another pharmacologically active agent.

In this specification, especially in "General Synthesis" and "Examples", the following abbreviations can be used:
BEP 2-bromo-1-ethylpyridinium tetrafluoroborate
BOP benzotriazol-1-yloxy-tris(dimethylamino)phosphonium hexafluorophosphate
CDI 2-chloro-1,3-dimethylimidazolinium chloride
DCC dicyclohexylcarbodiimide
DCM dichloromethane
DME 1,2-dimethoxyethane, dimethoxyethane
DMF N,N-dimethylformamide
DMSO dimethyl sulfoxide
EDC 1-ethyl-3-(3'-dimethylaminopropyl)carbodiimide hydrogen chloride
$Et_2O$ diethylether
EtOAc ethyl acetate
EtOH ethanol
HBTU 2-(1H-benzenotriasol-1-yl)-1,1,3,3-tetramethyluronium hexafluorophosphate
HOBt 1-hydroxybenzotriazole
Me methyl
MeOH methanol
NMP N-methyl-2-pyrroliidone
THF tetrahydrofuran
TFA trifluoroacetic acid
TMS trimethyl silane
General Synthesis Scheme 1:

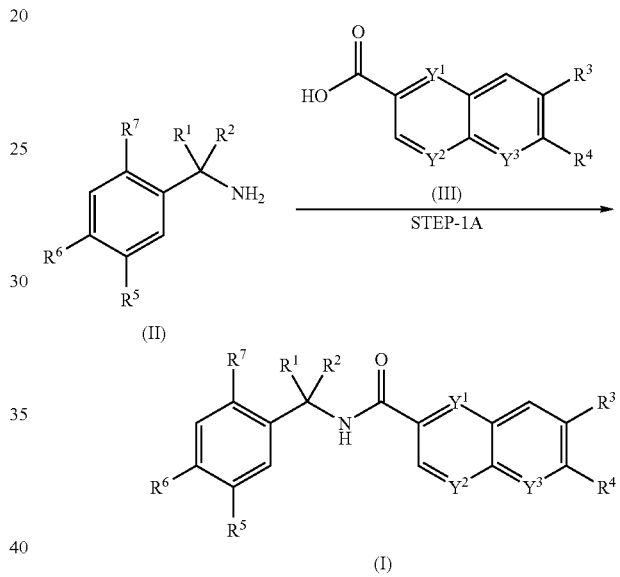

This illustrates the preparation of compounds of formula (I).

Step 1A: In this Step, amide compounds of formula (I) can be prepared by the coupling reaction of an amine compound of formula (II) with an acid compound of formula (III) in the presence or absence of a coupling reagent in an inert solvent. Suitable coupling reagents are those typically used in peptide synthesis including, for example, diimides (e.g., DCC, EDC, 2-ethoxy-N-ethoxycarbonyl-1,2-dihydroquinoline, BEP, CDI, BOP, diethyl azodicarboxylate-triphenylphosphine, diethylcyanophosphate, diethylphosphorylazide, 2-chloro-1-methylpyridinium iodide, N,N'-carbonyldiimidazole, benzotriazole-1-yl diethyl phosphate, ethyl chloroformate or isobutyl chloroformate). The reaction can be carried out in the presence of a base such as HOBt, N,N-diisopropylethylamine, N-methylmorpholine or triethylamine. The amide compound of formula (I) can be formed via an acylhalide, which can be obtained by the reaction with halogenating agents such as oxalylchloride, phosphorus oxychloride or thionyl chloride. The reaction is normally and preferably carried out in the presence of a solvent. There is no particular restriction on the nature of the solvent to be employed, provided that it has no adverse effect on the reaction or on the reagents involved and that it can dissolve the reagents, at least to some extent. Examples of suitable solvents include acetone; nitromethane; N,N-dimethylformamide; NMP; sulfolane; dimethylsulfoxide; 2-butanone; acetonitrile; halogenated hydrocarbons such as dichloromethane, dichloroethane or chloroform; and ethers such as THF or 1,4-dioxane. The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 100° C., more preferably from about 0° C. to 60° C. The time required for the reaction can also vary widely, depending on many factors, notably the reaction temperature and the nature of the reagents and solvent employed. However, provided that the reaction is effected under the preferred conditions outlined above, a period of 5 minutes to 1 week, more preferably 30 minutes to 24 hours, will usually suffice.

Scheme 2:

When $R^6$ is hydroxy, a compound of formula (I) may be prepared from a corresponding alkoxy compound of formula (I) by dealkylation, as illustrated by the following process, wherein R' is $(C_1-C_6)$alkyl.

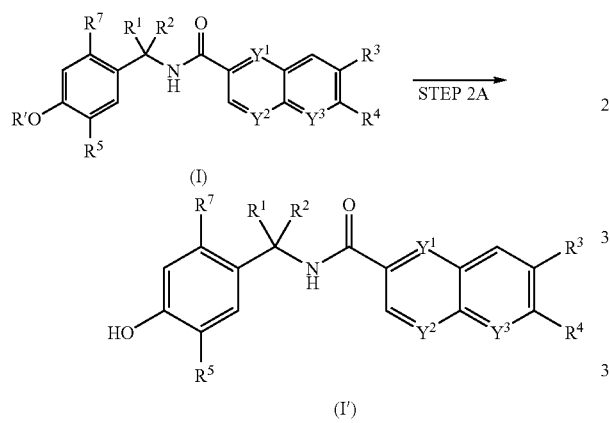

Step-2A

In this Step, a compound of formula (I') can be prepared by dealkylation of a compound of formula (I) with a dealkylating agent in an inert solvent. Examples of suitable dealkylating agents include: boron halides such as boron tribromide or boron trichloride; and hydrogen halides, such as hydrogen bromide. Preferred reaction inert solvents include, for example: halogenated hydrocarbons such as dichloromethane, 1,2-dichloroethane, chloroform or carbon tetrachloride; and acetic acid. Reaction temperatures are generally in the range of from −100 to 200° C., preferably in the range of from −80° C. to 80° C. Reaction times are, in general, from 1 minute to a day, preferably from 1 hour to 10 hours.

The amine of formula (II) can be easily prepared by the man skilled in the art. Schemes 3 to 8 represents generic processes useful for the preparation of compounds of formula (II).

Scheme 3:

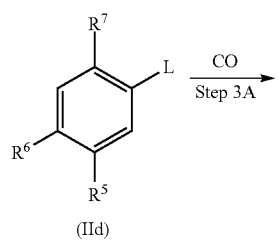

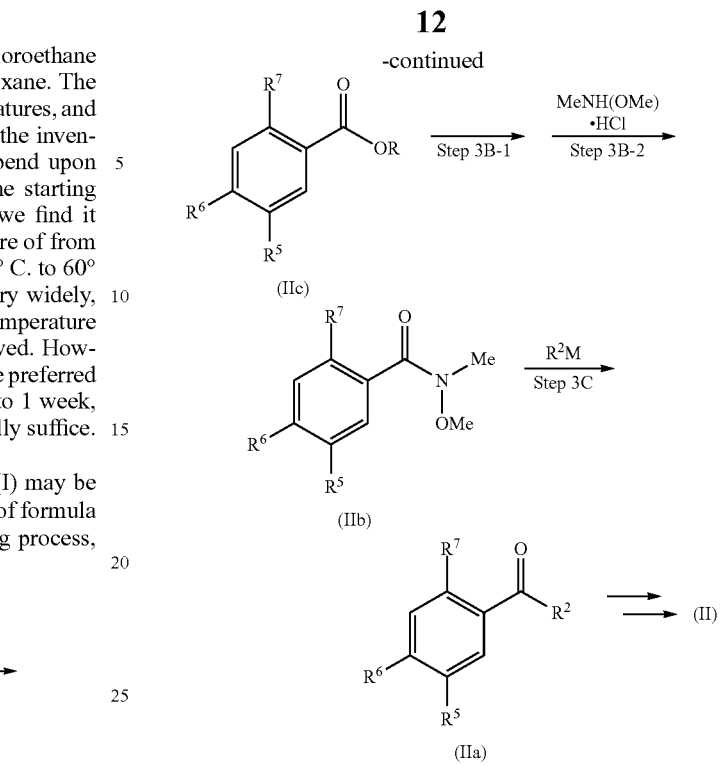

wherein, M is a methal, such as lithium, or a metal halide, such as MgZ wherein Z is a halogen; and L is a suitable leaving group;

Step 3A: In this Step, a compound of formula (IIc) may be prepared by reacting a compound of formula (IIb) with carbon monoxide and alcohol (e.g. MeOH, EtOH) in the presence of a catalyst and/or base in an inert solvent. Examples of suitable catalysts include: palladium reagents, such as palladium acetate or palladium dibenzylacetone. Examples of suitable bases include N,N-diisopropylethylamine, N-methylmorpholine or triethylamine. If desired, this reaction may be carried out in the presence or absence of an additive such as 1,1'-bis(diphenylphosphino)ferrocene, triphenylphosphine or 1,3-bis-(diphenylphosphino)propane (DPPP). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include acetone; nitromethane; DMF; sulfolane; DMSO; NMP; 2-butanone; acetonitrile; halogenated hydrocarbons such as DCM, dichloroethane or chloroform; or ethers, such as THF or 1,4-dioxane. The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 150° C., more preferably from about 50° C., to 80° C. The time required for the reaction may also vary widely, depending on many factors, notably the reaction temperature and the nature of the reagents and solvent employed. However, provided that the reaction is effected under the preferred conditions outlined above, a period of 30 minutes to 24 hours, more preferably 1 hour to 10 hours, will usually suffice.

Step 3B-1: In this Step, an acid compound may be prepared by hydrolysis of the compound of formula (IIc) in a solvent.

The hydrolysis may be carried out by conventional procedures. In a typical procedure, the hydrolysis is carried out under the basic condition in the presence of water, suitable bases include, for examples, sodium hydroxide, potassium hydroxide or lithium hydroxide. Suitable solvents include, for example, alcohols such as MeOH, EtOH, propanol, butanol, 2-methoxyethanol or ethylene gylcol; ethers such as THF, DME or 1,4-dioxane; amides such as DMF or hexamethylphosphorictriamide; or sulfoxides such as DMSO. This reaction may be carried out at a temperature in the range from −20 to 100° C., usually from 20° C. to 65° C. for 30 minutes to 24 hours, usually 60 minutes to 10 hours. The hydrolysis may also be carried out under acidic conditions, e.g. in the presence of hydrogen halides such as hydrogen chloride and hydrogen bromide; sulfonic acids such as p-toluenesulfonic acid and benzenesulfonic acid; pyridium p-toluenesulfonate; and carboxylic acids such as acetic acid and trifluoroacetic acid. Suitable solvents include, for example, alcohols such as MeOH, EtOH, propanol, butanol, 2-methoxyethanol, and ethylene gylcol; ethers such as THF, DME and 1,4-dioxane; amides such as DMF and hexamethylphosphorictriamide; and sulfoxides such as DMSO. This reaction may be carried out at a temperature in the range from −20 to 100° C., usually from 20° C. to 65° C. for 30 minutes to 24 hours, usually 60 minutes to 10 hours.

Step 3B-2: In this step, an amide compound of formula (IIb) can be prepared from a compound of 3B-1 by the same procedure as Step 1A.

Step 3C: In this Step, a compound of formula (IIa) can be prepared by reaction of a compound of formula (IIb) with an organometallic reagent $R^2M$. $R^2M$ can be prepared by reaction of a halide compound of $R^2$. For example, $R^2M$, in which M represents MgZ, can be generated with stirring Mg and $R^2Z$, dibromoethane and $I_2$ at a temperature in the range of between 30-80° C. This reaction may be carried out in the presence of an organometallic reagent or a metal. Examples of suitable organometallic reagents include alkyllithiums such as n-butyllithium, sec-butyllithium or tert-butyllithium; aryllithiums such as phenyllithium or lithium naphtilide. Examples of suitable metal include magnesium. Preferred inert solvents include, for example, hydrocarbons such as hexane; ethers such as diethyl ether, diisopropyl ether, DME, THF or 1,4-dioxane; or mixtures thereof. Reaction temperature is generally in the range of −100 to 50° C., preferably in the range of from −100° C. to room temperature. Reaction time is, in general, from 1 minute to a day, preferably from 1 hour to 10 hours.

A compound of formula (IIa) may be converted to a compound of formula (II) by any one of routes 1-4 below.

When $R^2$ is hydrogen, a compound of formula (II) may be prepared from a compound of formula (IIa) as illustrated by Route 1.

Route 1

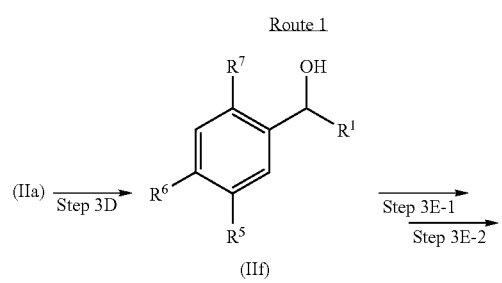

Step 3D: In this Step, a compound of formula (IIf) can be prepared by reduction of a compound of formula (IIa). The reduction of the carbonyl group of compound (IIa) may be carried out by conventional procedures. In a typical procedure, the reduction is carried out by treatment with lithium aluminum hydride, lithium borohydride or boran in a suitable inert solvent. Suitable solvents include, for example, ethers such as THF, DME or 1,4-dioxane. This reaction may be carried out at a temperature in the range from −20 to 100° C., usually from 20° C. to 65° C. for 30 minutes to 24 hours, usually 60 minutes to 10 hours. An alternative reduction procedure may be carried out by treatment with a reduction agent such as $BH_3Me_2S$ complex having (R)-3,3-diphenyl-1-methylpyrrolidino[1,2,C]-1,3,2-oxazaborole as a ligand. Suitable inert solvents include THF. The reaction may be carried out at a temperature of −10° C., for 30 minutes to 24 hours, usually 60 minutes to 10 hours.

Step 3E-1: In this Step, a compound of formula (IIf) may be converted to a compound with a leaving group under conditions known to those skilled in the art. For example, the hydroxy group of the compound of formula (IIf) may be converted to the chloride using a chlorinating agent, e.g. thionyl chloride, oxalyl chloride in the presence or absence of an inert solvent, e.g. halogenated hydrocarbons such as methylene chloride, chloroform, carbon tetrachloride or 1,2-dichloroethane; ethers such as diethyl ether, diisopropyl ether, THF or 1,4-dioxane; DMF or DMSO. For another example, the hydroxy group of the compound of formula (IIf) may be converted to the sulfonate group using a sulfonating agent, e.g. para-toluenesulfonyl chloride, para-toluenesulfonic anhydride, methanesulfonyl chloride, methanesulfonic anhydride, trifluoromethanesulfonic anhydride in the presence of, or absence of a base, e.g. an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride, or an amine such as triethylamine, tributylamine, diisopropylethylamine, pyridine or dimethylaminopyridine in the presence or absence of an inert solvent, e.g. aliphatic hydrocarbons, such as hexane, heptane or petroleum ether; aromatic hydrocarbons, such as benzene, toluene, o-dichlorobenzene, nitrobenzene, pyridine or xylene; halogenated hydrocarbons such as methylene chloride, chloroform, carbon tetrachloride or 1,2-dichloroethane; ethers such as diethyl ether, diisopropyl ether, THF or 1,4-dioxane; DMF or DMSO.

Step 3E-2: A compound of formula (IIe) may be prepared by azido introduction. The compound obtained in the Step 3E-1 may be treated with diphenylphosphoryl azide (DPPA), sodiumazide, or $HN_3$ in the presence of a dialkyl azodicarboxylate such as diethyl azodicarboxylate (DEAD) and a phosphine reagent such as triphenylphosphine. Preferably, this reaction may be carried out in an inert solvent. Preferred inert solvents include, but are not limited to, THF, diethyl ether, DMF, benzene, toluene, xylene, o-dichlorobenzene, nitrobenzene, DCM, 1,2-dichloroethane or DME; or mixtures thereof. The reduction may be carried out in the presence of a suitable reducing agent such as lithium aluminum

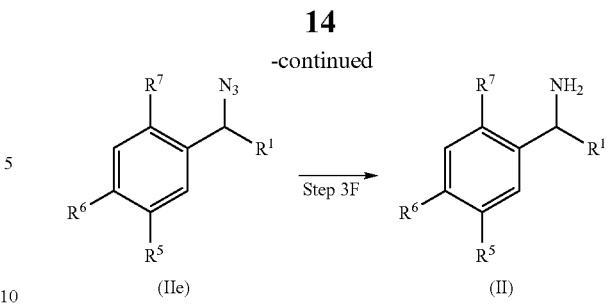

hydride, sodium borohydride, triethyl phosphite, triphenylphosphine, zinc, dibutyl tinhydride or diboran in an inert solvent selected from, but not limited to, THF, diethyl ether, MeOH, and EtOH. If desired, the reaction may be carried out under acidic conditions in the presence of hydrochloric acid or acetic acid. Reaction temperature is generally in the range of −100 to 250° C., preferably in the range of 0° C. to the reflux temperature, but if necessary, lower or higher temperature can be employed. Reaction time is, in general, from 1 minute to a day, preferably from 20 minutes to 5 hours, however shorter or longer reaction times, if necessary, can be employed.

Step 3F: In this Step, a compound of formula (II) can be prepared by reduction of an azide compound of formula (IIe) with a reducing agent. This reaction may be carried out in the presence of a suitable reducing agent such as diboran, boranmethyl sulfide complex, or lithium aluminum hydride in an inert solvent such as THF or diethyl ether. The reaction may also be carried out in similar conditions to those described in Step 2D above. Reaction temperature is generally in the range of −100 to 250° C., preferably in the range of 0° C. to the reflux temperature, but if necessary, lower or higher temperature can be employed. Reaction time is, in general, from 1 minute to a day, preferably from 20 minutes to 5 hours, however shorter or longer reaction times, if necessary, can be employed. The reduction may also be carried out under known hydrogenation conditions such as in the presence of a metal catalyst such as Raney nickel catalysts in the presence or absence of hydrazine, palladium catalysts or platinum catalysts under hydrogen atmosphere. This reaction may be carried out in an inert solvent such as MeOH, EtOH, or THF, in the presence or absence of hydrogen chloride. If necessary, this reduction may be carried out under pressure in the range from about 0.5 to 10 kg/cm$^2$, preferably in the range from 1 to 6 kg/cm$^2$. Reaction temperature is generally in the range of −100° C. to 250° C., preferably in the range of 0° C. to the reflux temperature, but if necessary, lower or higher temperature can be employed. Reaction time is, in general, from 1 minute to 2 days, preferably from 20 minutes to 24 hours. Alternatively, when R$^2$ is hydrogen, a compound of formula (II) may be prepared form a compound of formula (IIa) as illustrated by Route 2.

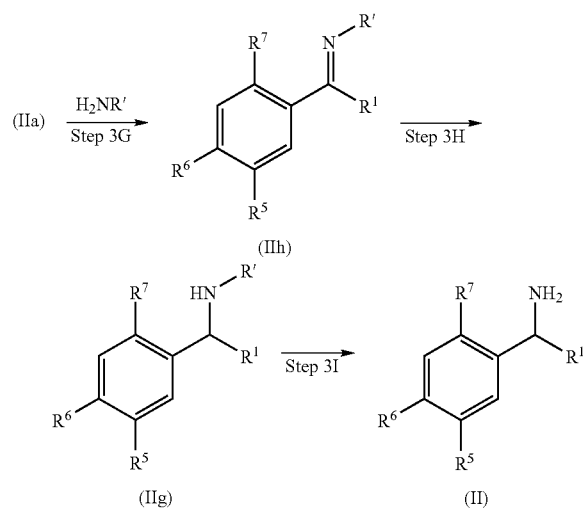

wherein R' is t-butylsulfinyl, phenethyl, NH$_2$, benzyl or diphenylmethyl.

Step 3G: In this step, a compound of formula (IIh) can be prepared by coupling reaction of a compound of formula (IIa) with an amine of formula R'NH$_2$ in the presence of a dehydrating reagent and/or HCl-MeOH and/or Lewis Acid. A preferred dehydrating reagent includes sodium sulfate, magnesium sulfate, calcium sulfate or methylformate. Examples of suitable solvents include THF; 1,4-dioxane; DMF; acetonitrile; alcohols such as MeOH or EtOH; halogenated hydrocarbons such as DCM, 1,2-dichloroethane, chloroform or carbon tetrachloride; or acetic acid. Reaction temperature is generally in the range of 0 to 200° C., preferably in the range of from 100° C. to 140° C. Reaction time is, in general, from 1 minute to a day, preferably from 5 minutes to 1 hour. If necessary, microwave conditions are applied to the reaction.

Step 3H: In this step, a compound of formula (IIg) can be prepared by reduction of a compound of formula ((IIh) with a reducing agent. This reaction may be carried out in the presence of a suitable reducing agent such as diboran, boranmethyl sulfide complex, sodium borohydride, lithium borohydride, sodium borohydride, or lithium aluminum hydride in an inert solvent selected from THF and diethyl ether. Reaction temperature is generally in the range of −100 to 250° C., preferably in the range of 0° C. to the reflux temperature, but if necessary, lower or higher temperature can be employed. Reaction time is, in general, from 1 minute to a day, preferably from 20 minutes to 5 hours, however shorter or longer reaction times, if necessary, can be employed. The reduction may also be carried out under known hydrogenation conditions such as in the presence of a metal catalyst such as Raney nickel catalysts in the presence or absence of hydrazine, palladium catalysts or platinum catalysts under hydrogen atmosphere. This reaction may be carried out in an inert solvent such as MeOH, EtOH, and THF in the presence or absence of hydrogen chloride. If necessary, this reduction may be carried out under pressure in the range from about 0.5 to 10 kg/cm$^2$, preferably in the range from 1 to 6 kg/cm$^2$. Examples of suitable solvents are similar to those mentioned in Step 3G. Reaction temperature is generally in the range of −100° C. to 250° C., preferably in the range of 0° C. to the reflux temperature, but if necessary, lower or higher temperature can be employed. Reaction time is, in general, from 1 minute to 2 days, preferably from 20 minutes to 24 hours.

Step 3I: In this Step, a compound of the formula (II) can be prepared by deprotection and/or salt formation of a compound of formula (IIg) under acidic conditions in an inert solvent using a method of Journal of American Chemical Society, 1999, 121, 268-269 by D. Cogan et. al. Suitable acids include, for example, but not limited to hydrogen chloride, hydrogen bromide, trifluoromethane sulfonic acid, acetic acid or p-toluenesulfonic acid. The reaction may be also carried out under known hydrogenation conditions such as in the presence of a metal catalyst such as palladium-carbon catalyst or platinum catalysts under hydrogen atmosphere. This reaction may be carried out in an inert solvent such as MeOH, EtOH, and THF in the presence or absence of hydrogen chloride. If necessary, this reduction may be carried out under pressure in the range from about 0.5 to 10 kg/cm$^2$, preferably in the range from 1 to 6 kg/cm$^2$. Reaction temperature is generally in the range of −100° C. to 250° C., preferably in the range of 0° C. to the reflux temperature, but if necessary, lower or higher temperature can be employed. Reaction time is, in general, from 1 minute to 2 days, preferably from 20 minutes to 24 hours.

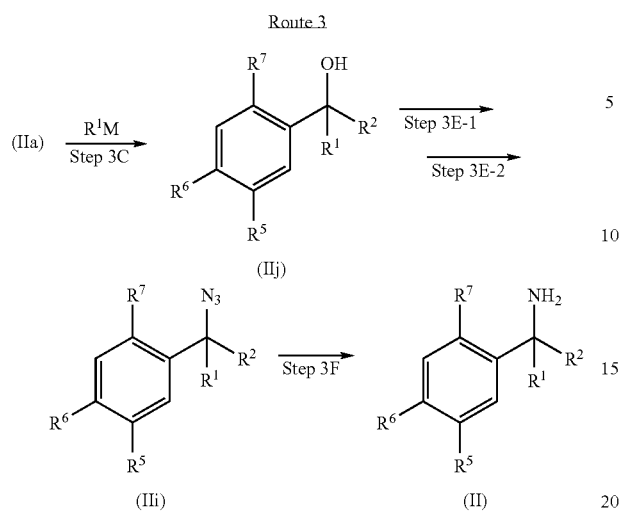

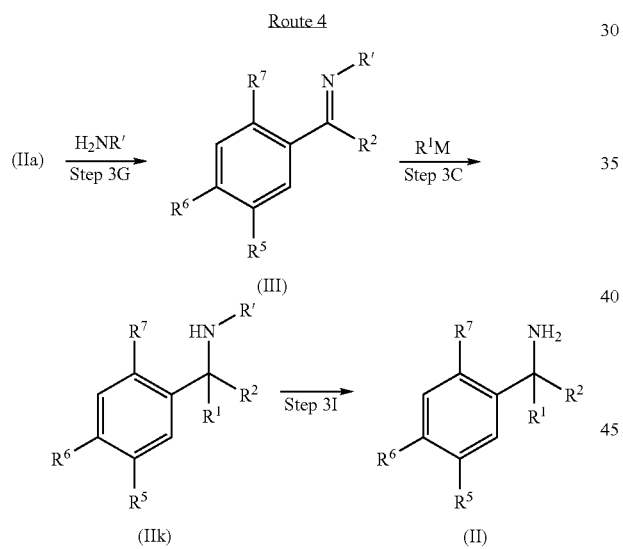

wherein M is a metal, such as lithium; or a metal halide, such as MgZ wherein Z is halogen.

In this route, a compound of the formula (II) can be prepared by the methods described in Step 3C, Step 3E-1 and E-2, and Step 3F above.

wherein R' is t-butylsulfinyl, phenethyl, $NH_2$, benzyl or diphenylmethyl; and $R^1M$ is a suitable alkylating agent including an alkyl metal, such as alkyl lithium; or a Grignard reagent, $R^1MZ$, wherein Z is halogen; or when $R^1$ is trifluoromethyl, then $R^1M$ may be trifluoromethyltrimethylsilane ($TMSCF_3$) in the presence of a catalytic fluoride source, such as CsF or tetralkylammonium fluoride.

In this route, a compound of the formula (II) can be prepared by the methods described in Step 3G, Step 3C and Step 3I above.

Scheme 3':

When $R^5$ is ($C_1$-$C_6$)alkoxy, $R^6$ is hydroxy, $R^7$ is hydrogen, $R^2$ is hydrogen and $R^1$ is methyl, a compound of formula (II) may be converted to a further compound of formula (II) by halogenation, according to the process illustrated below.

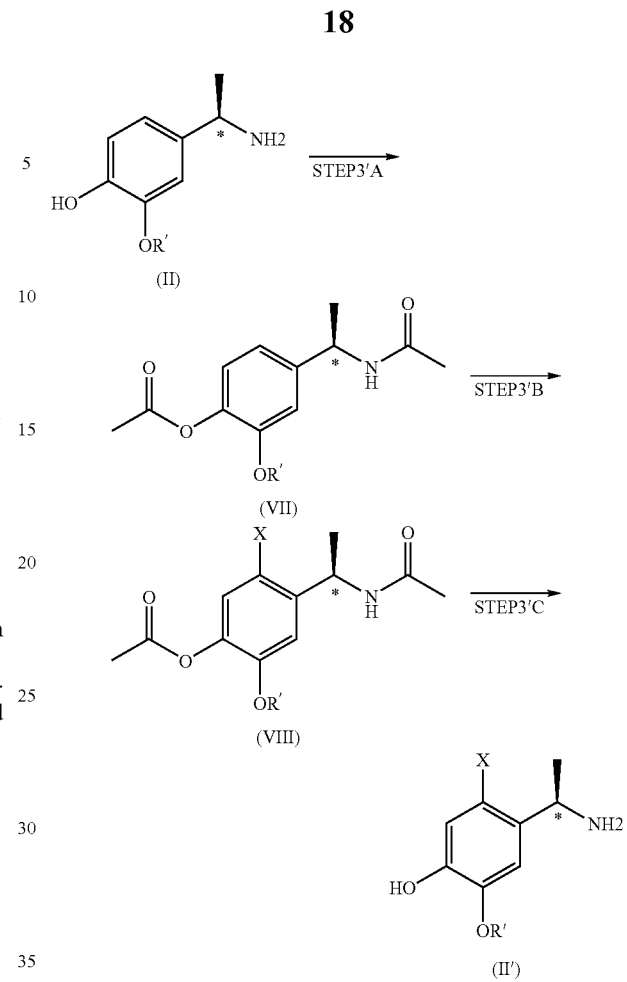

wherein X is halogen; R' is ($C_1$-$C_6$)alkyl; and * indicates the (R) configuration.

Step-3'A

In this Step, ¥ compound of the formula (VII) can be prepared by O-acetylation of a compound of formula (II) under various conditions in an inert solvent using a method of Protective Groups in Organic Synthesis (JOHN WILEY & SONS, Inc.); T. W. Greene and P. G. M. Wuts. Examples of suitable acetylating agents include acetic anhydride and acetyl chloride. This reaction may be carried out in an inert solvent such as ethers such as tetrahydrofuran, diethyl ether, 1,2-dimethoxyethane or 1,4-dioxane; halogenated hydrocarbons such as dichloromethane, 1,2-dichloroethane, chloroform or carbon tetrachloride; or pyridine under the presence or absence of base. Examples of suitable bases include trialkylamines such as triethylamine, diisopropylethylamine; pyridine and 4-dimethylaminopyridine. Reaction temperature is generally in the range of –20° C. to 150° C., preferably in the range of 0° C. to 100° C., but if necessary, lower or higher temperature can be employed. Reaction time is, in general, from 1 minute to 2 days, preferably from 20 minutes to 24 hours.

Step-3'B

In this Step, a compound of the formula (VIII) can be prepared by halogenation (electrophilic aromatic substitution reaction) of a compound of formula (VII) under various known conditions in an inert solvent. Preferred halogenation agents are selected from, for example, but not limited to: bromine, chlorine, iodide, N-halosuccinimide such as N-chlorosuccinimide, N-bromosuccinimide, and N-iodosuccinimide. Examples of suitable inert aqueous or non-aqueous organic solvents include: ethers, such as diethylether, tetrahydrofuran or 1,4-dioxane; halogenated hydrocarbons, such as dichloromethane, dichloroethane or chloroform; N,N-dialkylformamide such as N,N-dimethylformamide and acid solution such as acetic acid and trifluoroacetic acid; or mixtures thereof. The reaction can be carried out at a temperature in the range of from 20° C. to 150° C., preferably in the range of from 20° C. to 100° C. Reaction times are, in general, from 10 minutes to 4 days, preferably from 30 minutes to 24 hours.

Step-3'C

In this Step, a compound of the formula (II) can be prepared by deprotection and/or salt formation of a compound of formula (VIII) under acidic conditions in an inert solvent using a method of Protective Groups in Organic Synthesis (JOHN WILEY & SONS, Inc.); T. W. Greene and P. G. M. Wuts. Suitable acids include, for example, but not limited to hydrogen chloride, hydrogen bromide, trifluoromethane sulfonic acid, acetic acid or p-toluenesulfonic acid. The reaction can be carried out at a temperature in the range of from 20° C. to 150° C., preferably in the range of from 20° C. to 100° C. Reaction times are, in general, from 10 minutes to 4 days, preferably from 30 minutes to 24 hours.

Scheme 4:

When $R^5$ is methyl, $R^6$ is methoxy, $R^7$ is halogen, $R^2$ is hydrogen and $R^1$ is methyl, a compound of formula (II) may be prepared by the process illustrated below.

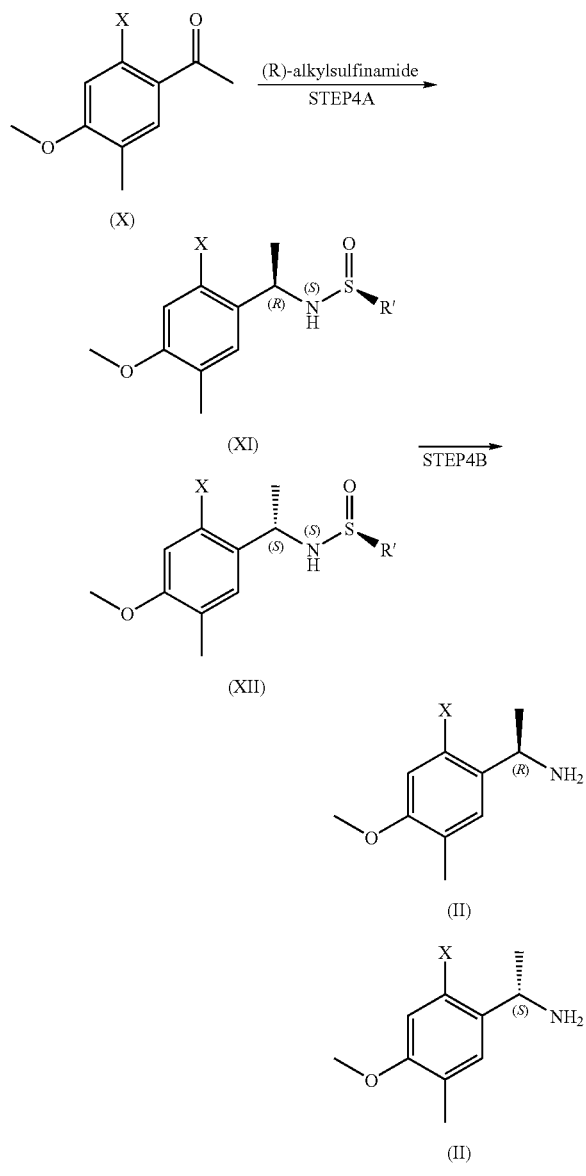

wherein R' is alkyl; and X is halogen, preferably chlorine.

Step 4A:

In this Step, a compound of formulae (XI) and (XII) can be prepared by dehydration and reduction of a compound of formula (X) and a suitable (R)-alkylsulfinylamide in the presence of a catalyst and reducing agent in an inert solvent. Dehydration is conducted in the presence of a dehydrating agent. Examples of suitable dehydrating agents include: hydrogen halides such as hydrogen chloride and hydrogen bromide; sulfonic acids such as p-toluenesulfonic acid and benzenesulfonic acid; sulfonylchlorides such as methansulfonylchloride and p-toluenesulfonylchloride; methoxycarbonylsulfamoyltriethylammonium hydroxide; p-toluenesulfonylisocyanate; and titanium(IV) ethoxide. Reaction temperatures are generally in the range of from 0 to 200° C., preferably in the range of from 50° C. to 100° C. Reaction times are, in general, from 1 minute to 48 hours, preferably from 12 hours to 24 hours. The reduction may be carried out in the presence of a suitable reducing agent in an inert solvent or without solvent. A preferred reducing agent is selected from, for example, but not limited to, sodium borohydride, lithium aluminium hydride, lithium borohydride, Fe, Sn or Zn. A preferred (R)-alkylsulfinylamide is (R)-(+)-2-methyl-2-propanesulfinylamide. Reaction temperatures are generally in the range of from −78° C. to room temperature, preferably in the range of from −70° C. to 0° C. Reaction times are, in general, from 1 minute to a day, preferably from 3 hours to 6 hours. Examples of suitable solvents include: tetrahydrofuran; 1,4-dioxane; N,N-dimethylformamide; acetonitrile; alcohols, such as methanol or ethanol; halogenated hydrocarbons, such as dichloromethane, 1,2-dichloroethane, chloroform or carbon tetrachloride; and acetic acid.

Step 4B:

In this Step, a compound of the formula (II) can be prepared by deprotection and/or salt formation of a compound of formula (XI) or (XII) under acidic conditions in an inert solvent using a method of Journal of American Chemical Society, 1999, 121, 268-269 by D. Cogan et. al. Suitable acids include, for example, but not limited to hydrogen chloride, hydrogen bromide, trifluoromethane sulfonic acid, acetic acid or p-toluenesulfonic acid. The reaction may be also carried out under known hydrogenation conditions such as in the presence of a metal catalyst such as palladium-carbon catalysts or platinum catalysts under hydrogen atmosphere. This reaction may be carried out in an inert solvent such as methanol, ethanol, and THF in the presence or absence of hydrogen chloride. If necessary, this reduction may be carried out under pressure in the range from about 0.5 to 10 kg/cm², preferably in the range from 1 to 6 kg/cm². Reaction temperature is generally in the range of −100° C. to 250° C., preferably in the range of 0° C. to the reflux temperature, but if necessary, lower or higher temperature can be employed. Reaction time is, in general, from 1 minute to 2 days, preferably from 20 minutes to 24 hours.

Scheme 5:

When $R^5$ is $(C_1-C_6)$alkyl, $R^6$ is hydroxy, $R^7$ is fluorine or chlorine, and $R^1$ and $R^2$ are both hydrogen, a compound of formula (II) may be prepared by the process illustrated below.

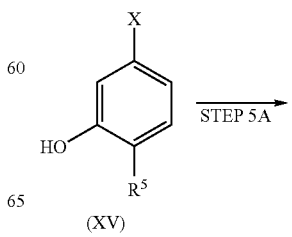

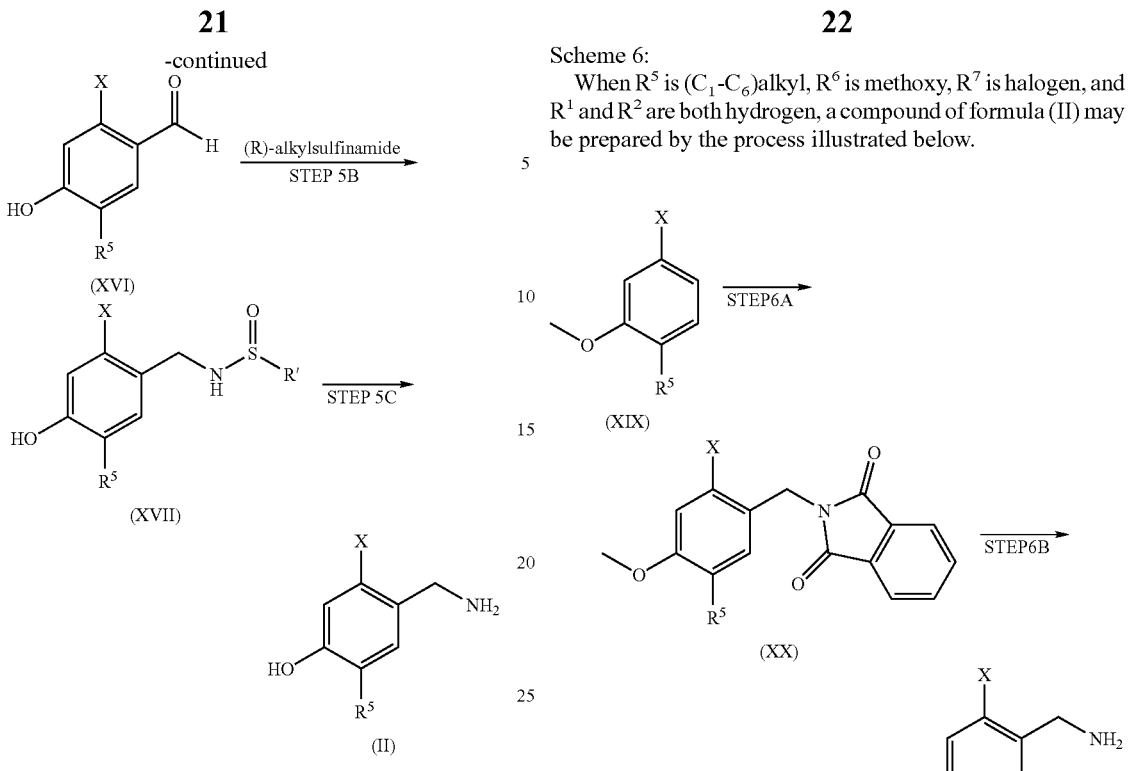

wherein X is fluorine or chlorine; and R' is alkyl.

Step 5A: A compound of formula (XVI) can be prepared by formylation reaction (electrophilic aromatic substitution reaction) from a compound of formula (XV) with formyl cation equivalents in a solvent. Examples of formyl cation equivalents include a combination of dichloromethylalkyl ether such as dichloromethylmethylether and dichloromethyl (n-butyl)ether with lewis acids such as tin tetrachloride, titanium tetrachloride and aluminium trichloride (Rieche method) and a combination of phosphorous oxychloride, thionyl chloride, oxalyl chloride and trifluoromethanesulfonic anhydride as activating reagents with N,N-dialkylformamides such as N,N-dimethylformamide, N-methylformamide and N-methylformanilide as reactants (Vilsmeier method); and a combination of hexamethylenetetramine (HMTA) with trifluoroacetic acid (Duff method). There is likewise no particular restriction on the nature of the catalysts used, and any catalysts commonly used in reactions of this type can equally be used here. This reaction can be carried out in the presence or absence of an inert solvent. Suitable solvents include, for example, ethers such as tetrahydrofuran, 1,2-dimethoxyethane or 1,4-dioxane; halogenated hydrocarbons such as dichloromethane, 1,2-dichloroethane, chloroform or carbon tetrachloride; or N,N-dialkylformamides, acetonitrile, and trifluoroacetic acid. The reaction can be carried out at a temperature of from −78° C. to 200° C., more preferably from −20° C. to 100° C. Reaction time is, in general, from 5 minutes to 48 hours, more preferably 30 minutes to 24 hours, will usually suffice.

Step 5B: In this step, a compound of formula (XVII) can be prepared by reduction of a compound of formula (XVI) and a suitable (R/S)-alkylsulfinylamide such as disclosed in step 4A.

Step 5C:

In this step, a compound of the formula (II) can be prepared from a compound of formula (XVII) by the method described in Step 4B above.

Scheme 6:

When $R^5$ is $(C_1-C_6)$alkyl, $R^6$ is methoxy, $R^7$ is halogen, and $R^1$ and $R^2$ are both hydrogen, a compound of formula (II) may be prepared by the process illustrated below.

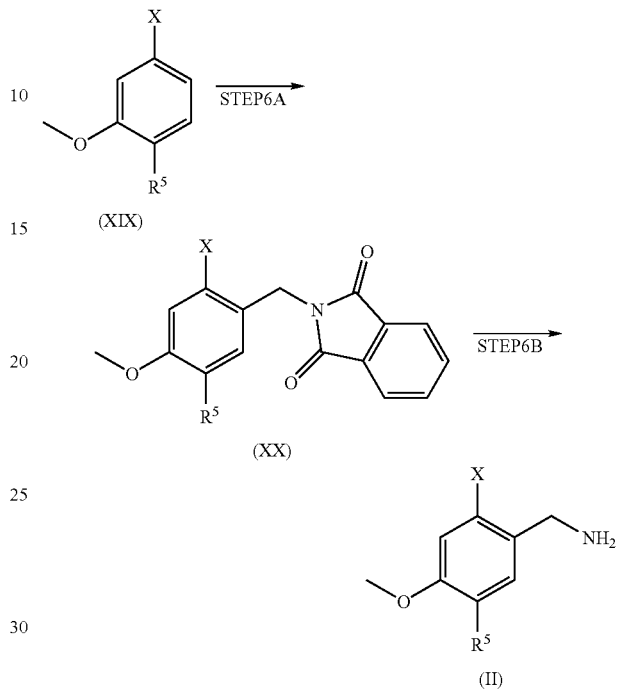

wherein X is halogen.

Step 6A:

In this Step, the compound of the formula (XX) can be prepared by imidomethylation (electrophilic aromatic substitution reaction) of the compound of formula (XIX) with O-phthalimidomethyl trichloroacetimidate and a catalytic amount of trimethylsilyl triflate (TMSOTf) [Tetrahedron 60 (2004) 4773-4780] in an inert solvent. Examples of suitable inert organic solvents include: ethers, such as diethylether, tetrahydrofuran or 1,4-dioxane; halogenated hydrocarbons, such as dichloromethane, dichloroethane or chloroform; N,N-dialkylformamide such as N,N-dimethylformamide; or mixtures thereof. The reaction can be carried out at a temperature in the range of from 20° C. to 150° C., preferably in the range of from 20° C. to 100° C. Reaction times are, in general, from 10 minutes to 4 days, preferably from 30 minutes to 24 hours.

Step 6B:

In this Step, a compound of the formula (II) can be prepared by deprotection of a compound of formula (XX) under various conditions in an inert solvent using a method of Protective Groups in Organic Synthesis (JOHN WILEY & SONS, Inc.); T. W. Greene and P. G. M. Wuts. Examples of suitable deprotecting agents are selected from, for example, but not limited to, hydrazine, phenylhydrazine and sodium sulfide. This reaction may be carried out in an inert solvent such as ethers such as tetrahydrofuran, diethyl ether, 1,2-dimethoxyethane or 1,4-dioxane, alcohols such as methanol, ethanol, 2-propanol; halogenated hydrocarbons such as dichloromethane, 1,2-dichloroethane, chloroform or carbon tetrachloride; and acidic solutions such as hydrochloric solution, acetic acid. Reaction temperature is generally in the range of 20° C. to 150° C., preferably in the range of 20° C. to 100° C., but if necessary, lower or higher temperature can be employed. Reaction time is, in general, from 1 minute to 2 days, preferably from 20 minutes to 24 hours.

Scheme 7:

When $R^5$ and $R^7$ are both hydrogen, $R^6$ is hydroxymethyl, $R^1$ is methyl and $R^2$ is hydrogen, a compound of formula (II) may be prepared by the process illustrated below.

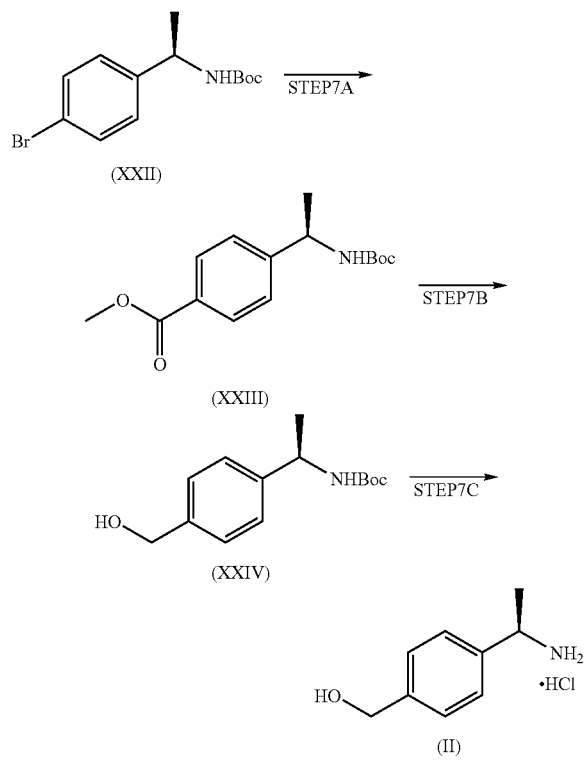

Step 7A: In this Step, the compound of formula (XXIII) may be prepared by carbon monoxide insertion reaction from the compound of formula (XXII) with carbon monoxide and alcohol (e.g. MeOH, EtOH) in the presence of a catalyst and/or base in an inert solvent. Examples of suitable catalysts include: palladium reagents, such as palladium acetate or palladium dibenzylacetone. Examples of suitable bases include N,N-diisopropylethylamine, N-methylmorpholine or triethylamine. If desired, this reaction may be carried out in the presence or absence of an additive such as 1,1'-bis(diphenylphosphino)ferrocene, triphenylphosphine or 1,3-bis-(diphenylphosphino)propane (DPPP). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include acetone; nitromethane; DMF; sulfolane; DMSO; NMP; 2-butanone; acetonitrile; halogenated hydrocarbons such as DCM, dichloroethane or chloroform; or ethers, such as THF or 1,4-dioxane. The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from –20° C. to 150° C., more preferably from about 50° C. to 80° C. The time required for the reaction may also vary widely, depending on many factors, notably the reaction temperature and the nature of the reagents and solvent employed. However, provided that the reaction is effected under the preferred conditions outlined above, a period of 30 minutes to 24 hours, more preferably 1 hour to 10 hours, will usually suffice.

Step 7B:

In this Step, the compound of formula (XXIV) can be prepared by reduction of the compound of formula (XXIII) in the presence of a reducing agent and a catalyst in an inert solvent. A preferred reducing agent is selected from, for example, but not limited to, sodium borohydride, lithium aluminium hydride, lithium borohydride, diisobutylaluminium hydride (DIBAL-H), Fe, Sn or Zn. Reaction temperatures are generally in the range of from –78° C. to 150° C., preferably in the range of from –70° C. to 100° C. Reaction times are, in general, from 1 minute to a day, preferably from 3 hours to 6 hours. Examples of suitable solvents include: ethers such as tetrahydrofuran, diethyl ether, 1,2-dimethoxyethane or 1,4-dioxane; alcohols such as methanol, ethanol, 2-propanol; halogenated hydrocarbons such as dichloromethane, 1,2-dichloroethane, chloroform or carbon tetrachloride; hydrocarbons, such as hexane, benzene, and toluene.

Step 7C

In this Step, the compound of formula (II) can be prepared from the compound of formula (XXIV) by deprotection and/or salt formation under various conditions in an inert solvent using a method of Protective Groups in Organic Synthesis (JOHN WILEY & SONS, Inc.); T. W. Greene and P. G. M. Wuts. Preferred acid conditions include, for example, but not limited to hydrogen chloride, hydrogen bromide, trifluoromethanesulfonic acid, trifluoroacetic acid, acetic acid or p-toluenesulfonic acid. Reaction temperature is generally in the range of –20° C. to 150° C., preferably in the range of 0° C. to the reflux temperature, but if necessary, lower or higher temperature can be employed. Reaction time is, in general, from 1 minute to 2 days, preferably from 20 minutes to 24 hours.

Scheme 8:

When $R^5$ is $(C_1-C_6)$alkyl, $R^6$ is hydroxymethytl, $R^7$ is fluorine or chlorine, $R^1$ is methyl and $R^2$ is hydrogen, a compound of formula (II) may be prepared by the process illustrated below.

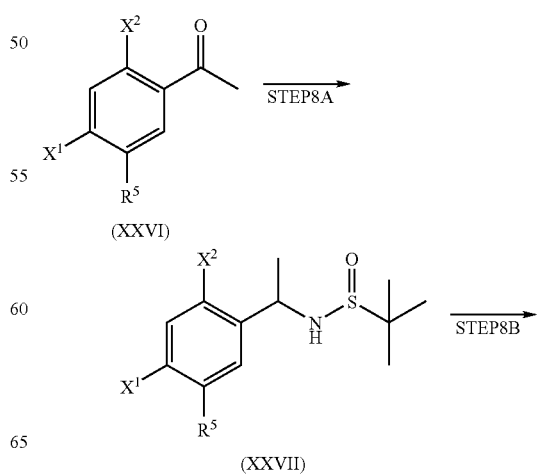

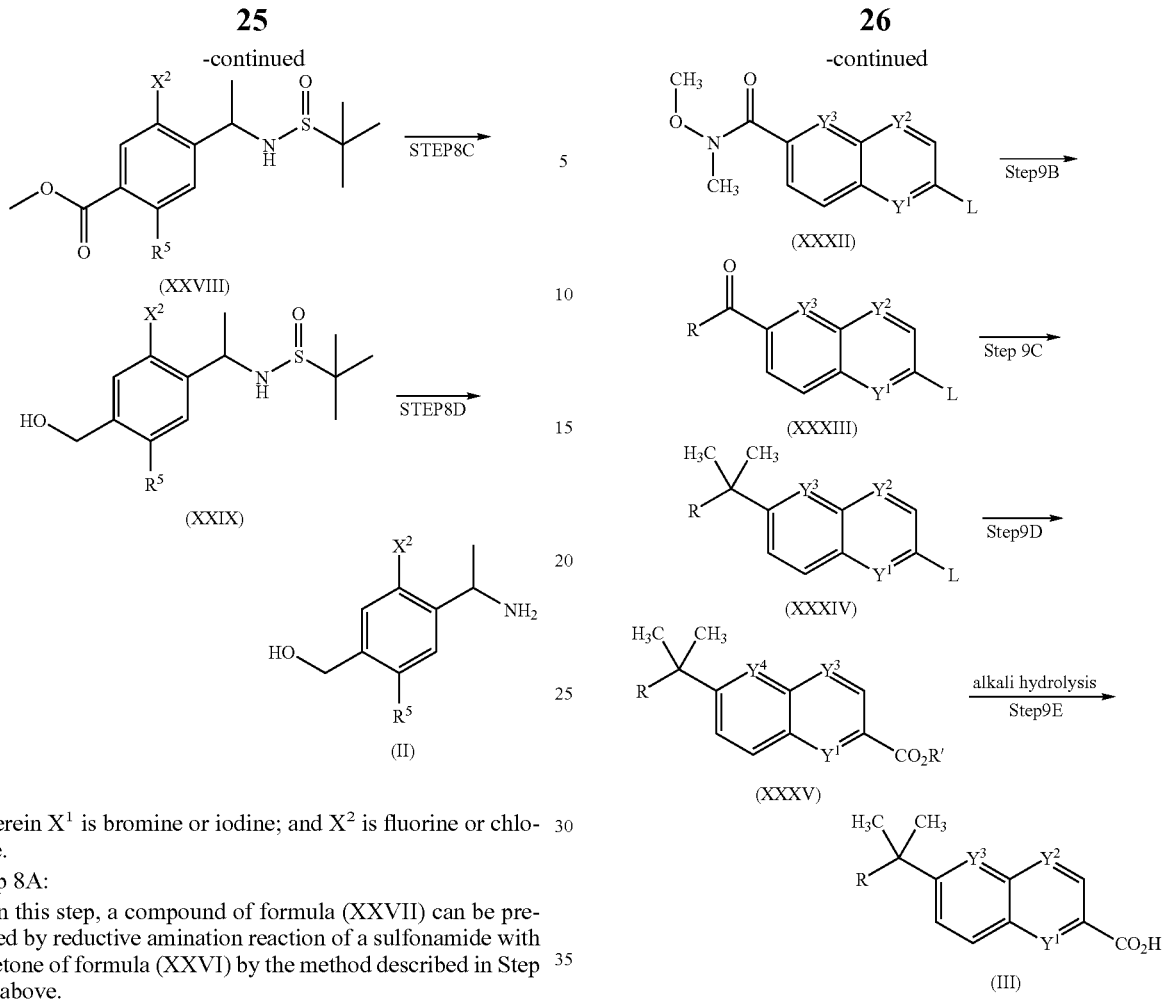

wherein $X^1$ is bromine or iodine; and $X^2$ is fluorine or chlorine.

Step 8A:

In this step, a compound of formula (XXVII) can be prepared by reductive amination reaction of a sulfonamide with a ketone of formula (XXVI) by the method described in Step 4A above.

Step 8B:

In this step, a compound of formula (XXVIII) can be prepared by carbon monoxide insertion reaction of a compound of formula (XXVII) by the method described in Step 7A above.

Step 8C:

In this step, a compound of formula (XXIX) can be prepared by reduction reaction of a compound of formula (XXVIII) by the method described in Step 7B above.

Step 8D:

In this step, a compound of the formula (II) can be prepared from a compound of formula (XXIX) by the method described in Step 4B above.

Schemes 9 to 15 provide examples of processes useful for the preparation of compounds of formula (III).

Scheme 9:

When $R^4$ is a 1,1-dimethylalkyl group, a compound of formula (III) may be prepared by the process illustrated below:

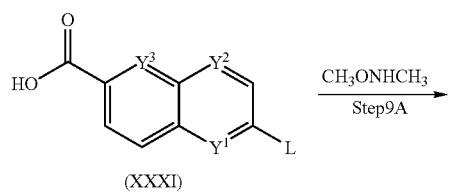

wherein L is a suitable leaving group; R is $(C_1-C_3)$alkyl, optionally substituted with halogen, hydroxy, or $(C_1-C_3)$ alkoxy; and R' is $(C_1-C_6)$alkyl.

Step 9A: In this Step, an amide compound of formula (XXXII) can be prepared from a compound of formula (XXXI) by the same procedure as Step 1A.

Step 9B:

In this Step, a compound of formula (XXXIII) can be prepared by reaction of a compound of formula (XXXII) with an organometallic reagent R-M, wherein M is a metal such as lithium, or MgZ wherein Z is a halogen. R-M can be prepared from a halide compound of R. For example, R-M, in which M represents MgZ, can be generated by stirring Mg, R⁻Z, dibromoethane and $I_2$ at a temperature in the range of between 30-80° C. This reaction may be carried out in the presence of an organometallic reagent or a metal. Examples of suitable organometallic reagents include alkyllithiums such as n-butyllithium, sec-butyllithium or tert-butyllithium; aryllithiums such as phenyllithium or lithium naphtilide. Examples of suitable metals include magnesium. Preferred inert solvents include, for example, hydrocarbons such as hexane; ethers such as diethyl ether, diisopropyl ether, DME, THF or 1,4-dioxane; or mixtures thereof. Reaction temperature is generally in the range of −100 to 50° C., preferably in the range of from −100° C. to room temperature. Reaction time is, in general, from 1 minute to a day, preferably from 1 hour to 10 hours.

Step 9C: In this Step, a compound of formula (XXXIV) can be prepared by an alkylation reaction of a compound of formula (XXXIII) with a geminal-alkylating reagent in an inert solvent. Examples of preferred alkylating agents include trialkylmetals such as trimethylaluminum, triethylaluminum; alkylmagnesium halides such as methylmagnesium bromide in the presence of an additive compound such as lithium bromide; dialkyltitanium halides such as dimethyltitanium dichloride prepared by dimethylzinc and titanium chloride. Most preferably, the alkylating agent is dimethyltitanium dichloride. Examples of preferred inert solvents for the reaction include halogenated hydrocarbons, such as DCM, 1,2-dichloroethane, chloroform or carbon tetrachloride; ethers, such as diethyl ether, diisopropyl ether, DME, THF and 1,4-dioxane; hydrocarbons, such as n-hexane, cyclohexane, benzene and toluene; or mixtures thereof. Reaction temperatures are generally in the range of from −100 to 200° C., preferably in the range of from −40° C. to 100° C. Reaction times are, in general, from 1 minute to a day, preferably from 1 hour to 10 hours.

Step 9D: In this Step, a compound of formula (XXXV) can be prepared from a compound of formula (XXXIV) by the same procedure as described in Step 3A.

Step 9E: In this Step, an acid compound of formula (III) may be prepared by hydrolysis of a compound of formula (XXXV) in a solvent. The hydrolysis may be carried out by conventional procedures. In a typical procedure, the hydrolysis is carried out under basic conditions in the presence of water. Suitable bases include, for example, sodium hydroxide, potassium hydroxide or lithium hydroxide. Suitable solvents include, for example, alcohols such as MeOH, EtOH, propanol, butanol, 2-methoxyethanol or ethylene gylcol; ethers such as THF, DME or 1,4-dioxane; amides such as DMF or hexamethylphosphorictriamide; or sulfoxides such as DMSO. This reaction may be carried out at a temperature in the range from −20 to 100° C., usually from 20° C. to 65° C. for 30 minutes to 24 hours, usually 60 minutes to 10 hours. The hydrolysis may also be carried out under acid conditions, e.g. in the presence of hydrogen halides such as hydrogen chloride and hydrogen bromide; sulfonic acids such as p-toluenesulfonic acid and benzenesulfonic acid; pyridium p-toluenesulfonate; and carboxylic acids such as acetic acid and trifluoroacetic acid. Suitable solvents include, for example, alcohols such as MeOH, EtOH, propanol, butanol, 2-methoxyethanol, and ethylene gylcol; ethers such as THF, DME and 1,4-dioxane; amides such as DMF and hexamethylphosphorictriamide; and sulfoxides such as DMSO. This reaction may be carried out at a temperature in the range from −20 to 100° C., usually from 20° C. to 65° C. for 30 minutes to 24 hours, usually 60 minutes to 10 hours.

Scheme 10:

When $Y^2$ is N and $Y^1$ and $Y^2$ are both CH, a compound of formula (III) may be prepared by the process illustrated below.

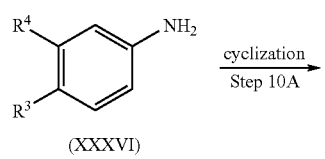

(XXXVI)

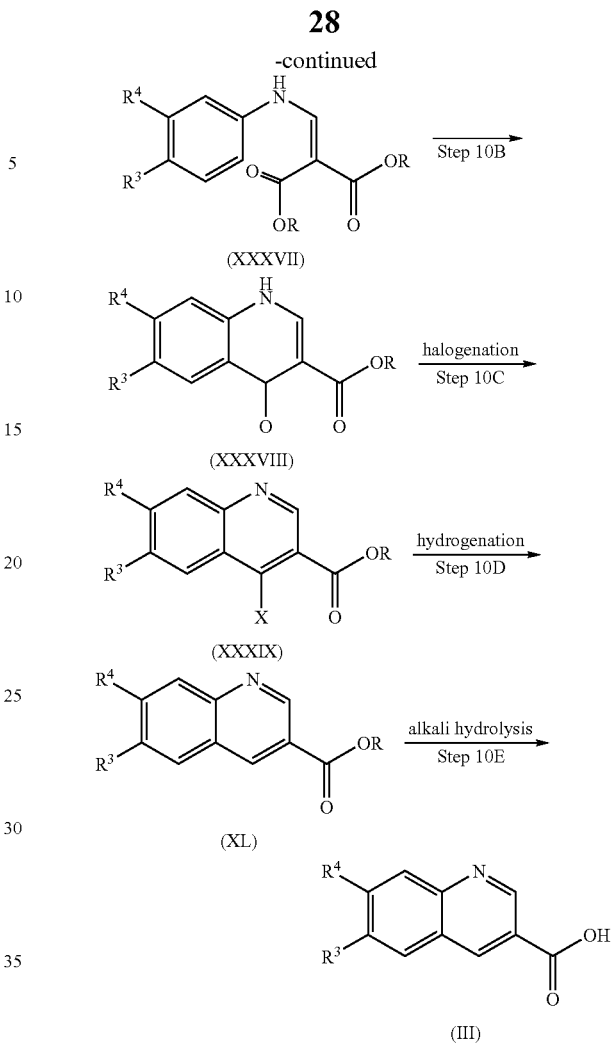

wherein R is $(C_1$-$C_6)$alkyl; and X is halogen, preferably chlorine.

Step 10A: In this Step, a compound of formula (XXXVII) can be prepared by N-substituted acrylation of a compound of formula (XXXVI) with dialkyl alkoxy methylenemalonate in a reaction inert solvent or without solvent. Examples of suitable solvents include alcohols such as MeOH, EtOH, propanol, butanol, 2-methoxyethanol, and ethylene glycol; ethers such as THF, DME, and 1,4-dioxane. The reaction can be carried out at a temperature in the range from 50° C. to 150° C. for 30 minutes to 24 hours, usually 60 minutes to 3 hours.

Step 10B: In this Step, a compound of formula (XXXVIII) can be prepared by thermal cyclization of a compound of formula (XXXVII) in a reaction inert solvent. Examples of suitable solvents include ethers such as phenyl ether. This reaction can be carried out at a temperature in the range from 200 to 300° C. for 30 minutes to 24 hours, usually 250° C. for 30 minutes to 5 hours. (Journal of Medicinal chemistry, 1998, Vol 41, No 25.)

Step 10C: In this Step, a compound of formula (XXXIX) can be prepared by halogenation of a compound of formula (XXXVIII). The reaction is carried out under halogenation conditions with a halogenating reagent in a reaction inert solvent or without solvent. Examples of suitable solvents include THF, 1,4-dioxane, DMF, acetonitrile; halogenated hydrocarbons, such as DCM, 1,2-dichloroethane, chloroform or carbon tetrachloride and acetic acid. Examples of suitable halogenating reagents include phosphorus oxyhalide such as phosphorus oxychloride and phosphorus oxybromide. The reaction can be carried out at a temperature of from 0° C. to 200° C., more preferably from ambient temperature to 150° C. Reaction times are, in general, from 5 minutes to 48 hours, more preferably 30 minutes to 6 hours, will usually suffice.

Step 10D: In this Step, a dehalogenated compound of formula (XL) can be prepared by hydrogenation of a compound of formula (XXXIX) in a solvent. Hydrogenation reaction is carried out under, for example, known hydrogenolysis conditions in the presence of a metal catalyst under hydrogen atmosphere or in the presence of hydrogen sources such as formic acid or ammonium formate in a reaction inert solvent. If desired, the reaction is carried out under basic conditions, for example, in the presence of triethylamine. Preferred reagents are selected from, for example, nickel catalysts such as Raney nickel, palladium-carbon, palladiumhydroxide-carbon, platinumoxide, platinum-carbon, ruthenium-carbon, rhodium-aluminumoxide, tris[triphenyphosphine]rhodiumchloride. Examples of suitable reaction inert aqueous or non-aqueous organic solvents include alcohols, such as MeOH, EtOH; ethers, such as THF or 1,4-dioxane; acetone; dimethylformamide; halogenated hydrocarbons, such as DCM, dichloroethane or chloroform; and acetic acid or mixtures thereof. The reaction can be carried out at a temperature in the range from of 20° C. to 100° C., preferably in the range of 20° C. to 60° C. Reaction times are, in general, from 10 minutes to 48 hours, preferably 30 minutes to 24 hours. This reaction can be carried out under hydrogen atmosphere at a pressure ranging from 1 to 100 atom, preferably from 1 to 10 atm. Preferred conditions comprise the use of 5 or 10% palladium-carbon at ambient temperature for 1 to 24 hours under hydrogen atmosphere using a balloon.

Step 10E: In this Step, an acid compound of formula (III) can be prepared by hydrolysis of the compound of formula (XL) in a solvent by the method as described in Step 9E.

Scheme 11:

When $Y^1$ is N, $Y^2$ is CH and $Y^3$ is CH, a compound of formula (III) may be prepared by the process illustrated below.

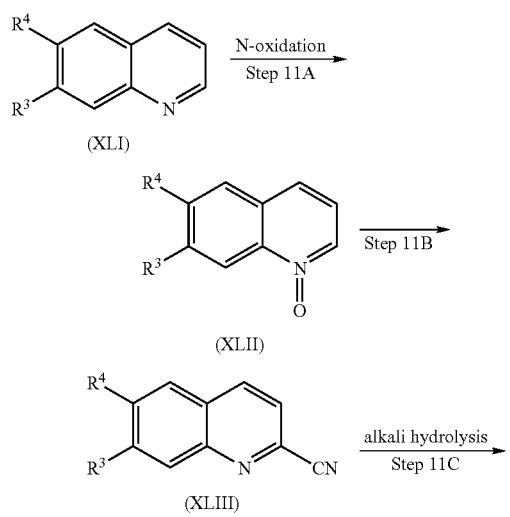

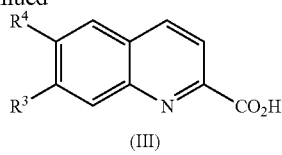

Step 11A: In this Step, a N-oxide compound of formula (XLII) can be prepared by oxidation of a compound of formula (XLI) in a reaction inert solvent. The oxidation reaction may be carried out in the absence or presence of an additive agent in a reaction inert solvent. Examples of preferred oxidation reagents are meta-chloroperbenzoic acid (mCPBA), hydrogen peroxide, peracetic acid. Examples of preferred reaction inert solvents include halogenated hydrocarbons, such as methylene chloride, chloroform, carbon tetrachloride and dichloroethane; ethers, such as diethyl ether, diisopropyl ether, DME, THF and 1,4-dioxane; acetonitrile, acetic acid and water or mixtures thereof. Reaction temperatures are generally in the range of 0° C. to 250° C., more preferably in the range of 0° C. to 100° C. Reaction times are, in general, from 1 minute to a 10 day, more preferably from 20 minutes to 6 hours. This reaction may be carried out in the presence of a suitable catalyst. There is likewise no particular restriction on the nature of the catalyst used, and any catalyst commonly used in reactions of this type may equally be used here. Examples of such catalysts include methyltrioxorhenium (VII), tungstic acid and sodium tungstate dehydrate.

Step 11B: In this Step, a cyano compound of formula (XLIII) can be prepared by cyanation of a compound of formula (XLII) in a reaction inert solvent. Examples of preferred cyanation reagents include trimethylsilanecarbonitrile (TMSCN), the combination of trimethylchlorosilane and sodium cyanide, and the combination of acylating agents such as N,N-dimethylcarbamoyl chloride with trimethylsilanecarbonitrile (TMSCN). A preferred cyanation reagent is trimethylsilanecarbonitrile (TMSCN) in the presence of a base such triethylamine in a reaction inert solvent. Examples of preferred reaction inert solvents include halogenated hydrocarbons, such as methylene chloride, chloroform, carbon tetrachloride and dichloroethane; ethers, such as diethyl ether, DME, THF and 1,4-dioxane; acetonitrile, DMF, DMSO or mixtures thereof. Reaction temperatures are generally in the range of 0° C. to 250° C., more preferably in the range of 0° C. to 100° C. Reaction times are, in general, from 1 minute to 10 days, more preferably from 20 minutes to 24 hours.

Step 11C: In this Step, an acid compound of formula (III) can be prepared by hydrolysis of a cyano compound of formula (XLIII) in a solvent. The hydrolysis can be carried out by conventional procedures. In a typical procedure, the hydrolysis may be carried out under basic conditions, e.g. in the presence of sodium hydroxide, potassium hydroxide or lithium hydroxide. Examples of suitable solvents include alcohols such as MeOH, EtOH, propanol, butanol, 2-methoxyethanol, and ethylene gylcol; ethers such as THF, DME, and 1,4-dioxane; amides such as DMF and hexamethylphosphorictriamide; and sulfoxides such as DMSO. Preferable solvents are MeOH, EtOH, propanol, THF, DME, 1,4-dioxane, DMF and DMSO. This reaction can be carried out at a temperature in the range from −20 to 150° C., usually from 20° C. to 100° C. for 30 minutes to 24 hours, usually 60 minutes to 10 hours.

Scheme 12:

When wherein $Y^3$ is N, $Y^1$ and $Y^2$ are CH, and $R^4$ is trifluoromethyl, a compound of formula (III) may be prepared by the process illustrated below.

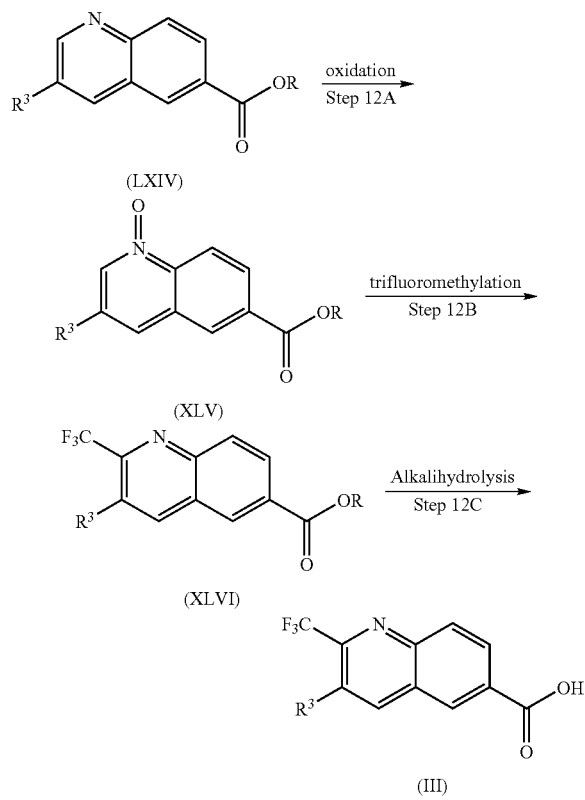

wherein R is $(C_1-C_6)$alkyl.

Step 12A: In this Step, a N-oxide compound of formula (XLV) can be prepared by oxidation of a compound of formula (XLIV) in a solvent by the method as described in Step 11A.

Step 12B: In this Step, a compound of formula (XLVI) can be prepared by trifluoromethylation of a compound of formula (XLV) in a reaction inert solvent. Examples of preferred trifluoromethylation reagents include the combination of trifluoromethyltrimethylsilane (TMSCF$_3$) and initiator reagents. Examples of preferred catalytic initiator reagents include tetrabutylammonium fluoride cesium fluoride, lithium acetate, sodium acetate, potassium acetate, tetrabutylammonium acetate, lithium pivalate, lithium benzoate, potassium t-butoxide, sodium t-butoxide. Examples of preferred reaction inert solvents include hydrocarbons, such as hexane, benzene, toluene; halogenated hydrocarbons, such as methylene chloride, chloroform, carbon tetrachloride and dichloroethane; ethers, such as diethyl ether, diisopropyl ether, DME, THF and 1,4-dioxane; acetonitrile, EtOAc, DMF, DMSO or mixtures thereof. Reaction temperatures are generally in the range of −78° C. to 200° C., more preferably in the range of −78° C. to 100° C. Reaction times are, in general, from 1 minute to 10 days, more preferably from 20 minutes to 24 hours.

Step 12C: In this Step, an acid compound of formula (III) can be prepared by hydrolysis of a compound of formula (XLVI) in a solvent by the method as described in Step 9E.

Scheme 13:

When $Y^3$ is N and $Y^1$ and $Y^2$ are CH, a compound of formula (III) may be prepared by the process illustrated below.

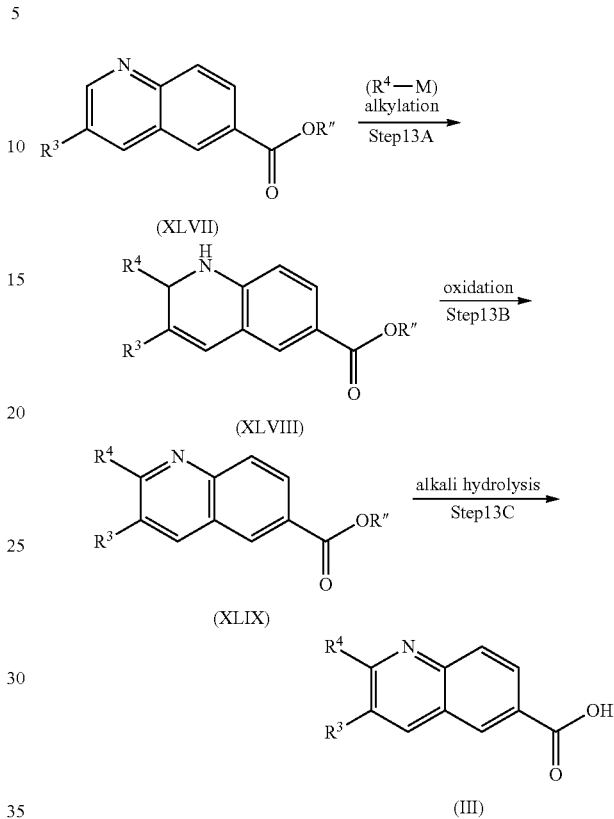

wherein R″ is $(C_1-C_6)$alkyl or benzyl; and M is a metal, such as lithium, or MgX, wherein X is hydrogen or halogen.

Step 13A: In this Step, a 1,2-dihydroquinoline compound of formula (XLVIII) can be prepared by alkylation of a compound of formula (XLVII) in a reaction inert solvent. The organometallic compound of formula $R^4$-M can be prepared by reaction of a halide compound of $R^4$, wherein $R^4$ is alkyl. M represents a metal such as lithium, or MgX, wherein X represents a hydrogen atom, a halogen atom such as, fluorine, chlorine, bromine or iodine. Examples of suitable organometallic reagents include alkyllithiums such as methyllithium, n-butyllithium, sec-butyllithium and tert-butyllithium; aryllithiums such as phenyllithium and lithium naphtilide; alkylmagnesium halide such as methylmagnesium halide, isopropylmagnesium halide, and t-butylmagnesium halide; arylmagnesium halide such as phenylmagnesium halide. Examples of preferred reaction inert solvents include hydrocarbons, such as hexane; ethers, such as diethyl ether, diisopropyl ether, DME, THF and 1,4-dioxane; or mixtures thereof. Reaction temperatures are generally in the range of −100 to 100° C., preferably in the range of from −100° C. to room temperature. Reaction times are, in general, from 1 minute to a day, preferably from 1 hour to 24 hours.

Step 13B: In this Step, a compound of formula (XLIX) can be prepared by oxidation of a compound of formula (XLVIII) in a solvent. Examples of suitable oxidative agents include Cr-reagents, such as chromium trioxide (CrO$_3$), potassium chromate (K$_2$CrO$_4$), potassium dichromate (K$_2$Cr$_2$O$_7$); Mn-reagents, such as manganese dioxide (MnO$_2$), potassium permanganate (KMnO$_4$); quinine reagents, such as 2,3,5,6-tetrachloro-1,4-benzoquinone (p-chloranil), 2,3-dichloro-5,6-dicyano-1,4-benzoquinone (DDQ); and air oxidation. Examples of suitable solvents include THF, 1,4-dioxane, acetone, DMF, acetonitrile, halogenated hydrocarbons (e.g., DCM, dichloroethane, chloroform), water; or mixtures thereof. The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −78° C. to 100° C., more preferably from about −60° C. to 60° C. The time required for the reaction may also vary widely, depending on many factors, notably the reaction temperature and the nature of the reagents and solvent employed. However, provided that the reaction is effected under the preferred conditions outlined above, a period of 1 minute to 24 hours, more preferably 30 minutes to 12 hours, will usually suffice.

Step 13C: In this Step, an acid compound of formula (III) can be prepared by hydrolysis of a compound of formula (XLIX) in a solvent by the method as described in Step 9E.

Scheme 14

When $R^4$ is 1-methyl-1-trifluoromethylalkyl, a compound of formula (III) may be prepared by the process illustrated below.

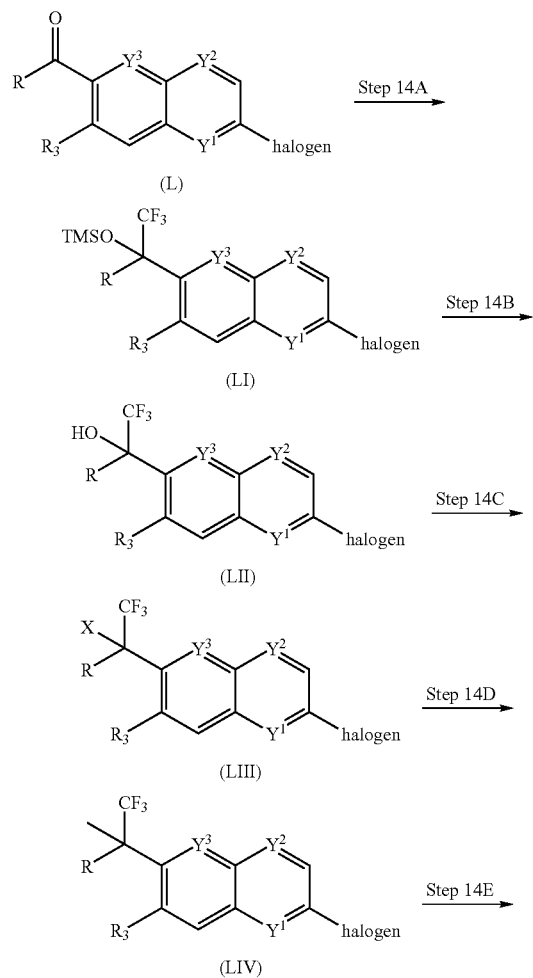

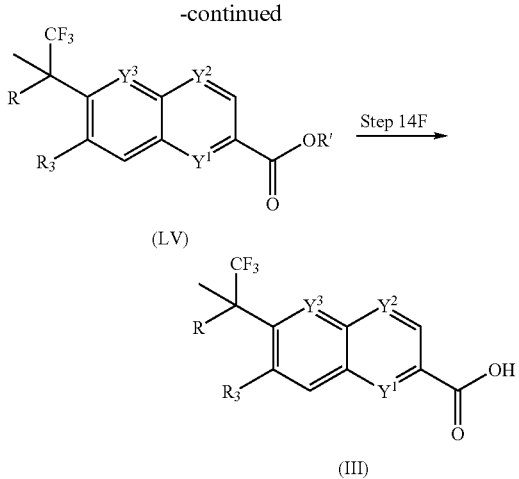

wherein R is $(C_1-C_3)$alkyl; and X is halogen, O-mesylate, O-tosylate or O-triflate; and R' is $(C_1-C_6)$alkyl.

Step 14A

In this Step, a compound of formula (LI) can be prepared by nucleophilic trifluoromethylation of a compound of formula (L) in a reaction inert solvent. Examples of preferred trifluoromethylation reagents include the combination of trifluoromethyltrimethylsilane (TMSCF$_3$) and initiator reagents. Examples of preferred catalytic initiator reagents include tetrabutylammonium fluoride (TBAF), cesium fluoride (CsF), lithium acetate (AcOLi), sodium acetate (AcONa), potassium acetate (AcOK), tetrabutylammonium acetate (AcO-nNBu4), lithium pivalate (t-BuCO2Li), lithium benzoate (PhCO2Li), potassium t-butoxide (KO-tBu), and sodium t-butoxide (NaO-tBu). Examples of preferred reaction inert solvents include hydrocarbons, such as hexane, benzene, toluene; halogenated hydrocarbons, such as methylene chloride, chloroform, carbon tetrachloride and dichloroethane; ethers; such as diethyl ether, diisopropyl ether, 1,2-dimethoxyethane (DME), tetrahydrofuran and dioxane; acetonitrile; ethyl acetate; N,N-dimethylformamide (DMF); dimethylsulfoxide (DMSO); or mixtures thereof. Reaction temperatures are generally in the range of −78° C. to 200° C., more preferably in the range of −78° C. to 100° C. Reaction times are, in general, from 1 minute to 10 days, more preferably from 10 minutes to 24 hours.

Step 14B

In this Step, a compound of the formula (LII) can be prepared by deprotection of a compound of formula (LI) under various conditions in an inert solvent using a method of Protective Groups in Organic Synthesis (JOHN WILEY & SONS, Inc.); T. W. Greene and P. G. M. Wuts. Examples of suitable deprotecting agents are selected from, for example, but not limited to, acid conditions using hydrochloric acid, citric acid, hydrogen fluoride (HF) or polystyrene sulfonic acid, tetraammonium fluoride such as tetrabutylammonium fluoride and basic conditions using potassium carbonate. This reaction may be carried out in an inert solvent such as ethers such as tetrahydrofuran, diethyl ether, 1,2-dimethoxyethane or 1,4-dioxane; halogenated hydrocarbons such as dichloromethane, 1,2-dichloroethane, chloroform or carbon tetrachloride; acetonitrile; dimethylsulfoxide; N,N-dimethylformamide; hydrocarbons, such as n-hexane, cyclohexane, benzene and toluene; or mixtures thereof. Reaction temperature is generally in the range of 20° C. to 150° C., preferably in the range of 20° C. to 100° C., but if necessary, lower or higher temperature can be employed. Reaction time is, in general, from 1 minute to 2 days, preferably from 20 minutes to 24 hours.

Step 14C

In this Step, a compound of formula (LIII) can be prepared by halogenation, O-mesylation, O-tosylation and O-triflate of a compound of formula (LII) in a reaction inert solvent or without solvent.

The halogenation reaction can be carried out using a halogenating reagent in an inert solvent or without solvent. Examples of suitable solvents include tetrahydrofuran; 1,4-dioxane; N,N-dimethylformamide; acetonitrile; halogenated hydrocarbons, such as dichloromethane, 1,2-dichloroethane, chloroform or carbon tetrachloride; and acetic acid. Example of suitable halogenating reagents include thionyl chloride, oxalyl chloride, phosphorus pentachloride, phosphorus tribromide, phosphorus oxyhalide such as phosphorus oxychloride and phosphorus oxybromide, and lewis acids such as titanium chloride, tin chloride and aluminium chloride. The reaction can be carried out at a temperature of from −78° C. to 200° C., more preferably from −20° C. to 150° C. Reaction times are, in general, from 5 minute to 10 days, more preferably from 30 minutes to 24 hours.

The O-mesylation, O-tosylation and O-triflate reactions can be carried out by the reaction of O-activating reagents with a compound of formula (LII) in the presence of a base in an inert solvent or without solvent. Examples of suitable O-activation reagents include methanesulfonyl chloride, p-toluenesulfonyl chloride, trifluoromethanesulfonyl chloride and trifluoromethanesulfonic acid anhydride. Examples of suitable base include alkyl lithium such as n-butyl lithium, sec-butyl lithium and tert-butyl lithium; potassium t-butoxide and sodium t-butoxide (NaO-tBu); triethylamine, diisopropylethylamine, 4-dimethylaminopyridine and pyridine. Examples of preferred reaction inert solvents include hydrocarbons, such as hexane, benzene, toluene; halogenated hydrocarbons, such as methylene chloride, chloroform, carbon tetrachloride and dichloroethane; ethers; such as diethyl ether, diisopropyl ether, 1,2-dimethoxyethane (DME), tetrahydrofuran and dioxane; acetonitrile, N,N-dimethylformamide (DMF), dimethylsulfoxide (DMSO) or mixtures thereof. The reaction can be carried out at a temperature of from −78° C. to 150° C., more preferably from −78° C. to 100° C. Reaction times are, in general, from 5 minute to 48 days, more preferably from 30 minutes to 24 hours.

Step 14D

In this Step, a compound of formula (LIV) can be prepared by reaction of a compound of formula (LIII) with an alkylating reagent in an inert solvent. Examples of preferred alkylating agents include trialkylmetals such as trimethylaluminum, triethylaluminum; and alkylmagnesium halides such as methylmagnesium bromide in the presence of additive compound such as lithium bromide; or dialkyltitanium halides such as dimethyltitanium dichloride prepared by dimethylzinc and titanium chloride; and is most preferably trimethylaluminum. Examples of preferred inert solvents for the reaction include halogenated hydrocarbons, such as dichloromethane (DCM), 1,2-dichloroethane, chloroform or carbon tetrachloride; ethers, such as diethyl ether, diisopropyl ether, 1,2-dimethoxyethane (DME), tetrahydrofuran (THF) and 1,4-dioxane; hydrocarbons, such as n-hexane, cyclohexane, benzene and toluene; or mixtures thereof. Reaction temperatures are generally in the range of from −100° C. to 200° C., preferably in the range of from −40° C. to 100° C. Reaction times are, in general, from 1 minute to 10 days, preferably from 1 hour to 24 hours.

Step 14E

In this Step, a compound of formula (LV) can be prepared by alkoxycarbonyl insertion reaction of a compound of formula (LIV) in a solvent by the method as described in Step 9D.

Step 14F

In this Step, an acid compound of formula (III) can be prepared by hydrolysis of a compound of formula (LV) in a solvent by the method as described in Step 9E.

The various general methods described above may be useful for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product. The starting materials are commercially available or can be easily prepared by the man skilled in the art by routine experiment.

Method for Assessing Biological Activities

Human VR1 Antagonist Assay

VR1 antagonistic activity can be determined by the $Ca^{2+}$ imaging assay using human VR1 highly expressing cells. The cells that highly express human VR1 receptors are obtainable from several different conventional methods. The one standard method is cloning from human Dorsal Root Ganglion (DRG) or kidney according to the methods such as described in the journal article; Nature, 389, pp 816-824, 1997. Alternatively VR1 receptors highly expressing human keratinocytes are also known and published in the journal article (Biochemical and Biophysical Research Communications, 291, pp 124-129, 2002). In this article, human keratinocytes demonstrated VR1 mediated intracellular $Ca^{2+}$ increase by addition of capsaicin. Furthermore, the method to up regulate human VR1 gene, which is usually a silent gene or don't produce detectable level of VR1 receptors, is also available to obtain propriety cells. Such genetic modification method was described in detail; Nat. Biotechnol., 19, pp 440-445, 2001.

The cells that express human VR1 receptors were maintained in culture flask at 37° C. in an environment containing 5% $CO_2$ until use in the assay. The intracellular $Ca^{2+}$ imaging assay to determine VR1 antagonistic activities were done by following procedures.

The culture medium was removed from the flask and fura-2/AM fluorescent calcium indicator was added to the flask at a concentration of 5 µM in the medium. The flask was placed in $CO_2$ incubator and incubated for 1 hour. Then the cells expressing the human VR1 receptors were detached from the flask follow by washing with phosphate buffer saline, PBS(−) and re-suspended in assay buffer. The 80 µl of aliquot of cell suspension ($3.75 \times 10^5$ cells/ml) was added to the assay plate and the cells were spun down by centrifuge (950 rpm, 20° C., 3 minutes).

The compounds of the examples were tested in the Human VR1 antagonist assay described above. The inhibition concentration 50% ($IC_{50}$) values are presented in the following table.

TABLE 1

| Example # | $IC_{50}$(nM) |
|---|---|
| A1 | 93.5 |
| A2 | 34.2 |
| B1 | 590 |
| C1 | Not tested |
| C2 | 667 |
| D1 | 74.1 |
| D2 | 176 |

TABLE 1-continued

| Example # | IC$_{50}$(nM) |
| --- | --- |
| D3 | 403 |
| D4 | 270 |
| D5 | 331 |
| D6 | Not tested |
| D7 | 31.9 |
| D8 | 434 |
| D9 | Not tested |
| D10 | 311 |
| D11 | 501 |
| D12 | 181 |
| D13 | 31.8 |
| D14 | 65.5 |
| D15 | 254 |
| Capsazepine (control) | 237-455 |

Capsaicin Stimulation Assay

The capsaicin-induced changes in the intracellular calcium concentration were monitored using FDSS 6000 (Hamamatsu Photonics, Japan), a fluorometric imaging system. The cell suspension in Krebs-Ringer HEPES (KRH) buffer (115 mM NaCl, 5.4 mM KCl, 1 mM MgSO$_4$, 1.8 mM CaCl$_2$, 11 mM D-Glucose, 25 mM HEPES, 0.96 mM Na$_2$HPO$_4$, pH 7.3) were pre-incubated with varying concentrations of the test compounds or KRH buffer (buffer control) for 15 minutes at room temperature under the dark condition. Then capsaicin solution, which gives 300 nM in assay mixture, was automatically added to the assay plate by the FDSS 6000.

Acid Stimulation Assay

The acid-induced changes in the intracellular calcium concentration were monitored using FDSS 6000 (Hamamatsu Photonics, Japan), a fluorometric imaging system. The cell suspension in resting buffer (HBSS supplemented with 10 mM HEPES, pH 7.4) were pre-incubated with varying concentrations of the test compounds or resting buffer (buffer control) for 15 minutes at room temperature under the dark condition. The cells were automatically added the stimulating solution (HBSS supplemented with MES, final assay buffer pH5.8) by the FDSS 6000. The IC$_{50}$ values of VR1 antagonists were determined from the half of the increase demonstrated by buffer control samples after acidic stimulation.

Determination of Antagonist Activity

The monitoring of the changes in the fluorescence signals ($\lambda$ex=340 nm/380 nm, $\lambda$em=510-520 nm) was initiated at 1 minute prior to the addition of capsaicin solution or acidic buffer and continued for 5 minute. The IC$_{50}$ values of VR1 antagonists were determined from the half of the increase demonstrated by buffer control samples after agonist stimulation.

Human VR1 Agonist Assay

The cells that express human VR1 receptors were maintained in culture flask at 37° C. in an environment containing 5% CO$_2$ until use in the assay. The intracellular Ca$^{2+}$ imaging assay to determine VR1 agonistic activities were done by following procedures. The culture medium was removed from the flask and fura-2/AM fluorescent calcium indicator was added to the flask at a concentration of 5 µM in the medium. The flask was placed in CO$_2$ incubator and incubated for 1 hour. Then the cells expressing the human VR1 receptors were detached from the flask follow by washing with phosphate buffer saline, PBS(−) and re-suspended in Krebs-Ringer HEPES buffer (KRH): 115 mM NaCl, 5.4 mM KCl, 1 mM MgSO$_4$, 1.8 mM CaCl$_2$, 11 mM D-Glucose, 25 mM HEPES, 0.96 mM Na$_2$HPO$_4$, pH 7.3.

96-Well Format Assay

The test compound-induced changes in the intracellular calcium concentration were monitored using FDSS 6000 (Hamamatsu Photonics, Japan), a fluorometric imaging system. The 80 µL of aliquot of cell suspension (3.75×10$^5$ cells/mL) in KRH buffer was distributed into the 96-well plate, and then this assay plate was placed on the FDSS6000. Finally 20 µL of varying concentrations of the test compounds or KRH buffer (buffer control) or 1 µM capsaicin (maximum response control) were automatically added to the assay plate by the FDSS 6000.

384-Well Format Assay

The 30 µL of aliquot of cell suspension (8×10$^5$ cells/mL) in KRH buffer was distributed into the 384-well plate, and then this assay plate was placed on the FDSS6000. Finally 15 µL of varying concentrations of the test compounds or KRH buffer. (buffer control) or 2 µM capsaicin (maximum response control) were automatically added to the assay plate by the FDSS 6000.

Determination of Agonist Activity

The monitoring of the changes in the fluorescence signals ($\lambda$ex=340 nm/380 nm, $\lambda$em=510-520 nm) was initiated 1 min (96-well format) or 15 seconds (384-well format) prior to the addition of test compounds and continued for 5 minute. The EC$_{50}$ values of compounds were determined from the maximum response of test compounds. The E$_{max}$ values were determined as a percentage of 1 µM (96-well format) or 2 µM (384-well format) capsaicin-induced response.

Chronic Constriction Injury Model (CCI Model)

Male Sprague-Dawley rats (270-300 g; B.W., Charles River, Tsukuba, Japan) were used. The chronic constriction injury (CCI) operation was performed according to the method described by Bennett and Xie (Bennett, G. J. and Xie, Y. K. Pain, 33:87-107, 1988). Briefly, animals were anesthetized with sodium pentobarbital (64.8 mg/kg, i.p.) and the left common sciatic nerve was exposed at the level of the middle of the thigh by blunt dissection through biceps femoris. Proximal to the sciatic's trifurcation was freed of adhering tissue and 4 ligatures (4-0 silk) were tided loosely around it with about 1 mm space. Sham operation was performed as same as CCI surgery except for sciatic nerve ligation. Two weeks after surgery, mechanical allodynia was evaluated by application of von Frey hairs (VFHs) to the plantar surface of the hind paw. The lowest amount of force of VFH required to elicit a response was recorded as paw withdrawal threshold (PWT). VFH test was performed at 0.5, 1 and 2 hr post-dosing. Experimental data were analyzed using Kruskal-Wallis test followed by Dunn's test for multiple comparisons or Mann-Whitney U-test for paired comparison.

Mono-Iodoacetate (MIA)-Induced OA Model

Male 6-weeks-old Sprague-Dawley (SD, Japan SLC or Charles River Japan) rats were anesthetized with pentobarbital. Injection site (knee) of MIA was shaved and cleaned with 70% EtOH. Twenty-five µl of MIA solution or saline was injected in the right knee joint using a 29G needle. The effect of joint damage on the weight distribution through the right (damaged) and left (untreated) knee was assessed using an incapacitance tester (Linton Instrumentation, Norfolk, UK). The force exerted by each hind limb was measured in grams. The weight-bearing (WB) deficit was determined by a difference of weight loaded on each paw. Rats were trained to measure the WB once a week until 20 days post MIA-injection. Analgesic effects of compounds were measured at 21 days after the MIA injection. Before the compound administration, the "pre value" of WB deficit was measured. After the administration of compounds, attenuation of WB deficits was determined as analgesic effects.

Complete Freund's Adjuvant (CFA) Induced Thermal and Mechanical Hyperalgesia in Rats Thermal Hyperalgesia Male 6-week-old SD rats were used. Complete Freund's adjuvant (CFA, 300 μg of *Mycobacterium Tuberculosis* H37RA (Difco, MI) in 100 μL of liquid paraffin (Wako, Osaka, Japan)) was injected into the plantar surface of hind paw of the rats. Two days after CFA-injection, thermal hyperalgesia was determined by method described previously (Hargreaves et al., 1988) using the plantar test apparatus (Ugo-Basil, Varese, Italy). Rats were adapted to the testing environment for at least 15 min prior to any stimulation. Radiant heat was applied to the plantar surface of hind paw and paw withdrawal latencies (PWL, seconds) were determined. The intensity of radiant heat was adjusted to produce the stable PWL of 10 to 15 seconds. The test compound was administered in a volume of 0.5 mL per 100 g body weight. PWL were measured after 1, 3 or 5 hours after drug administration.

Mechanical Hyperalgesia

Male 4-week-old SD rats were used. CFA (300 μg of *Mycobacterium Tuberculosis* H37RA (Difco, MI) in 100 μL of liquid paraffin (Wako, Osaka, Japan)) was injected into the plantar surface of hind paw of the rats. Two days after CFA-injection, mechanical hyperalgesia was tested by measuring paw withdrawal threshold (PWT, grams) to pressure using the analgesy-Meter (Ugo-Basil, Varese, Italy). The animals were gently restrained, and steadily increasing pressure was applied to the dorsal surface of a hind paw via a plastic tip. The pressure required to elicit paw withdrawal was determined. The test compound was administered in a volume of 0.5 mL per 100 g body weight. PWT were measured after 1, 3 or 5 hours after drug administration.

Parallel Artificial Membrane Permeation Assay (PAMPA)

Experiments were performed in 96-well acceptor and donor plates. Such 96-well system was described in *Journal of Medicinal Chemistry*, 1998, vol. 41, No. 7, 1007-1010. 4% phosphatidylcholine and 1% stearic acid in dodecane were used as artificial membrane material. The acceptor plate (96 well hydrophobic filter plate (MAIP N45, Millipore)) was prepared by adding 5 μL of artificial membrane material on the top of the filter and the plate was filled with 250 μL of 2-(N-morpholino)ethanesulfonic acid (MES) buffered Hank's balanced salt solution (HBSS) (pH 6.5). The donor plate (Transport Receiver plate (MATRNPS50, Millipore)) was filled with 300 μL of MES buffered HBSS (pH 6.5) containing 10 μM of the test compounds. The acceptor plate was placed onto the donor plate to form a "sandwich" and was incubated at 30° C. for 2.5 hours. After the incubation period, acceptor, donor and initial donor solution (reference) were analyzed via LC-MS/MS. Data were reported as the effective permeability value in cm×$10^6$/sec and the membrane retention value.

Human Dofetilide Binding

Cell paste of HEK-293 cells expressing the HERG product can be suspended in 10-fold volume of 50 mM Tris buffer adjusted at pH 7.5 at 25° C. with 2 M HCl containing 1 mM $MgCl_2$, 10 mM KCl. The cells were homogenized using a Polytron homogenizer (at the maximum power for 20 seconds) and centrifuged at 48,000 g for 20 minutes at 4° C. The pellet was resuspended, homogenized and centrifuged once more in the same manner. The resultant supernatant was discarded and the final pellet was resuspended (10-fold volume of 50 mM Tris buffer) and homogenized at the maximum power for 20 seconds. The membrane homogenate was aliquoted and stored at −80° C. until use. An aliquot was used for protein concentration determination using a Protein Assay Rapid Kit and ARVO SX plate reader (Wallac). All the manipulation, stock solution and equipment were kept on ice at all time. For saturation assays, experiments were conducted in a total volume of 200 μl. Saturation was determined by incubating 20 μl of [$^3$H]-dofetilide and 160 μl of membrane homogenates (20-30 μg protein per well) for 60 min at room temperature in the absence or presence of 10 μM dofetilide at final concentrations (20 μl) for total or nonspecific binding, respectively. All incubations were terminated by rapid vacuum filtration over polyetherimide (PEI) soaked glass fiber filter papers using Skatron cell harvester followed by two washes with 50 mM Tris buffer (pH 7.5 at 25° C.). Receptor-bound radioactivity was quantified by liquid scintillation counting using Packard LS counter.

For the competition assay, compounds were diluted in 96 well polypropylene plates as 4-point dilutions in semi-log format. All dilutions were performed in DMSO first and then transferred into 50 mM Tris buffer (pH 7.5 at 25° C.) containing 1 mM $MgCl_2$, 10 mM KCl so that the final DMSO concentration became equal to 1%. Compounds were dispensed in triplicate in assay plates (4 μl). Total binding and nonspecific binding wells were set up in 6 wells as vehicle and 10 μM dofetilide at final concentration, respectively. The radioligand was prepared at 5.6× final concentration and this solution was added to each well (36 μl). The assay was initiated by addition of YSi poly-L-lysine Scintillation Proximity Assay (SPA) beads (50 μl, 1 mg/well) and membranes (110 μl, 20 μg/well). Incubation was continued for 60 min at room temperature. Plates were incubated for a further 3 hours at room temperature for beads to settle. Receptor-bound radioactivity was quantified by counting Wallac MicroBeta plate counter.

$I_{HERG}$ Assay

HEK 293 cells which stably express the HERG potassium channel were used for electrophysiological study. The methodology for stable transfection of this channel in HEK cells can be found elsewhere (Z. Zhou et al., 1998, Biophysical Journal, 74, pp 230-241). Before the day of experimentation, the cells were harvested from culture flasks and plated onto glass coverslips in a standard Minimum Essential Medium (MEM) medium with 10% Fetal Calf Serum (FCS). The plated cells were stored in an incubator at 37° C. maintained in an atmosphere of 95% $O_2$/5% $CO_2$. Cells were studied between 15-28 hrs after harvest.

HERG currents were studied using standard patch clamp techniques in the whole-cell mode. During the experiment the cells were superfused with a standard external solution of the following composition (mM); NaCl, 130; KCl, 4; $CaCl_2$, 2; $MgCl_2$, 1; Glucose, 10; HEPES, 5; pH 7.4 with NaOH. Whole-cell recordings was made using a patch clamp amplifier and patch pipettes which have a resistance of 1-3 MOhm when filled with the standard internal solution of the following composition (mM); KCl, 130; MgATP, 5; $MgCl_2$, 1.0; HEPES, 10; EGTA 5, pH 7.2 with KOH. Only those cells with access resistances below 15 MΩ and seal resistances >1 GΩ was accepted for further experimentation. Series resistance compensation was applied up to a maximum of 80%. No leak subtraction was done. However, acceptable access resistance depended on the size of the recorded currents and the level of series resistance compensation that can safely be used. Following the achievement of whole cell configuration and sufficient time for cell dialysis with pipette solution (>5 min), a standard voltage protocol was applied to the cell to evoke membrane currents. The voltage protocol is as follows. The membrane was depolarized from a holding potential of −80 mV to +40 mV for 1000 ms. This was followed by a descending voltage ramp (rate 0.5 mV msec$^{-1}$) back to the holding potential. The voltage protocol was applied to a cell continuously throughout the experiment every 4 seconds (0.25 Hz). The amplitude of the peak current elicited around −40 mV during the ramp was measured. Once stable evoked current responses were obtained in the external solution, vehicle (0.5% DMSO in the standard external solution) was applied for 10-20 min by a peristalic pump. Provided there were minimal changes in the amplitude of the evoked current response in the vehicle control condition, the test compound of either 0.3, 1, 3, 10 μM was applied for a 10 min period. The 10 min period included the time which supplying solution was passing through the tube from solution reservoir to the recording chamber via the pump. Exposing time of cells to the compound solution was more than 5 min after the drug concentration in the chamber well reached the attempting concentration. There was a subsequent wash period of a 10-20 min to assess reversibility. Finally, the cells were exposed to high dose of dofetilide (5 μM), a specific IKr blocker, to evaluate the insensitive endogenous current.

All experiments were performed at room temperature (23±1° C.). Evoked membrane currents were recorded on-line on a computer, filtered at 500-1 KHz (Bessel −3 dB) and sampled at 1-2 KHz using the patch clamp amplifier and a specific data analyzing software. Peak current amplitude, which occurred at around −40 mV, was measured off line on the computer.

The arithmetic mean of the ten values of amplitude was calculated under vehicle control conditions and in the presence of drug. Percent decrease of $I_N$ in each experiment was obtained by the normalized current value using the following formula: $I_N=(1-I_D/I_C)\times 100$, where $I_D$ is the mean current value in the presence of drug and $I_C$ is the mean current value under control conditions. Separate experiments were performed for each drug concentration or time-matched control, and arithmetic mean in each experiment is defined as the result of the study.

Drug-Drug Interaction Assay

This method essentially involves determining the percent inhibition of product formation from fluorescence probe at 3 μM of the each compound.

More specifically, the assay is carried out as follows. The compounds were pre-incubated with recombinant CYPs, 100 mM potassium phosphate buffer and fluorescence probe as substrate for 5 min. Reaction was started by adding a warmed NADPH generating system, which consist of 0.5 mM NADP (expect; for 2D6 0.03 mM), 10 mM MgCl$_2$, 6.2 mM DL-Isocitric acid and 0.5 U/ml Isocitric Dehydrogenase (ICD). The assay plate was incubated at 37° C. (expect; for 1A2 and 3A4 at 30° C.) and taking fluoresce reading every minutes over 20 to 30 min.

Data calculations were preceded as follows;
1. The slope (Time vs. Fluorescence units) was calculated at the linear region
2. The percentage of inhibition in compounds was calculated by the equation $$\{(v_o-v_i)/v_o\}\times 100=\% \text{ inhibition}$$

Wherein $v_o$=rate of control reaction (no inhibitor)

$v_i$=rate of reaction in the presence of compounds.

TABLE 2

Condition for drug-drug interaction assay.

| | 1A2 | 2C9 | 2C19 | 2D6 | 3A4 |
|---|---|---|---|---|---|
| Substrate | Vivid blue (Aurora) | MFC (Gentest) | Vivid blue (Aurora) | AMMC (Gentest) | Vivid red (Aurora) |
| Substrate (μM) | 10 | 30 | 10 | 1 | 2 |
| Enzyme (pmol) | 50 | 50 | 5 | 50 | 5 |
| EX./Em (λ) | 408/465 | 408/535 | 408/465 | 400/465 | 530/595 |

Intrinsic Clearance

Test compounds (1 μM) were incubated with 1 mM MgCl$_2$, 1 mM NADP+, 5 mM isocitric acid, 1 U/mL isocitric dehydrogenase and 0.8 mg/mL HLM (human liver microsomes) in 100 mM potassium phosphate buffer (pH 7.4) at 37° C. on a number of 384-well plates. At several time points, a plate was removed from the incubator and the reaction was terminated with two incubation volumes of acetonitrile. The compound concentration in supernatant was measured by LC/MS/MS system. The intrinsic clearance value ($Cl_{int}$) was calculated using following equations:

$Cl_{int}$(μl/min/mg protein)=($k$×incubation volume)/Protein concentration $k$(min$^{-1}$)=−slope of ln(concentration vs. time)

Drug Substance

Pharmaceutically acceptable salts of the compounds of formula (I) include the acid addition and base salts thereof.

Suitable acid addition salts are formed from acids which form non-toxic salts. Examples include acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionization in the salt may vary from completely ionized to almost non-ionized.

The compounds of the invention may exist in both unsolvated and solvated forms. The term 'solvate' is used herein to describe a molecular complex comprising the compound of the invention and one or more pharmaceutically acceptable solvent molecules, for example, EtOH. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975).

Hereinafter all references to compounds of formula (I) include references to salts, solvates and complexes thereof and to solvates and complexes of salts thereof.

The compounds of the invention include compounds of formula (I) as hereinbefore defined, polymorphs, prodrugs, and isomers thereof (including optical, geometric and tautomeric isomers) as hereinafter defined and isotopically-labeled compounds of formula (I).

As stated, the invention includes all polymorphs of the compounds of formula (I) as hereinbefore defined.

Also within the scope of the invention are so-called 'prodrugs' of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H Bundgaard (Elsevier, 1985).

Some examples of prodrugs in accordance with the invention include:
(i) where the compound of formula (I) contains an alcohol functionality (—OH), an ether thereof, for example, replacement of the hydrogen with $(C_1-C_6)$alkanoyloxymethyl; and
(ii) where the compound of formula (I) contains a primary or secondary amino functionality (—$NH_2$ or —NHR where R is not H), an amide thereof, for example, replacement of one or both hydrogens with $(C_1-C_{10})$alkanoyl.

Further examples of replacement groups in accordance with the foregoing examples and examples of other prodrug types may be found in the aforementioned references.

Finally, certain compounds of formula (I) may themselves act as prodrugs of other compounds of formula (I).

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where the compound contains, for example, a keto or oxime group, an aromatic moiety or a heteroaromatic ring including nitrogen of more than two, tautomeric isomerism ('tautomerism') can occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor, or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, New York, 1994).

The present invention, includes all pharmaceutically acceptable isotopically-labelled compounds of formula (I) wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$. Certain isotopically-labelled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, EtOH, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Other possible ingredients include anti-oxidants, colorants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

Solid formulations for oral administration may be formulated to be immediate and/or modified controlled release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

Parenteral Administration

The compounds of the invention may also be administered directly into the blood stream, into muscle, or into an internal organ. Suitable means for parenteral administration include .intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as powdered a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for use with needle-free injection administration comprise a compound of the invention in powdered form in conjunction with a suitable vehicle such as sterile, pyrogen-free water.

Formulations for parenteral administration may be formulated to be immediate and/or modified controlled release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurized container, pump, spray, atomizer, or nebuliser contains a solution or suspension of the compound(s) of the invention comprising, for example, EtOH, aqueous EtOH, or a suitable alternative agent for dispersing, solubilising, or extending release of the active, a propellant(s) as solvent and an optional surfactant, such as sorbitan trioleate, oleic acid, or an oligolactic acid.

Formulations for inhaled/intranasal administration may be formulated to be immediate and/or modified controlled release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 μg to 10 mg of the compound of formula (I). The overall daily dose will typically be in the range 1 μg to 10 mg which may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Dosage

For administration to human patients, the total daily dose of the compounds of the invention is typically in the range 0.1 mg to 3000 mg, preferably from 1 mg to 500 mg, depending, of course, on the mode of administration. For example, oral administration may require a total daily dose of from 0.1 mg to 3000 mg, preferably from 1 mg to 500 mg, while an intravenous dose may only require from 0.1 mg to 1000 mg, preferably from 0.1 mg to 300 mg. The total daily dose may be administered in single or divided doses.

These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

A VR1 antagonist may be usefully combined with another pharmacologically active compound, or with two or more other pharmacologically active compounds, particularly in the treatment of pain. For example, a VR1 antagonist, particularly a compound of formula (I), or a pharmaceutically acceptable salt or solvate thereof, as defined above, may be administered simultaneously, sequentially or separately in combination with one or more agents selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an H₁ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a 5-HT$_{1B/1D}$ agonist such as eletriptan, sumatriptan, naratriptan, zolmitriptan or rizatriptan;

a 5-HT$_{2A}$ receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid, (3R,4R,5R)-3-amino-4,5-dimethyl-octanoic acid, (2S)-2-Amino-4-ethyl-2-methylhexanoic acid and (2S)-2-aminomethyl-5-ethyl-heptanoic acid;

a cannabinoid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuprorion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl]benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl), 1,4-benzoquinone (CV-6504);

a sodium channel blocker, such as lidocaine;

a 5-HT3 antagonist, such as ondansetron;

and the pharmaceutically acceptable salts and solvates thereof.

In as much as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

EXAMPLES

The invention is illustrated in the following non-limiting examples in which, unless stated otherwise: all operations were carried out at room or ambient temperature, that is, in the range of 18-25° C.; evaporation of solvent was carried out using a rotary evaporator under reduced pressure with a bath temperature of up to 60° C.; reactions were monitored by thin layer chromatography (TLC) and reaction times were given for illustration only; melting points (mp) given were uncorrected (polymorphism may result in different melting points); the structure and purity of all isolated compounds were assured by at least one of the following techniques: TLC (Merck silica gel 60 $F_{254}$ precoated TLC plates), mass spectrometry, nuclear magnetic resonance spectra (NMR), infrared absorption spectra (IR) or microanalysis. Yields were given for illustrative purposes only. Flash column chromatography was carried out using Merck silica gel 60 (230-400 mesh ASTM) or Fuji Silysia amino bounded silica (Chromatorex, 30-50 uM) or Biotage amino bounded silica (35-75 μm, KP-NH) or Biotage silica (32-63 μm, KP-Sil). The purification using HPLC was performed by the following apparatus and conditions. Apparatus: UV-trigger preparative HPLC system, Waters (Column: XTerra MS C18, 5 urn, 19×50 mm or 30×50 mm), Detector: UV 254 nm Conditions: $CH_3CN$/0.05% HCOOH aqueous solution or $CH_3CN$/0.01% $NH_3$ aqueous solution; 20 ml/min (19×50 mm) or 40 ml/min (30×50 mm) at ambient temperature. Microwave apparatus used in the reaction was Emrys optimizer (Personal chemistry). Optical rotation was measured by P-1020 (Jasco). Low-resolution mass spectral data (EI) were obtained on a Integrity (Waters) mass spectrometer. Low-resolution mass spectral data (ESI) were obtained on a ZMD (Micromass) mass spectrometer. NMR data were determined at 270 MHz (JEOL JNMLA 270 spectrometer) or 300 MHz (JEOL JNMLA300 spectrometer) using deuterated chloroform (99.8% D) or DMSO (99.9% D) as solvent unless indicated otherwise, relative to tetramethylsilane (TMS) as internal standard in parts per million (ppm); conventional abbreviations used were: s=singlet, d=doublet, t=triplet, q=quartet, quint=quintet, m=multiplet, br.=broad, etc. IR spectra were measured by a Shimazu infrared spectrometer (IR-470). Chemical symbols have their usual meanings; by (boiling point), mp (melting point), L (liter(s)), ml (milliliter(s)), g (gram(s)), mg (milligram(s)), mol (moles), mmol (millimoles), eq. (equivalent(s)), quant. (quantitative yield), sat. (saturated), aq (aqua). In the following Examples, "Me" means methyl and "Et" means ethyl.

Preparations

The following Preparations illustrate the preparation of certain Amine and Carboxylic Acid intermediates used to prepare the Examples hereinbelow.

Amine 1:
4-(Aminomethyl)-5-chloro-2-methoxyphenol

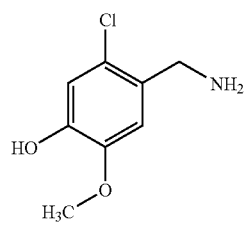

The title amine was prepared by the method described in WO2005/123666.

Amine 2: 4-(Aminomethyl)-5-bromo-2-methoxyphenol

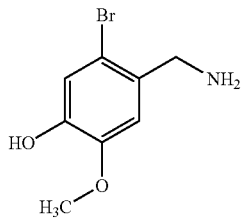

The title amine was prepared by the same procedure as Amine 1, using N-bromosuccinimide instead of N-chlorosuccinimide. $^1$H-NMR (300 MHz, DMSO-d6) δ ppm 3.79 (3H, s), 4.02 (2H, s), 7.04 (1H, s), 7.24 (1H, s), 8.23 (3H, br s), 9.86 (1H, s).

MS(ESI) m/z: 217 (M+H—NH$_2$)$^+$.

Amine 3: (R)-4-(1-Aminoethyl)-5-chloro-2-methoxyphenol

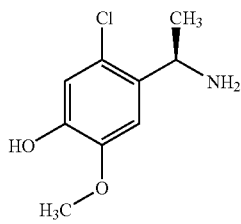

Step A-3A: (R)—N—((R)-1-(4-hydroxy-3-methoxyphenyl)ethyl)-2-methylpropane-2-sulfinamide To a THF (63 ml) solution of 1-(4-hydroxy-3-methoxyphenyl)ethanone (4.99 g, 30.0 mmol, purchased from TCI) and (R)-(+)-2-methyl-2-propanesulfinylamide (4.00 g, 33.0 mmol), titanium(IV) ethoxide (63.0 ml, 0.30 mol) was added under a nitrogen atmosphere and the mixture was refluxed with stirring for 20 hours. After imine formation was confirmed with LC-MS, the mixture was cooled to r.t. and the imine solution was added dropwise to a suspension of sodium borohydride (3.41 g, 90.1 mmol) in THF (50 mL) at 0° C. under nitrogene atmosphere. After stirring at room temperature for 3 hours, the reaction mixture was partitioned with water and ethanol, then the mixture was stirred for 1 hour at room temperature. The mixture was filtered through a Celite pad, and the filtrate was evaporated and concentrated in vacuo. The mixture was dissolved in EtOAc (500 ml), washed with 1N hydrochloric acid (300 ml), saturated aqueous sodium bicarbonate (300 ml), and brine (300 ml), and the organic layer was dried over sodium sulfate. Removal of the solvent gave a residue, which was chromatographed on a column of silica gel, eluting with EtOAc-hexane (1:1 to 3:1), to give the title compound (4.10 g, 50%) as a colorless syrup. $^1$H NMR (270 MHz, CDCl$_3$) δ ppm 1.23 (9H, s), 1.49 (3H, d, J=6.6 Hz), 3.36 (1H, m), 3.89 (3H, s), 4.40-4.60 (1H, m), 5.71 (1H, s), 6.87 (3H, m).

MS (ESI) m/z: not observed M$^+$ peak.

Step A-3B: (R)-4-(1-aminoethyl)-2-methoxyphenol hydrochloride

To (R)—N—((R)-1-(4-hydroxy-3-methoxyphenyl)ethyl)-2-methylpropane-2-sulfinamide (4.10 g, 15.1 mmol) was added 10% hydrogen chloride in methanol (40 ml), and the resulting mixture was stirred at room temperature for 3 h. The reaction mixture was evapolated and dried in vacuo to give the title compound (crude 6.75 g) as a white solid. This crude amine was used for the next step without further purification. $^1$H NMR (270 MHz, DMSO-d$_6$) δ ppm 1.48 (3H, d, J=6.6 Hz), 3.79 (3H, s), 4.27 (1H, m), 6.79 (1H, d, J=8.5 Hz), 6.88 (1H, d, J=8.0 Hz), 7.17 (1H, s), 8.35 (3H, br. s), 9.18 (1H, br. s). MS (ESI) m/z 151 (M+H—NH$_2$)$^+$.

Step A-3C: (R)-4-(1-acetamidoethyl)-2-methoxyphenyl acetate

Acetic anhydride (8 ml, 80 mmol) was added to the solution of (R)-4-(1-aminoethyl)-2-methoxyphenol hydrochloride (crude 6.75 g) in pyridine (50 ml) and the resulting mixture stirred at room temperature for 3 hours. Removal of the solvent gave a residue, which was chromatographed on a column of silica gel, eluting with EtOAc-Hexane (1:1) and then MeOH-DCM (1:10), to give the title compound (2.86 g, 75% for 2 steps) as yellow syrup. $^1$H NMR (300 MHz, CDCl$_3$) δ ppm 1.49 (3H, d, J=6.6 Hz), 1.99 (3H, s), 2.31 (3H, s), 3.83 (3H, s), 5.12 (1H, m), 5.67 (1H, m), 6.78-7.08 (3H, m). MS (ESI) m/z not observed M$^+$ peak.

Step A-3D: (R)-4-(1-acetamidoethyl)-5-chloro-2-methoxyphenyl acetate)

N-Chlorosuccinimide (2.28 g, 17.1 mmol) was added to a solution of (R)-4-(1-acetamidoethyl)-2-methoxyphenyl acetate (2.86 g, 11.4 mmol) in DMF (50 mL) and the mixture was stirred for 1 hour at 0° C. and then for 15 hours at room temperature. The reaction mixture was poured onto aqueous 20% sodium thiosulfate solution and extracted with DCM 3 times. The combined organic layer was dried over sodium sulfate, filtered and evaporated. The residue was chromatographed on a column of silica gel, eluting with EtOAc-Hexane (1:1) and then MeOH-DCM (1:10), to give a brown solid. The solid was washed with Et$_2$O and dried in vacuo to give the title compound (2.40 g, 74%) as white solid. $^1$H NMR (270 MHz, CDCl$_3$) δ ppm 1.51 (3H, d, J=7.2 Hz), 2.00 (3H, s), 2.30 (3H, s), 3.83 (3H, s), 5.20-5.40 (1H, m), 5.91 (1H, m), 6.91 (1H, s), 7.06 (1H, s).

MS (ESI) m/z not observed M$^+$ peak.

Step A-3E: (R)-4-(1-aminoethyl)-5-chloro-2-methoxyphenol hydrochloride

37% Hydrochloric acid (20 ml) was added to a solution of (R)-4-(1-acetamidoethyl)-5-chloro-2-methoxyphenyl acetate (2.40 g, 8.4 mmol) in EtOH (80 ml) and the mixture was refluxed for 48 hours. The reaction mixture was cooled to room temperature, washed with DCM 3 times, and the aqueous layer was evaporated under reduced pressure. The residue was dissolved in diisopropyl ether and the precipitate was collected by filtration. The solid was washed with DCM and dried in vacuo to give the title compound (1.21 g, 60%) as white solid. $^1$H NMR (300 MHz, DMSO-d$_6$) δ ppm 1.49 (3H, d, J=6.6 Hz), 3.82 (3H, s), 4.55 (1H, m), 6.91 (1H, s), 7.54 (1H, s), 8.76 (3H, br. s), 9.87 (1H, br. s). MS (ESI) m/z not observed M+ peak.

Amine 4: (R)-1-(2-Chloro-4-methoxy-5-methylphenyl)ethanamine

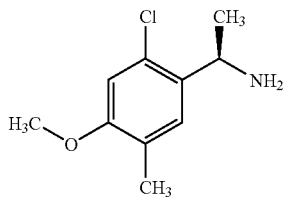

Step A-4A: (R)—N—((R or S)-1-(2-chloro-4-methoxy-5-methylphenyl)ethyl)-2-methylpropane-2-sulfinamide To a THF (20.1 ml) solution of 1-(2-chloro-4-methoxy-5-methylphenyl)ethanone (1.91 g, 9.6 mmol, Journal of the Chemical Society, 1946, 1866-1869) and (R)-(+)-2-methyl-2-propanesulfinylamide (1.28 g, 10.6 mmol), titanium(IV) ethoxide (20.1 ml, 96.0 mmol) was added in the same procedure described in preparation A-3A. The crude residue was applied to a silica gel column chromatography and eluted with EtOAc-Hexane (1:4 to 1:1) to furnish the title compounds (less polar, (R)-isomer, 1.38 g, 47%) as colorless syrup and (more polar, (S)-isomer, 0.66 g, 23%) as white solid. The stereochemistry was determined by X-ray analysis.

(R)-Isomer $^1$H NMR (300 MHz, CDCl$_3$) δ 1.23 (9H, s), 1.48 (3H, d, J=7.4 Hz), 2.18 (3H, s), 3.48 (1H, br d, J=3.6 Hz), 3.81 (3H, s), 4.89 (1H, m), 6.80 (1H, s), 7.16 (1H, s).

MS (ESI): m/z 304 (M+H)+.

(S)-Isomer $^1$H NMR (300 MHz, CDCl$_3$) δ 1.20 (9H, s), 1.52 (3H, d, J=6.7 Hz), 2.17 (3H, s), 3.30 (1H, br d, J=4.4 Hz), 3.81 (3H, s), 4.94 (1H, m), 6.80 (1H, s), 7.16 (1H, s).

MS (ESI): m/z 304 (M+H)+.

Step A-4B: (R)-1-(2-chloro-4-methoxy-5-methylphenyl)ethanamine hydrochloride To ((R)—N—((R)-1-(2-chloro-4-methoxy-5-methylphenyl)ethyl)-2-methylpropane-2-sulfinamide (0.64 g, 2.1 mmol) was added 10% hydrogen chloride in methanol (10 ml), and the resulting mixture was stirred at room temperature for 3 h. The reaction mixture was evaporated and dried in vacuo to give the title compound (crude 0.63 g) as white solid. This amine was used for the next step without further purification.

$^1$H NMR (300 MHz, DMSO-d$_6$) δ ppm 1.47 (3H, d, J=7.4 Hz), 2.14 (3H, s), 3.82 (3H, s), 4.59 (1H, m), 7.06 (1H, s), 7.56 (1H, s), 8.61 (3H, br s). MS (ESI) m/z 183 (M+H—NH$_2$)+.

Amine 5: (S)-1-(2-Chloro-4-methoxy-5-methylphenyl)ethanamine

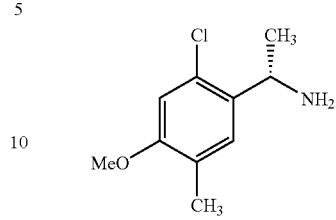

To ((R)—N—((S)-1-(2-chloro-4-methoxy-5-methylphenyl)ethyl)-2-methyl propane-2-sulfinamide (0.66 g, 2.2 mmol) was added 10% hydrogen chloride in methanol (10 ml), and the resulting mixture was stirred at room temperature for 3 h. The reaction mixture was evaporated and dried in vacuo to give the title compound (crude 0.66 g) as white solid. This amine was used for the next step without further purification.

$^1$H NMR (300 MHz, DMSO-d$_6$) δ ppm 1.47 (3H, d, J=7.4 Hz), 2.14 (3H, s), 3.82 (3H, s), 4.59 (1H, m), 7.06 (1H, s), 7.56 (1H, s), 8.61 (3H, br s). MS (ESI) m/z 183 (M+H—NH$_2$)+.

Amine 6: 4-(Aminomethyl)-5-fluoro-2-methylphenol hydrochloride

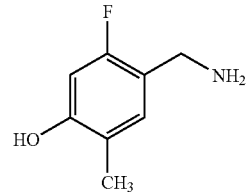

Step A-6A: 2-Fluoro-4-hydroxy-5-methylbenzaldehyde

To a solution of 5-fluoro-2-methylphenol (630 mg, 5 mmol) in dichloromethane (5 ml) was added titanium chloride (1890 mg, 10 mmol) dropwise at 0° C. and then (dichloromethyl)-methyl ether (689 mg, 6 mmol) was added dropwise. The mixture was stirred at 0° C. for 1 hour, quenched with ice (50 g) and extracted with ethyl acetate. The organic layer was separated, dried over Na2SO4, concentrated and applied to a silica gel column, eluting with hexane/ethyl acetate (10:1), to furnish the title compound (545 mg, 71% yield) as a white solid. $^1$H NMR (270 MHz, CDCl$_3$) δ 2.25 (3H, s), 6.04 (1H, brs), 6.60 (1H, d, J=11.2 Hz), 7.66 (1H, d, J=7.9 Hz), 10.18 (1H, s).

Step A-6B: N-(2-Fluoro-4-hydroxy-5-methylbenzyl)-2-methylpropane-2-sulfinamide The product of Step A-6A (400 mg, 2.6 mmol) was converted to the title compound (547 mg, 81% yield) in same procedure described in Step A-3A.

$^1$H NMR (300 MHz, CDCl$_3$) δ 1.24 (9H, s), 2.08 (3H, s), 3.60-3.66 (1H, m), 4.11-4.32 (2H, m), 6.29 (1H, d, J=11.7 Hz), 6.95 (1H, d, J=8.8 Hz), 7.70 (1H, brs). MS (ESI): m/z 260 (M+H)+.

Step A-6C: 4-(Aminomethyl)-5-fluoro-2-methylphenol hydrochloride

A solution of the product of Step A-6B (547 mg, 2.11 mmol) in 4M-hydrochloride-methanol solution (10 ml) was stirred at room temperature for 1 hour. The mixture was concentrated under reduced pressure to furnish the title compound (454 mg, quant.) as a white solid. $^1$H NMR (270 MHz, DMSO-$d_6$) δ 2.07 (3H, s), 3.85-3.90 (2H, m), 6.66-6.75 (1H, m), 7.25 (1H, d, J=8.6 Hz), 8.36 (2H, brs), 10.21 (1H, brs). MS (ESI): m/z 154 (M–H)–.

Amine 7: (2-Chloro-4-methoxy-5-methylphenyl)methanamine

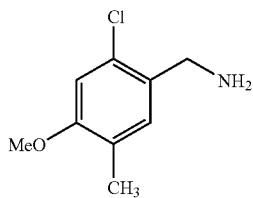

Step A-7A: 2-(2-chloro-4-methoxy-5-methylbenzyl)isoindoline-1,3-dione

To a solution of 5-chloro-2-methylanisole (200 mg, 1.28 mmol, purchased from APOLLO) and (1,3-dioxoisoindolin-2-yl)methyl 2,2,2-trichloroacetimidate (411 mg, 1.28 mmol, *Synthesis*, 2003, 7, 1065-1070) in DCM (30 mL) was added trimethylsilyl trifluoromethansulfonate (14.2 mg, 0.064 mmol) at room temperature under nitrogen. After stirring for 3 hours at room temperature, the reaction mixture was quenched with solid potassium carbonate and evaporated. The residue was chromatographed on a column of silica gel, eluting with EtOAc-Hexane=1:5 to 1:3, to give the title compound (174 mg, 43%) as white solid. $^1$H NMR (300 MHz, CDCl$_3$) δ ppm 2.11 (3H, s), 3.79 (3H, s), 4.91 (2H, s), 6.81 (1H, s), 7.05 (1H, s), 7.60-7.80 (2H, m), 7.80-8.00 (2H, m). MS (ESI) m/z not observed M+ peak.

Step A-7B: (2-chloro-4-methoxy-5-methylphenyl)methanamine 2-(2-Chloro-4-methoxy-5-methylbenzyl)isoindoline-1,3-dione (174 mg, 0.55 mmol) was dissolved in MeOH (30 ml) and hydrazine hydrate (111 mg, 2.21 mmol) and then heated under reflux for 1 hour. The solvent was removed in vacuo and the precipitate was filtered off. The filtrate was evaporated to give a residue, which was chromatographed on a column of silica gel eluting with MeOH-DCM (1:10) to give the title compound (130 mg, 100%) as white solid. $^1$H NMR (270 MHz, DMSO-$d_6$) δ ppm 2.12 (3H, s), 3.38 (2H, br s), 3.69 (2H, s), 3.78 (3H, s), 6.94 (1H, s), 7.29 (1H, s). MS (ESI) m/z 169 (M+H—NH$_2$)+

Amine 8: {4-[(1R)-1-Aminoethyl]phenyl}methanol hydrochloride

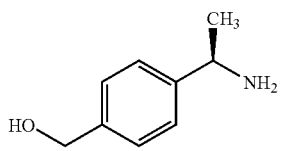

Step A-8A: Methyl 4-{(1R)-1-[(tert-butoxycarbonyl)amino]ethyl}benzoate tert-Butyl[(1R)-1-(4-bromophenyl)ethyl]carbamate (1784 mg, 5.9 mmol) was converted to the title compound (378 mg, 23% yield) in same procedure described in Step C-1A
$^1$H NMR (300 MHz, CDCl$_3$) δ 1.42-1.59 (12H, m), 3.91 (3H, s), 4.82-4.86 (2H, m), 7.37 (2H, d, J=8.1 Hz), 8.00 (2H, d, J=8.1 Hz).

Step A-8B: tert-Butyl{(1R)-1-[4-(hydroxymethyl)phenyl]ethyl}carbamate

To a solution of the product of Step A-8A (375 mg, 1.34 mmol) in Et$_2$O (16 ml) and THF (4 ml) was added lithium aluminum hydride (102 mg, 2.68 mmol) portionwise at –15° C. After 15 minutes, the mixture was stirred at 20° C. for 1 hour. The mixture was diluted with THF (40 ml) and quenched with sodium sulfate.10 hydrate and brine. The organic layer was separated and concentrated to furnish the title compound (417 mg, quant.) as colorless oil. $^1$H NMR (270z, CDCl$_3$) δ1.42-1.59 (12H, m), 3.70-3.75 (1H, m), 4.68 (2H, s), 4.68-4.80 (1H, m), 7.27-7.36 (4H, m).

Step A-8C: {4-[(1R)-1-Aminoethyl]phenyl}methanol hydrochloride

A solution of the product of Step A-8B (416 mg, 1.3 mmol) in 4M-hydrochloride-methanol solution was stirred at room temperature for 2 hours, then concentrated hydrochloride aqueous solution (0.5 ml) was added. After 3 hours, the solvent was removed in vacuo and co-evaporated with toluene to furnish the title compound (322 mg, quant.) as a white solid. $^1$H NMR (300 MHz, DMSO-$d_6$) δ 1.49 (3H, d, J=6.6 Hz), 3.36-3.40 (1H, m), 4.36-4.38 (1H, m), 4.50 (2H, s), 7.35 (2H, d, J=7.3 Hz), 7.45 (2H, d, J=8.1 Hz), 8.49 (2H, brs).

Amine 9: [4-(1-Aminoethyl)-5-fluoro-2-methylphenyl]methanol hydrochloride

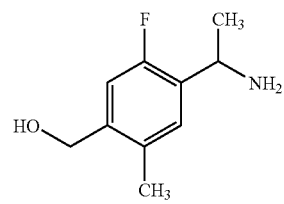

Step A-9A: N-[1-(4-Bromo-2-fluoro-5-methylphenyl)ethyl]-2-methylpropane-2-sulfinamide 1-(4-Bromo-2-fluoro-5-methylphenyl)ethanone (1.78 g, 7.7 mmol) was converted to the title compound (1323 mg, 51% yield) in the procedure described in Step A-3A. $^1$H NMR (270 MHz, CDCl$_3$) δ 1.22 (9H, s), 1.51 (3H, d, J=6.6 Hz), 2.36 (3H, s), 3.49-3.52 (1H, m), 4.63-4.73 (1H, m), 7.19-7.27 (2H, m). MS (ESI): m/z 336, 338 (M+H)+.

Step A-9B: Methyl 4-{1-[(tert-butylsulfinyl)amino]ethyl}-5-fluoro-2-methylbenzoate The product of Step A-9A (700 mg, 2.1 mmol) was converted to the title compound (579 mg, 88% yield) in the procedure described in Step C-1A.

$^1$H NMR (300 MHz, CDCl$_3$) δ 1.23 (9H, s), 1.54 (3H, d, J=6.6 Hz), 2.57 (3H, s), 3.48-3.58 (1H, m), 3.89 (3H, s), 4.72-4.76 (1H, m), 7.22 (1H, d, J=7.3 Hz), 7.61 (1H, d, J=11.0 Hz). MS (ESI): m/z 316 (M+H)+.

Step A-9C: N-{1-[2-Fluoro-4-(hydroxymethyl)-5-methylphenyl]ethyl}-2-methylpropane-2-sulfinamide To a solution of the product of Step A-9B (367 mg, 1.16 mmol) in Et$_2$O (10 ml) was added lithium aluminum hydride (88 mg, 2.33 mmol) at −78° C. The mixture was stirred at −78° C. for 2 hours and at 0° C. for 1 hour. The reaction was quenched with brine (3 ml), and diluted with ethyl acetate (50 ml). The organic layer was dried over sodium sulfate and concentrated to furnish the title compound (380 mg, quant.) as colorless oil. $^1$H NMR (270 MHz, CDCl$_3$) δ 1.22 (9H, s), 1.51 (3H, d, J=6.6 Hz), 1.79 (1H, t, J=5.6 Hz), 2.27 (3H, s), 3.52-3.54 (1H, m), 4.63-4.73 (3H, m), 7.09-7.13 (2H, m). MS (ESI): m/z 288 (M+H)+.

Step A-9D: [4-(1-Aminoethyl)-5-fluoro-2-methylphenyl]methanol hydrochloride

A solution of the product of Step A-9E (380 mg, 1.1 mmol) in 4N hydrochloride-methanol solution (5 ml) was stirred at room temperature for 16 hours. The solvent was removed in vacuo and co-evaporated with toluene to furnish the title compound (363 mg, quant.) as a colorless oil. $^1$H NMR (300 MHz, DMSO-d$_6$) δ 1.50 (3H, d, J=7.3 Hz), 2.19 (3H, s), 4.42-4.57 (3H, m), 7.14-7.39 (2H, m), 8.84 (1H, brs).

Amine 10: (R)-4-(1-Aminoethyl)-2-methoxyphenol

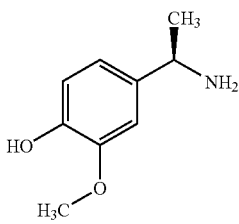

The title amine was prepared by the method described in Sankyo Kenkyusho Nenpo, 1990, 42, 41-64, or is commercially available from NetChem.

Carboxylic Acid 1: 6-tert-Butyl-2-naphthoic acid

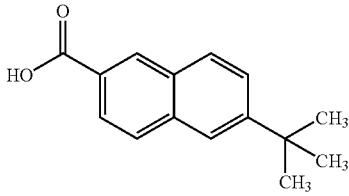

Step C-1A: Methyl 6-tert-butyl-2-naphthoate

A mixture of 2-bromo-6-tert-butylnaphthalene (980 mg, 3.72 mmol), palladium acetate (84 mg, 0.37 mmol), 1,3-bis(diphenylphophino)propane (153 mg, 0.37 mmol) and triethylamine (1.56 ml, 11.2 mmol) in MeOH (6 ml) and DMF (10 ml) was heated at 80° C. under carbon monooxide gas pressure (balloon) for 15 hours. After cooling to ambient temperature, the mixture was diluted with EtOAc-toluene (8:1) (160 ml) and filtered through a pad of celite. The filtrate and washings were washed with water, then brine, dried over sodium sulfate and evaporated in vacuo to give the crude product which was purified through silica gel column chromatography, eluting with hexane/EtOAc (10:1), to furnish the title compound as colorless oil (843 mg, 94%). $^1$H NMR (CDCl$_3$): δ 1.43 (9H, s), 3.97 (3H, s), 7.61-7.67 (1H, m), 7.79-7.93 (3H, m), 8.01-8.07 (1H, m), 8.57 (1H, br, s).

Step C-1B: 6-tert-Butyl-2-naphthoic acid

A mixture of methyl 6-tert-butyl-2-naphthoate (843 mg, 3.48 mmol) and 2M sodium hydroxide solution (6.96 mmol, 3.48 mmol) in MeOH (30 ml) was heated at 60° C. for 3 hours. After cooling to ambient temperature, the solvent was evaporated in vacuo and the residue was acidified to pH 2 with 2M hydrochloric aqueous solution. The aqueous layer was extracted with EtOAc and the combined solution was washed with brine, dried over sodium sulfate and evaporated in vacuo to give the crude product which was recrystallized from EtOAc and hexane to furnish the title compound as a white solid (614 mg, 77%). $^1$H NMR (DMSO-d$_6$): δ 1.39 (9H, s), 7.70-7.76 (1H, m), 7.90-8.08 (4H, m), 8.55 (1H, br, s), 13.00 (1H, br, s).

Carboxylic Acid 2: 6-tert-Butylquinoline-2-carboxylic acid

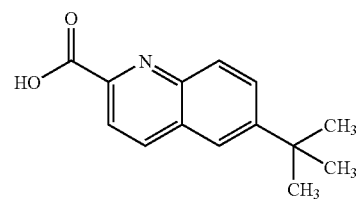

Step C-2A: 6-tert-Butylquinoline 1-oxide

A mixture of 6-tert-butylquinoline (400 mg, 2.16 mmol, Journal of the Indian Chemical Society, 1998, 823) and mCPBA (639 mg, 2.59 mmol) in chloroform (10 ml) was stirred for 2 hours at room temperature. The mixture was concentrated and the crude residue was applied to a silica gel (NH silica) column and eluted with DCM/MeOH (20:1) to furnish the title compound (433 mg, quant.) as pale orange oil.

$^1$H NMR (300 MHz, CDCl$_3$) δ 1.43 (9H, s) 7.26-7.30 (1H, m), 7.73 (1H, d, J=8.1 Hz), 7.78 (1H, s), 7.85 (1H, dd, J=1.5, 8.8 Hz), 8.49 (1H, d, J=5.9 Hz), 8.67 (1H, d, J=8.8 Hz). MS (ESI): m/z 202 (M+H)+.

Step C-2B: 6-tert-Butylquinoline-2-carbonitrile

A mixture of 6-tert-butylquinoline 1-oxide (310 mg, 1.54 mmol), trimethylsilylcyanide (458 mg, 4.62 mmol), and trimethylamine (312 mg, 3.08 mmol) in acetonitrile (3 ml) was stirred for 15 minutes at 120° C. under microwave irradiation. The mixture was applied to a silica gel column and eluted with hexane/EtOAc (20:1) to furnish the title compound (295 mg, 91% yield) as a white solid. $^1$H NMR (300 MHz, CDCl$_3$) δ 1.44 (9H, s), 7.68 (1H, d, J=8.8 Hz), 7.79 (1H, d, J=2.2 Hz), 7.94 (1H, d, J=2.2, 8.8 Hz), 8.11 (1H, d, J=8.8 Hz), 8.26 (1H, d, J=8.8 Hz). MS (ESI): m/z 211 (M+H)+.

Step C-2C: 6-tert-Butylquinoline-2-carboxylic acid

A solution of 6-tert-butylquinoline-2-carbonitrile (295 mg, 1.40 mmol) and 2M-aqueous sodium hydroxide (3 ml) in EtOH (4.5 ml) was stirred for 4 hours at reflux. The mixture was diluted with water (10 ml), neutralized by 2M-aqueous hydrochloride and extracted with EtOAc (30 ml). The organic layer was dried over sodium sulfate, filtrated, and concentrated in vacuo to furnish the title compound (313 mg, quant.) as a white solid.
$^1$H NMR (300 MHz, DMSO-$d_6$) δ 1.40 (9H, s), 7.93-7.97 (2H, m), 8.01-8.11 (2H, m), 8.41 (1H, d, J=8.1 Hz). MS (ESI): m/z 230 (M+H)+.

Carboxylic Acid 3: 7-(Trifluoromethyl)quinoline-3-carboxylic acid

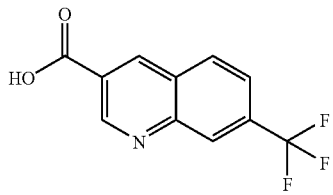

This compound was synthesized according to the process described in the Journal of Medicinal Chemistry (1979), 22(7), 816-23.

Carboxylic Acid 4: 2-tert-Butylquinoline-6-carboxylic acid

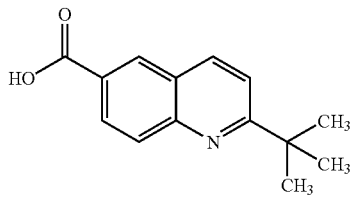

Step C-4A: Methyl 2-tert-butylquinoline-6-carboxylate

To a THF (20 ml) solution of methyl quinoline-6-carboxylate (984 mg, 5.26 mmol, J. O. C., 2002, 67, 7890) was added t-butylmagnesium chloride in THF (15.8 ml, 1M solution) dropwise at −78° C. over 30 min. The mixture was stirred at −78° C. for 30 minutes and at −40° C. for 30 minutes, then at room temperature for 1 hour. The reaction was quenched with saturated ammonium chloride aqueous solution (100 ml) and extracted with ethyl acetate (100 ml×2) which was dried over sodium sulfate. Then, filtration and evaporation gave a yellow oil, which was dissolved in THF (50 ml) and manganese dioxide (1.83 g 15.8 mmol) was added. After the mixture was stirred at room temperature for 2.5 hours, the precipitate was removed through a pad of celite and washed with ethyl acetate. The filtrate was concentrated and purified through silica gel column chromatography, eluting with Hexane/Ethyl acetate (20:1), to furnish the title compound (348 mg, 27% yield) as a white solid. $^1$H NMR (300 MHz, CDCl$_3$) δ 1.48 (9H, s), 3.99 (3H, s), 7.59 (1H, d, J=8.8 Hz), 8.08 (1H, d, J=8.8 Hz), 8.17 (1H, d, J=8.8 Hz), 8.26 (1H, dd, J=2.2, 8.8 Hz), 8.55 (1H, d, J=2.2 Hz). MS (ESI): m/z 244 (M+H)+.

Step C-4B: 2-tert-Butylquinoline-6-carboxylic acid

To a solution of methyl 2-tert-butylquinoline-6-carboxylate (347 mg, 1.43 mmol) in methanol (4 ml) and THF (4 ml) was added 2N aqueous sodium hydroxide (2 ml) at room temperature. The mixture was stirred at room temperature for 1.5 hours, then evaporated, diluted with water (5 ml), and neutralized to pH 5~6 by 2M aqueous hydrochloride. The formed precipitate was collected and washed with water to furnish the title compound (282 mg, 86% yield) as a white solid. $^1$H NMR (300 MHz, CDCl$_3$) δ1.49 (9H, s), 7.62 (1H, d, J=8.8 Hz), 8.13 (1H, d, J=8.8 Hz), 8.20 (1H, d, J=8.8 Hz), 8.31-8.34 (1H, m), 8.64-8.66 (1H, m). MS (ESI): m/z 230 (M+H)+.

Carboxylic Acid 5: 2-(2,2,2-Trifluoro-1,1-dimethylethyl)quinoline-6-carboxylic acid

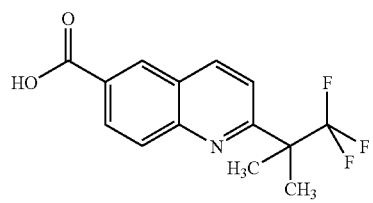

Step C-5A: 6-Bromo-N-methoxy-N-methylquinoline-2-carboxamide

A DMF (1 ml) solution of 6-bromoquinoline-2-carboxylic acid (4000 mg, 15.9 mmol, US2005165049A1), triethylamine (6.64 ml, 47.6 mmol), N,O-dimethylhydroxyamine hydrochloride (1860 mg, 19.0 mmol) and HBTU (6620 mg, 17.5 mmol) was treated in the procedure described in Example 1, Step G. The crude residue was applied to a silica gel column and eluted with hexane/ethyl acetate (4:1) to furnish the title compound (4.29 g, 92% yield) as an orange solid. $^1$H NMR (300 MHz, CDCl$_3$) δ 3.47 (3H, s), 3.80 (3H, s), 7.68-7.80 (1H, brs), 7.81-7.85 (1H, m), 8.00-8.06 (2H, m), 8.17 (1H, d, J=8.1 Hz). MS (ESI): m/z 295, 297 (M+H)$^+$.

Step C-5B: 1-(6-Bromoquinolin-2-yl)ethanone

To a solution of 6-bromo-N-methoxy-N-methylquinoline-2-carboxamide (4.29 g, 14.5 mmol) in THF (100 ml) was added methyl magnesiumbromide (18.2 ml, 17.4 mmol, 0.96M in THF solution) at 0° C. dropwise and the mixture was stirred at 0° C. for 1 hour. Then, the mixture was quenched with saturated ammonium chloride aqueous solution (50 ml) and water (200 ml). After stirring for 30 min, the product was extracted with ethyl acetate which was dried over sodium sulfate. Then, filtration, evaporation and purification through silica gel column chromatography, eluting with hexane/ethyl acetate (4:1), furnished the title compound (3.47 g, 96% yield) as a white solid. $^1$H NMR (300 MHz, CDCl$_3$) δ 2.66 (3H, s), 7.83-7.88 (1H, m), 8.02-8.20 (4H, m). MS (ESI): m/z 250, 252 (M+H)$^+$.

Step C-5C: 2-(6-Bromoquinolin-2-yl)-1,1,1-trifluoropropan-2-ol

A DMF (5 ml) solution of 1-(6-bromoquinolin-2-yl)ethanone (129 mg, 0.52 mmol), (trifluoromethyl)trimethylsilane (220 mg, 1.55 mmol) and tetrabutylammonium fluoride (13.5 mg, 0.052 mmol) was stirred at 100° C. for 2 hours. Then the mixture was cooled to room temperature and 1N-hydrochloride aqueous solution (2 ml) was added. After 4 hours, the mixture was quenched with saturated sodium bicarbonate aqueous solution, and the product was extracted with ethyl acetate which was dried over sodium sulfate. Then, filtration, evaporation and purification through silica gel column chromatography, eluting with hexane/ethyl acetate (4:1), furnished the title compound (175 mg, quant.) as a white solid. $^1$H NMR (300 MHz, CDCl$_3$) δ 1.81 (3H, s), 6.51 (1H, s), 7.64 (1H, d, J=8.1 Hz), 7.66-7.89 (1H, m), 8.00-8.12 (2H, m), 8.21 (1H, d, J=8.8 Hz). MS (ESI): m/z 320, 322 (M+H)$^+$.

Step C-5D: 1-(6-Bromoquinolin-2-yl)-2,2,2-trifluoro-1-methylethyl methanesulfonate To a solution of of 2-(6-bromoquinolin-2-yl)-1,1,1-trifluoropropan-2-ol (1.93 g, 6.03 mmol) in THF (20 ml) was added sodium hydride (241 mg, 7.23 mmol) portionwise at 0° C. and the mixture was stirred at room temperature for 1 hour. A solution of methanesulfonyl chloride (829 mg, 7.23 mmol) in THF (2 ml) was added at 0°. Then the reaction mixture was stirred at room temperature for 16 hours. The mixture was quenched with saturated sodium bicarbonate aqueous solution, and the product was extracted with ethyl acetate which was dried over sodium sulfate. Then, filtration, evaporation and purification through silica gel column chromatography, eluting with hexane/ethyl acetate (15:1 to 5:1), furnished the title compound (1.11 g, 46% yield) as a white solid. $^1$H NMR (300 MHz, CDCl$_3$) δ 2.45 (3H, s), 3.24 (3H, s), 7.81-7.86 (2H, m), 7.96-8.05 (2H, m), 8.17 (1H, d, J=8.8 Hz). MS (ESI): m/z 397, 399 (M+H)$^+$.

Step C-5E: 6-Bromo-2-(2,2,2-trifluoro-1,1-dimethylethyl)quinoline

To a suspension of 1-(6-bromoquinolin-2-yl)-2,2,2-trifluoro-1-methylethyl methanesulfonate (1.40 g, 3.52 mmol) in cyclohexane (14 ml) was added trimethylaluminum (14 ml, 14 mmol, 1.03M in hexane solution) at room temperature, and the mixture was stirred at room temperature for 16 hours. The reaction was carefully quenched with saturated sodium bicarbonate aqueous solution (10 ml), brine (10 ml) and diluted with ethyl acetate (100 ml). After the mixture was stirred for 30 minutes, formed precipitate was removed by celite and washed with ethyl acetate. The filtrate was concentrated and purified through silica gel column chromatography, eluting with hexane only, to furnish the title compound (951 mg, 85% yield) as colorless oil. $^1$H NMR (300 MHz, CDCl$_3$) δ 1.72 (6H, s), 7.66 (1H, d, J=8.8 Hz), 7.75-7.80 (1H, m), 7.96-8.00 (2H, m), 8.06 (1H, d, J=8.8 Hz). MS (ESI): m/z 318, 320 (M+H)$^+$.

Step C-5F: Methyl 2-(2,2,2-trifluoro-1,1-dimethylethyl)quinoline-6-carboxylate A mixture of 6-bromo-2-(2,2,2-trifluoro-1,1-dimethylethyl)quinoline (950 mg, 3.0 mmol), triethylamine (1.25 ml, 9.0 mmol), 1,3-bis(diphenylphosphino)propane (123 mg, 0.3 mmol), palladium acetate (67 mg, 0.3 mmol) and methanol (4.8 ml) in DMF (10 ml) was stirred at reflux under carbon monoxide (1 atm) for 16 hours. Then the reaction was quenched with saturated sodium bicarbonate aqueous solution and the product was extracted with ethyl acetate which was dried over sodium sulfate. Then, filtration, evaporation and purification through silica gel column chromatography, eluting with hexane/ethyl acetate (25:1), furnished the title compound (777 mg, 88% yield) as a white solid. $^1$H NMR (300 MHz, CDCl$_3$) δ 1.74 (6H, s), 4.00 (3H, s), 7.71 (1H, d, J=8.8 Hz), 8.14 (1H, d, J=8.8 Hz), 8.25 (1H, d, J=8.8 Hz), 8.28-8.32 (1H, m), 8.58-8.59 (1H, m). MS (ESI): m/z 298 (M+H)$^+$.

Step C-5G: 2-(2,2,2-Trifluoro-1,1-dimethylethyl)quinoline-6-carboxylic acid)

A methanol (6 ml) and THF (6 ml) solution of methyl 2-(2,2,2-trifluoro-1,1-dimethylethyl)quinoline-6-carboxylate (777 mg, 2.6 mmol) and 2M sodium hydroxide aqueous solution (2.6 ml, 5.2 mmol) was treated in the procedure described in Step C-2C to furnish the title compound (735 mg, 99% yield) as a white solid. $^1$H NMR (300 MHz, CDCl$_3$) δ 1.75 (6H, s), 7.74 (1H, d, J=8.8 Hz), 8.19 (1H, d, J=8.8 Hz), 8.29 (1H, d, J=8.8 Hz), 8.35-8.40 (1H, m), 8.69-8.70 (1H, m). MS (ESI): m/z 284 (M+H)$^+$.

Example A1

6-tert-Butyl-N-[(1R)-1-(2-chloro-4-methoxy-5-methylphenyl)ethyl]-2-naphthamide

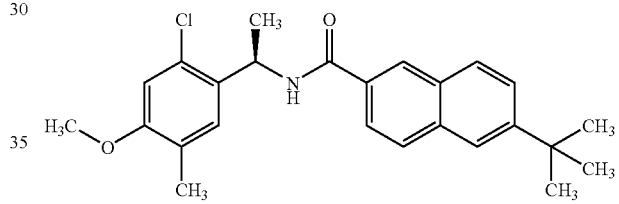

To a DMF (30 ml) solution of Amine 4 (100 mg, 0.44 mmol), Carboxylic Acid 1 (73 mg, 0.44 mmol), HBTU (178 mg, 0.47 mmol) and trimethylamine (1 ml) were added and the mixture was stirred for 3 hours at room temperature. The reaction was quenched with water and the product was extracted with EtOAc. Then, evaporation and purification through silica gel column chromatography gave the title compound (72.9 mg, 50%) as a white solid. $^1$H NMR (270 MHz, CDCl$_3$) δ 1.39 (9H, s), 1.45 (3H, d, J=7.3 Hz), 2.11 (3H, s), 3.79 (3H, s), 5.46 (1H, m), 6.97 (1H, s), 7.36 (1H, s), 7.72 (1H, d, J=9.2 Hz), 7.84-8.03 (4H, m), 8.93 (1H, d, J=7.3 Hz). MS (ESI): m/z 410 (M+H)$^+$

Example A2

6-tert-Butyl-N-[(1R)-1-(2-chloro-4-hydroxy-5-methylphenyl)ethyl]-2-naphthamide

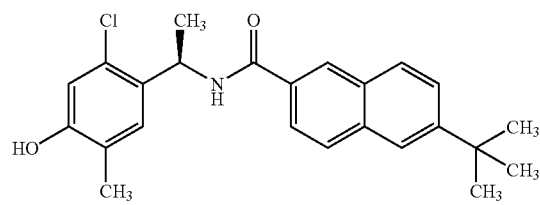

To a DCM (10 mL) solution of Example A1 (111 mg, 0.271 mmol) was added boron tribromide (1.0M solution in DCM, 1.08 ml, 1.08 mmol) at 0° C. under nitrogen, and the resulting mixture was stirred at room temperature for 3 hours. The reaction mixture was quenched with saturated aqueous sodium bicarbonate (30 ml), extracted with DCM (30 ml×3 times), and the combined organic layer was dried over sodium sulfate. Removal of the solvent gave a residue, which was chromatographed on a column of silica gel, eluting with EtOAc-Hexane (1:2 to 1:1), gave the phenol compound of Example A2 (90.4 mg, 84%) as white solid. $^1$H NMR (300 MHz, DMSO-d$_6$) δ 1.40 (9H, s), 1.43 (3H, d, J=6.6 Hz), 2.08 (3H, s), 5.42 (1H, m), 6.80 (1H, s), 7.29 (1H, s), 7.72 (1H, d, J=8.8 Hz), 7.84-8.03 (4H, m), 8.89 (1H, d, J=7.3 Hz), 9.67 (1H, s). MS (ESI): m/z 396 (M+H)$^+$

Example B1

6-tert-Butyl-N-(2-chloro-4-hydroxy-5-methylbenzyl)quinoline-2-carboxamide

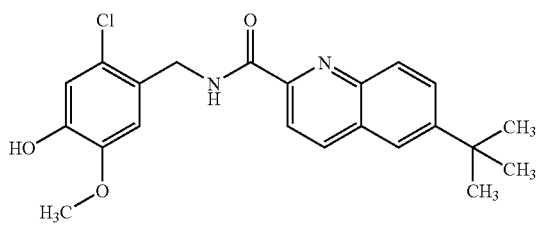

Example B1 was prepared from Amine A-1 and Caboxylic Acid C-2 by the method described in Example A1 and Scheme 1. $^1$H NMR (270 MHz, CDCl$_3$) δ 1.43 (9H, s), 1.59-1.73 (1H, m), 3.49 (1H, s), 3.84 (3H, s). 4.74 (2H, d, J=6.6 Hz), 5.77-6.02 (1H, m), 6.97 (1H, s), 7.00 (1H, s), 7.78 (1H, d, J=2.0 Hz), 7.85 (1H, dd, J=2.0 Hz, 8.6 Hz), 8.22-8.34 (2H, m), 8:67 (1H, m). MS (ESI): m/z 399 (M+H)$^+$, 397 (M–H)$^+$

Example C1

N-[(1R)-1-(2-Chloro-4-methoxy-5-methylphenyl)ethyl]-7-(trifluoromethyl)quinoline-3-carboxamide

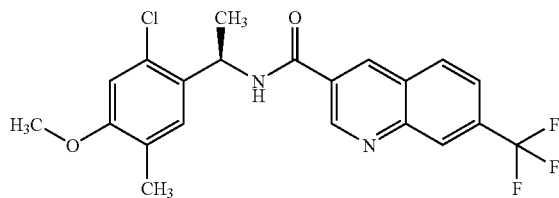

Prepared from Amine A-4 and Carboxylic Acid C-3 by the method described in Example A1 and Scheme 1. $^1$H NMR (270 MHz, CDCl$_3$) δ 1.67 (3H, d, J=7.3 Hz), 2.19 (3H, s), 3.82 (3H, s). 5.56 (1H, m), 6.79 (1H, d, J=7.9 Hz), 6.84 (1H, s), 7.17 (1H, s), 7.97 (1H, dd, J=2.0 Hz, 8.6 Hz), 8.16-8.36 (2H, m), 8.65 (1H, s), 9.38 (1H, d, J=2.6 Hz). MS (ESI): m/z 423 (M+H)$^+$, 421 (M–H)$^+$

Example C2

N-[(1R)-1-(2-Chloro-4-hydroxy-5-methylphenyl)ethyl]-7-(trifluoromethyl)quinoline-3-carboxamide Prepared by demethylation of Example C1 by the method described in Example A2 and Scheme 2. $^1$H NMR (270 MHz, DMSO-d$_6$) δ 1.46 (3H, d, J=7.3 Hz), 2.10 (3H, s), 5.43 (1H, m), 6.81 (1H, s), 7.31 (1H, s), 8.12 (1H, dd, J=2.0 Hz, 6.6 Hz), 8.31 (1H, d, J=8.6 Hz), 8.66 (1H, s), 9.05 (1H, d, J=2.6 Hz), 9.19 (1H, d, J=7.25 Hz), 9.44 (1H, d, J=2.6 Hz), 9.72 (1H, br s). MS (ESI): m/z 409 (M+H)$^+$, 407 (M–H)$^+$.

Example D1

2-tert-Butyl-[(1R)-1-(2-chloro-4-hydroxy-5-methoxyphenyl)ethyl]quinoline-6-carboxamide

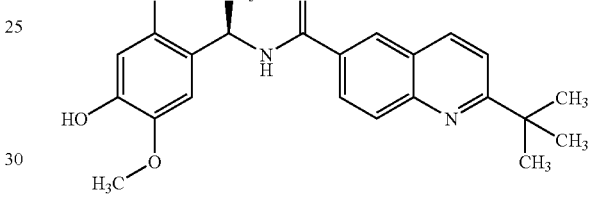

Prepared from Amine A-3 and Carboxylic acid C-4 by the method described in Example A1 and Scheme 1. $^1$H NMR (270 MHz, CDCl$_3$) δ 1.47 (9H, s), 1.67 (3H, d, J=7.3 Hz), 3.88 (3H, s), 5.50 (1H, m), 5.74 (1H, br s), 6.85 (1H, d, J=7.9 Hz), 6.90 (1H, s), 6.97 (1H, s), 7.58 (1H, d, J=9.2 Hz), 7.99 (1H, dd, J=2.0 Hz, 8.6 Hz), 8.09 (1H, d, J=8.6 Hz), 8.13 (1H, d, J=8.6 Hz), 8.26 (1H, d, J=2.0 Hz). MS (ESI): m/z 413 (M+H)$^+$, 411 (M–H)$^+$

Example D2

2-tert-Butyl-N-(2-chloro-4-hydroxy-5-methoxybenzyl)quinoline-6-carboxamide

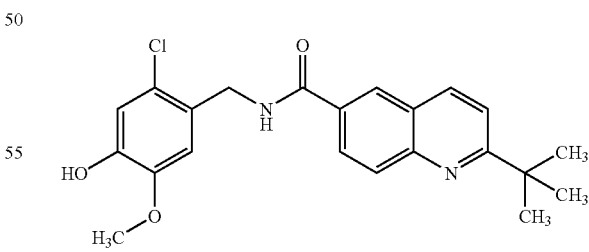

Prepared from Amine A-1 and Carboxylic acid C-4 by the method described in Example A1 and Scheme 1. $^1$H NMR (270 MHz, CDCl$_3$) δ 1.47 (9H, s), 3.89 (3H, s), 4.70 (2H, d, J=5.9 Hz), 5.74 (1H, br s), 6.75 (1H, m), 6.98 (1H, s), 7.04 (1H, s), 7.59 (1H, d, J=8.6 Hz), 7.99 (1H, dd, J=2.0 Hz, 8.6 Hz), 8.09 (1H, d, J=8.6 Hz), 8.14 (1H, d, J=9.2 Hz), 8.24 (1H, s). MS (ESI): m/z 399 (M+H)$^+$, 397 (M–H)$^+$

Example D3

N-(2-Bromo-4-hydroxy-5-methoxybenzyl)-2-tert-butylquinoline-6-carboxamide

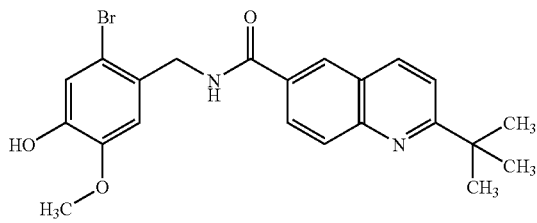

Prepared from Amine A-2 and Carboxylic acid C-4 by the method described in Example A1 and Scheme 1. $^1$H NMR (270 MHz, CDCl$_3$) δ 1.47 (9H, s), 3.89 (3H, s), 4.70 (2H, d, J=5.9 Hz), 5.74 (1H, br s), 6.75 (1H, m), 6.98 (1H, s), 7.04 (1H, s), 7.59 (1H, d, J=8.6 Hz), 7.99 (1H, dd, J=2.0 Hz, 8.6 Hz), 8.09 (1H, d, J=8.6 Hz), 8.14 (1H, d, J=9.2 Hz), 8.24 (1H, s). MS (ESI): m/z 399 (M+H)$^+$, 397 (M−H)$^+$

Example D4

2-tert-Butyl-N-[(1R)-1-(2-chloro-4-methoxy-5-methylphenyl)ethyl]quinoline-6-carboxamide

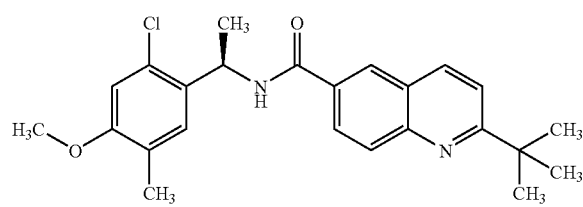

Prepared from Amine A-4 and Carboxylic acid C-4 by the method described in Example A1 and Scheme 1. $^1$H NMR (300 MHz, CDCl$_3$) δ 1.47 (9H, s), 1.64 (3H, d, J=6.6 Hz), 2.17 (3H, s), 3.81 (3H, s), 5.55 (1H, m), 6.78 (1H, m), 6.84 (1H, s), 7.18 (1H, s), 7.57 (1H, d, J=8.8 Hz), 8.01 (1H, dd, J=1.5 Hz, 8.8 Hz), 8.08 (1H, d, J=8.8 Hz), 2.12 (1H, d, J=8.8 Hz), 8.26 (1H, d, J=2.2 Hz). MS (ESI): m/z 411 (M+H)$^+$, 409 (M−H)$^+$

Example D5

2-tert-butyl-N-[(1R)-1-(2-chloro-4-hydroxy-5-methylphenyl)ethyl]5 quinoline-6-carboxamide Prepared by demethylation of Example D4 by the method described in Example A2 and Scheme 2. $^1$H NMR (270 MHz, DMSO-d$_6$) δ 1.43 (9H, s), 1.44 (3H, d, J=6.6 Hz), 2.09 (3H, s), 5.42 (1H, m), 6.80 (1H, s), 7.29 (1H, s), 7.77 (1H, d, J=8.6 Hz), 8.00 (1H, d, J=8.6 Hz), 8.17 (1H, d, J=8.6 Hz), 8.40 (1H, d, J=8.6 Hz), 8.50 (1H, s), 8.95 (1H, d, J=7.9 Hz), 9.66 (1H, br s). MS (ESI): m/z 397 (M+H)$^+$, 395 (M−H)$^+$

Example D6

2-tert-butyl-N-[(1S)-1-(2-chloro-4-methoxy-5-methylphenyl)ethyl]quinoline-6-carboxamide

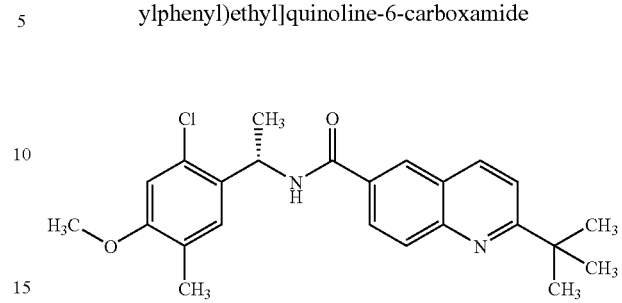

Prepared from Amine A-5 and Carboxylic acid C-4 by the method described in Example A1 and Scheme 1. $^1$H NMR (300 MHz, CDCl$_3$) δ 1.47 (9H, s), 1.64 (3H, d, J=6.6 Hz), 2.17 (3H, s), 3.81 (3H, s), 5.55 (1H, m), 6.78 (1H, m), 6.84 (1H, s), 7.18 (1H, s), 7.57 (1H, d, J=8.8 Hz), 8.01 (1H, dd, J=1.5 Hz, 8.8 Hz), 8.08 (1H, d, J=8.8 Hz), 8.12 (1H, d, J=8.8 Hz), 8.26 (1H, d, J=2.2 Hz). MS (ESI): m/z 411 (M+H)$^+$, 409 (M−H)$^+$

Example D7

2-tert-Butyl-N-[(1S)-1-(2-chloro-4-hydroxy-5-methylphenyl)ethyl]quinoline-6-carboxamide Prepared by demethylation of Example D6 by the method described in Example A2 and Scheme 2, $^1$H NMR (270 MHz, DMSO-d$_6$) δ 1.43 (9H, s), 1.44 (3H, d, J=6.6 Hz), 2.09 (3H, s), 5.42 (1H, m), 6.80 (1H, s), 7.29 (1H, s), 7.77 (1H, d, J=8.6 Hz), 8.00 (1H, d, J=8.6 Hz), 8.17 (1H, d, J=8.6 Hz), 8.40 (1H, d, J=8.6 Hz), 8.50 (1H, s), 8.95 (1H, d, J=7.9 Hz), 9.66 (1H, br s). MS (ESI): m/z 397 (M+H)$^+$, 395 (M−H)$^+$

Example D8

2-tert-Butyl-N-{(1R)-1-[4-(hydroxymethyl)phenyl]ethyl}quinoline-6-carboxamide

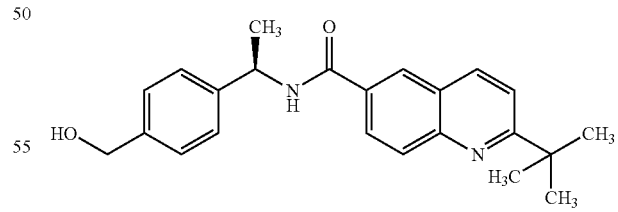

Prepared from Amine A-8 and Carboxylic acid C-4 by the method described in Example A1 and Scheme 1. $^1$H NMR (300 MHz, DMSO) δ1.42 (9H, s), 1.51 (3H, d, J=6.6 Hz), 4.46 (2H, d, J=5.9 Hz), 5.12 (1H, t, J=5.9 Hz), 5.18-5.26 (1H, m), 7.27 (2H, d, J=8.1 Hz), 7.38 (2H, d, J=7.3 Hz), 7.75 (1H, d, J=8.8 Hz), 8.00 (1H, d, J=8.8 Hz), 8.14-8.18 (1H, m), 8.40 (1H, d, J=8.8 Hz), 8.49-8.50 (1H, m), 9.00 (1H, d, J=8.1 Hz). MS (ESI): m/z 363 (M+H)+.

Example D9

2-tert-Butyl-N-(2-chloro-4-methoxy-5-methylbenzyl)quinoline-6-carboxamide

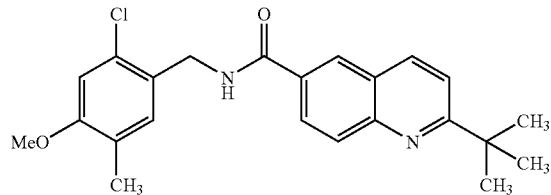

Prepared from Amine A-7 and Carboxylic acid C-4 by the method described in Example A1 and Scheme 1. $^1$H NMR (270 MHz, DMSO-$d_6$) δ 1.43 (9H, s), 2.10 (3H, s), 3.81 (3H, s), 4.52 (2H, d, J=5.9 Hz), 7.03 (1H, s), 7.21 (1H, s), 7.76 (1H, d, J=8.6 Hz), 8.01 (1H, d, J=8.6 Hz), 8.19 (1H, dd, J=2.0 Hz, 9.2 Hz), 8.40 (1H, d, J=8.6 Hz), 8.52 (1H, s), 9.10 (1H, m). MS (ESI): m/z 397 (M+H)$^+$, 395 (M−H)$^+$

Example D10

2-tert-Butyl-N-(2-chloro-4-hydroxy-5-methylbenzyl)quinoline-6-carboxamide

Prepared by demethylation of Example D9 by the method described in Example A2 and Scheme 2. $^1$H NMR (270 MHz, DMSO-$d_6$) δ 1.43 (9H, s), 2.08 (3H, s), 4.47 (2H, d, J=5.9 Hz), 6.84 (1H, s), 7.14 (1H, s), 7.76 (1H, d, J=8.6 Hz), 8.00 (1H, d, J=8.6 Hz), 8.18 (1H, d, J=8.6 Hz), 8.39 (1H, d, J=8.6 Hz), 8.51 (1H, s), 9.04 (1H, m), 8.73 (1H, br s).

MS (ESI): m/z 383 (M+H)$^+$, 381 (M−H)$^+$

Example D11

2-tert-Butyl-N-(2-fluoro-4-hydroxy-5-methylbenzyl)quinoline-6-carboxamide

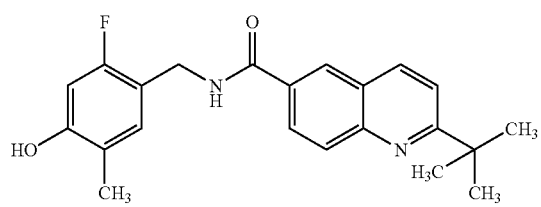

Prepared from Amine A-6 and Carboxylic acid C-4 by the method described in Example A1 and Scheme 1. $^1$H NMR (300 MHz, DMSO-$d_6$) δ1.42 (9H, s), 2.06 (3H, s), 4.42-4.45 (2H, m), 6.57 (1H, d, J=11.0 Hz), 7.11 (1H, d, J=8.8 Hz), 7.76 (1H, d, J=8.8 Hz), 8.00 (1H, d, J=8.8 Hz), 8.17 (1H, d, J=8.8 Hz), 8.38 (1H, d, J=8.8 Hz), 8.49 (1H, s), 9.05 (1H, brs), 9.70 (1H, brs). MS (ESI): m/z 367 (M+H)+.

Example D12

N-[(1R)-1-(2-Chloro-4-methoxy-5-methylphenyl)ethyl]-2-(2,2,2-trifluoro-1,1-dimethylethyl)quinoline-6-carboxamide

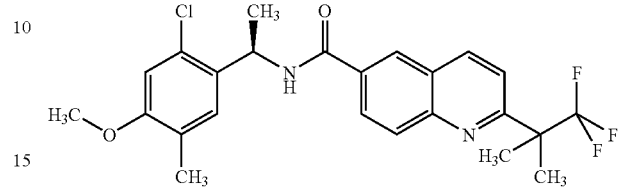

Prepared from Amine A-4 and Carboxylic acid C-5 by the method described in Example A1 and Scheme 1. $^1$H NMR (300 MHz, DMSO-$d_6$) δ1.46 (3H, d, J=6.6 Hz), 1.72 (6H, s), 2.11 (3H, s), 3.79 (3H, s), 5.44-5.48 (1H, m), 6.98 (1H, s), 7.37 (1H, s), 7.88 (1H, d, J=8.1 Hz), 8.09 (1H, d, J=8.8 Hz), 8.24 (1H, d, J=8.8 Hz), 8.54-8.59 (2H, m), 9.08 (1H, d, J=8.1 Hz). MS (ESI): m/z 465 (M+H)+.

Example D13

N-[(1R)-1-(2-Chloro-4-hydroxy-5-methylphenyl)ethyl]-2-(2,2,2-trifluoro-1,1-dimethylethyl)quinoline-6-carboxamide Prepared by demethylation of Example D12 by the method described in Example A2 and Scheme 2. $^1$H NMR (300 MHz, DMSO-$d_6$) δ1.44 (3H, d, J=6.6 Hz), 1.72 (6H, s), 2.08 (3H, s), 5.40-5.44 (1H, m), 6.80 (1H, s), 7.29 (1H, s), 7.89 (1H, d, J=8.8 Hz), 8.09 (1H, d, J=8.8 Hz), 8.22-8.24 (1H, m), 8.53-8.57 (2H, m), 9.03 (1H, d, J=7.3 Hz), 9.70 (1H, brs).

MS (ESI): m/z 451 (M+H)+.

Example D14

N-{1-[2-Fluoro-4-(hydroxymethyl)-5-methylphenyl]ethyl}-2-(2,2,2-trifluoro-1,1-dimethylethyl)quinoline-6-carboxamide

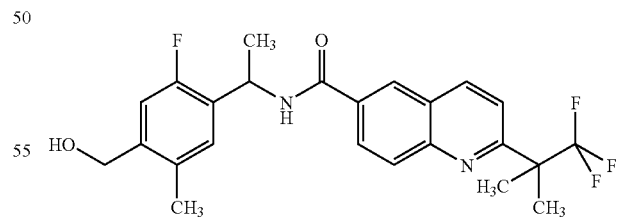

Prepared from Amine A-9 and Carboxylic Acid C-5 by the method described in Example A1 and Scheme 1. $^1$H NMR (300 MHz, DMSO-$d_6$) δ 1.50 (3H, d, J=7.3 Hz), 1.72 (6H, s), 2.17 (3H, s), 4.44 (2H, d, J=5.1 Hz), 5.21 (1H, t, J=5.1 Hz), 5.38-5.46 (1H, m), 7.12 (1H, d, J=11.7 Hz), 7.26 (1H, d, J=8.1 Hz), 7.89 (1H, d, J=8.8 Hz), 8.09 (1H, d, J=8.8 Hz), 8.23 (1H, d, J=9.5 Hz), 8.54-8.59 (2H, m), 9.08 (1H, d, J=7.3 Hz). MS (ESI): m/z 449 (M+H)+.

Example D15

2-tert-Butyl-N-[(1R)-1-(4-hydroxy-3-methoxyphenyl)ethyl]quinoline-6-carboxamide

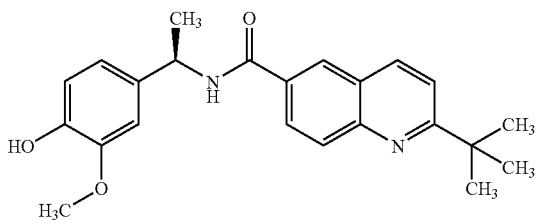

Prepared from Amine 10 and Carboxylic Acid 4 by the method described in Example A1 and Scheme 1. $^1$H NMR (270 MHz, CDCl$_3$) δ 1.47 (9H, s), 1.63 (3H, d, J=7.3 Hz), 3.88 (3H, s), 5.33 (1H, m), 5.85 (1H, brs), 6.60 (1H, m), 6.85-7.00 (3H, m), 7.57 (1H, d, J=8.6 Hz), 7.90-8.15 (3H, m), 8.25 (1H, s). MS (ESI): m/z 379 (M+H)$^+$, 377 (M−H)$^+$.

The invention claimed is:

1. A compound of the formula (I):

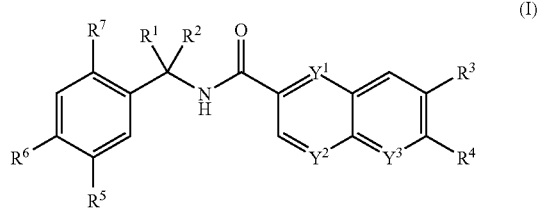

wherein
Y$^1$ and Y$^2$ are CH and Y$^3$ is N;
R$^1$ and R$^2$ are each independently hydrogen, (C$_1$-C$_6$)alkyl, halo(C$_1$-C$_6$)alkyl or hydroxy(C$_1$-C$_6$)alkyl;
R$^3$ is hydrogen, halogen, hydroxy, (C$_1$-C$_6$)alkyl, hydroxy(C$_1$-C$_6$)alkyl, hydroxy(C$_1$-C$_6$)alkoxy, (C$_1$-C$_6$)alkoxy-(C$_1$-C$_6$)alkyl, (C$_1$-C$_6$)alkoxy-(C$_1$-C$_6$)alkoxy or halo(C$_1$-C$_6$)alkyl;
R$^4$ is halogen, (C$_1$-C$_6$)alkyl, (C$_3$-C$_6$)cycloalkyl, halo(C$_1$-C$_6$)alkyl, hydroxy(C$_1$-C$_6$)alkyl, halo(C$_1$-C$_6$)alkoxy, hydroxy(C$_1$-C$_6$)alkoxy, (C$_1$-C$_6$)alkoxy-(C$_1$-C$_6$)alkyl, (C$_1$-C$_6$)alkoxy-(C$_1$-C$_6$)alkoxy, halo(C$_1$-C$_6$)alkylsulfonyl, halo(C$_1$-C$_6$)alkylsulfinyl, halo(C$_1$-C$_6$)alkylthio, [(C$_1$-C$_6$)alkyl]NH—, [(C$_1$-C$_6$)alkyl]$_2$N—, azetidinyl, pyrrolidinyl or piperidinyl;
R$^6$ is, hydroxy, hydroxy(C$_1$-C$_6$)alkyl, or (C$_1$-C$_6$)alkoxy;
R$^5$ is hydrogen, halogen, hydroxy, (C$_1$-C$_6$)alkyl, hydroxy(C$_1$-C$_6$)alkyl, or (C$_1$-C$_6$)alkoxy;
R$^7$ is hydrogen, halogen, hydroxy, (C$_1$-C$_6$)alkyl, hydroxy(C$_1$-C$_6$)alkyl, or (C$_1$-C$_6$)alkoxy;
R$^8$ is hydrogen, halogen, (C$_1$-C$_6$)alkyl or halo(C$_1$-C$_6$)alkyl;
or a pharmaceutically acceptable salt thereof.

2. A compound according to claim 1, or a pharmaceutically acceptable salt thereof, wherein Y$^1$ is CH, Y$^2$ is CH, Y$^3$ is N.

3. A compound according to claim 2, or a pharmaceutically acceptable salt thereof, wherein R$^1$ and R$^2$ are each independently hydrogen or (C$_1$-C$_6$)alkyl.

4. A compound according to claim 1, or a pharmaceutically acceptable salt thereof, wherein R$^1$ is hydrogen or methyl and R$^2$ is hydrogen.

5. A compound according to claim 1, or a pharmaceutically acceptable salt thereof, wherein R$^1$ is methyl and R$^2$ is hydrogen.

6. A compound according to claim 1, or a pharmaceutically acceptable salt thereof, wherein R$^3$ is hydrogen.

7. A compound according to claim 2, or a pharmaceutically acceptable salt thereof, wherein R$^4$ is (C$_1$-C$_6$)alkyl or halo(C$_1$-C$_6$)alkyl.

8. A compound according to claim 1, or a pharmaceutically acceptable salt thereof, wherein R$^4$ is tert-butyl, trifluoromethyl or 2,2,2-trifluoro-1,1-dimethyl-ethyl.

9. A compound according to claim 1, or a pharmaceutically acceptable salt thereof, wherein R$^6$ is hydroxy, hydroxymethyl or methoxy.

10. A compound according to claim 2, or a pharmaceutically acceptable salt thereof, wherein R$^7$ is selected from hydrogen, halogen, hydroxy, (C$_1$-C$_6$)alkyl or (C$_1$-C$_6$)alkoxy.

11. A compound according to claim 2, or a pharmaceutically acceptable salt thereof, wherein R$^7$ is hydrogen or halogen.

12. A compound according to claim 1, or a pharmaceutically acceptable salt thereof, wherein R$^7$ is hydrogen, fluoro, chloro or bromo.

13. A compound according to claim 2, or a pharmaceutically acceptable salt thereof, wherein R$^5$ is selected from hydrogen, halogen, hydroxy, (C$_1$-C$_6$)alkyl or (C$_1$-C$_6$)alkoxy.

14. A compound according to claim 1, or a pharmaceutically acceptable salt thereof, wherein R$^5$ is hydrogen, methyl or methoxy.

15. A compound according to claim 1, or a pharmaceutically acceptable salt thereof, said compound being selected from, 2-tert-butyl-N-[(1R)-1-(2-chloro-4-hydroxy-5-methoxyphenyl)ethyl]quinoline-6-carboxamid;

2-tert-butyl-N-(2-chloro-4-hydroxy-5-methoxybenzyl)quinoline-6-carboxamide;

N-(2-bromo-4-hydroxy-5-methoxybenzyl)-2-tert-butylquinoline-6-carboxamide;

2-tert-butyl-N-[(1R)-1-(2-chloro-4-methoxy-5-methylphenyl)ethyl]quinoline-6-carboxamide;

2-tert-butyl-N-[(1R)-1-(2-chloro-4-hydroxy-5-methylphenyl)ethyl]quinoline-6-carboxamide;

2-tert-butyl-N-[(1S)-1-(2-chloro-4-methoxy-5-methylphenyl)ethyl]quinoline-6-carboxamide;

2-tert-butyl-N-[(1S)-1-(2-chloro-4-hydroxy-5-methylphenyl)ethyl]quinoline-6-carboxamide;

2-tert-butyl-N-{(1R)-1-[4-(hydroxymethyl)phenyl]ethyl}quinoline-6-carboxamide;

2-tert-butyl-N-(2-chloro-4-methoxy-5-methylbenzyl)quinoline-6-carboxamide;

2-tert-butyl-N-(2-chloro-4-hydroxy-5-methylbenzyl)quinoline-6-carboxamide;

2-tert-butyl-N-(2-fluoro-4-hydroxy-5-methylbenzyl)quinoline-6-carboxamide;

N-[(1R)-1-(2-chloro-4-methoxy-5-methylphenyl)ethyl]-2-(2,2,2-trifluoro-1,1-dimethylethyl)quinoline-6-carboxamide;

N-[(1R)-1-(2-chloro-4-hydroxy-5-methylphenyl)ethyl]-2-(2,2,2-trifluoro-1,1-dimethylethyl)quinoline-6-carboxamide;

N-{1-[2-fluoro-4-(hydroxymethyl)-5-methylphenyl]ethyl}-2-(2,2,2-trifluoro-1,1-dimethylethyl)quinoline-6-carboxamide; and, 2-tert-butyl-N-[(1R)-1-(4-hydroxy-3-methoxyphenyl)ethyl]quinoline-6-carboxamide.

16. A pharmaceutical composition including a compound of the formula (I) or a pharmaceutically acceptable salt thereof, as defined in claim 1, together with a pharmaceutically acceptable excipient.

17. A pharmaceutical composition including a compound of the formula (I) or a pharmaceutical acceptable salt as defined in claim 1, and another pharmacologically active agent.

18. A method of treating pain, chronic pain, acute pain, nociceptive pain, neuropathic pain, inflammatory pain, rheumatoid arthritic pain, osteoarthritic pain, back pain, visceral pain, cancer pain, dental pain, headache, migraine, pelvic pain, menstrual pain and post stroke pain in a mammal comprising treating said mammal with an effective amount of a compound of the formula (I) or with a pharmaceutically acceptable salt thereof, as defined in claim 1.

* * * * *